United States Patent
Cantwell et al.

(10) Patent No.: US 10,722,170 B2
(45) Date of Patent: Jul. 28, 2020

(54) CLOSED-LOOP GLUCOSE AND/OR INSULIN CONTROL SYSTEM

(71) Applicant: Medtronic Minimed, Inc., Northridge, CA (US)

(72) Inventors: Martin Cantwell, Canyon County, CA (US); H. Bud Clark, Simi Valley, CA (US); Garry M. Steil, Boston, MA (US)

(73) Assignee: Medtronic Minimed, Inc., Northridge, CA (US)

( * ) Notice: Subject to any disclaimer, the term of this patent is extended or adjusted under 35 U.S.C. 154(b) by 292 days.

(21) Appl. No.: 15/610,921

(22) Filed: Jun. 1, 2017

(65) Prior Publication Data
US 2017/0325736 A1    Nov. 16, 2017

Related U.S. Application Data

(62) Division of application No. 12/486,708, filed on Jun. 17, 2009, now Pat. No. 9,687,194.

(51) Int. Cl.
 *A61B 5/00*    (2006.01)
 *A61M 5/172*    (2006.01)
 (Continued)

(52) U.S. Cl.
 CPC ........ *A61B 5/4839* (2013.01); *A61B 5/14532* (2013.01); *A61M 5/14244* (2013.01);
 (Continued)

(58) Field of Classification Search
 CPC ............ A61M 5/1723; A61M 5/14244; A61B 5/4839; A61B 5/14532
 See application file for complete search history.

(56) References Cited

U.S. PATENT DOCUMENTS

| | | |
|---|---|---|
| 5,391,250 A | 2/1995 | Cheney, II et al. |
| 6,254,586 B1 | 7/2001 | Mann et al. |

(Continued)

FOREIGN PATENT DOCUMENTS

| | | |
|---|---|---|
| WO | WO2004060455 A1 | 7/2004 |
| WO | 2010147659 A2 | 12/2010 |
| WO | WO2010147659 A2 | 12/2010 |

OTHER PUBLICATIONS

Van Den Berghe, Greet, et. al., "Intensive Insulin Therapy in Critcally Ill Patients", The New England Journal of Medicine, Vo. 345, No. 19, Nov. 8, 2001, pp. 1359-1367.

(Continued)

*Primary Examiner* — Kami A Bosworth
*Assistant Examiner* — Leah J Swanson
(74) *Attorney, Agent, or Firm* — Berkeley Law & Technology Group, LLP

(57) ABSTRACT

A method and/or system may be provided for determining a suggested change in a recommended therapy for a patient based, at least in part, on sensor measurements, and generating an alert to an attendant in a hospital environment upon detection of the suggested change. A method and/or system may also be provided to automatically determine a maximum interval to alert an attendant following receipt of a measurement at an operator interface. A method and/or system may also be provided to blood-glucose sensor calibration.

20 Claims, 41 Drawing Sheets

(51) Int. Cl.
*A61B 5/145* (2006.01)
*A61M 5/142* (2006.01)
*A61M 5/158* (2006.01)

(52) U.S. Cl.
CPC ... *A61M 5/1723* (2013.01); *A61B 2560/0276* (2013.01); *A61M 2005/14208* (2013.01); *A61M 2005/1581* (2013.01); *A61M 2205/3569* (2013.01); *A61M 2205/3592* (2013.01); *A61M 2230/201* (2013.01)

(56) References Cited

U.S. PATENT DOCUMENTS

| | | | |
|---|---|---|---|
| 6,360,888 | B1 | 3/2002 | McIvor et al. |
| 6,424,847 | B1 | 7/2002 | Mastrototaro et al. |
| 6,558,320 | B1 | 5/2003 | Causey, III et al. |
| 6,641,533 | B2 | 11/2003 | Causey, III et al. |
| 6,895,263 | B2 | 5/2005 | Shin et al. |
| 7,267,655 | B1 | 9/2007 | Lyapko |
| 7,833,157 | B2 | 11/2010 | Gottlieb |
| 2003/0130616 | A1* | 7/2003 | Steil ............ A61B 5/14532 604/66 |
| 2003/0212379 | A1 | 11/2003 | Bylund et al. |
| 2006/0009727 | A1* | 1/2006 | O'Mahony ........ A61B 5/14532 604/4.01 |
| 2006/0173406 | A1 | 8/2006 | Hayes |
| 2006/0208114 | A1 | 9/2006 | Ko |
| 2008/0021436 | A1* | 1/2008 | Wolpert ............ A61B 5/14532 604/504 |
| 2008/0183060 | A1 | 7/2008 | Steil |
| 2008/0221509 | A1 | 9/2008 | Gottlieb et al. |
| 2008/0269723 | A1 | 10/2008 | Mastrototaro et al. |
| 2009/0105636 | A1 | 4/2009 | Hayter |
| 2010/0094251 | A1* | 4/2010 | Estes ............ A61M 5/14244 604/504 |

2017/0325736 A1 11/2017 Cantwell et al.

OTHER PUBLICATIONS

Kollind, M., "Insulin clearance during hyupoglycemia in patiens with insulin-dependent diabetes mellitus", Horm Metab Res, Jul. 1991; 23(7) pp. 333-335.
Khan, S. E., "Quantification of the relationship between insulin sensitivity and beta-cell function in human subjects. Evidence for a hyperbolic function", Diabetes, Nov. 1993; 42(11) pp. 1663-1672.
Weinzimer, Stuart, et. al., "Fully Automated Closed-Loop Insulin Delivery Versus Semiautomated Hybrid Control in Pediatnc Patients with Type 1 Diabetes Using an Artificial Pancreas" Diabetes Care, American Diabetes Association, vol. 31, No. 5, May 5, 2008, pp. 934-939.
International Patent Application PCT/US2010/001751, filed Jun. 17, 2010, 153 pgs.
International Patent Application PCT/US2010/001751, International Search Report, dated Jan. 14, 2011, 7 pgs.
International Patent Application PCT/US2010/001751, Written Opinion of the International Search Authority, dated Dec. 20, 2011, 13 pgs.
International Patent Application PCT/US2010/001751, International Preliminary Report on Patentability, dated Dec. 20, 2011, 14 pgs.
Canadian Patent Application No. 2,764,647, Examiner's Report, dated Jun. 21, 2016, 4 pgs.
European Patent Application No. EP10729731, Communication pursuant to Rules 161(1) and 162 EPC, dated Jan. 24, 2012, 2 pgs.
Examination Search Report, dated Apr. 5, 2019, International Patent Application No. 3006275, 3 pgs.
Responge to Summons to attend proceedings pursuant to Rule 115(1) EPC, App. No. EP10729731.9, Filed Feb. 26, 2026, 51 Pages.

* cited by examiner

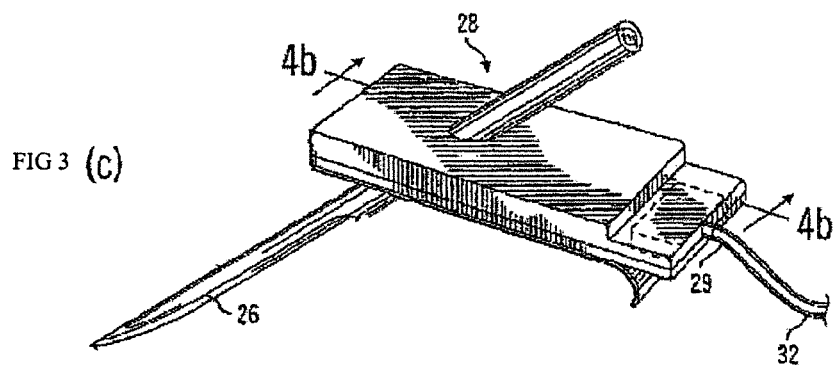
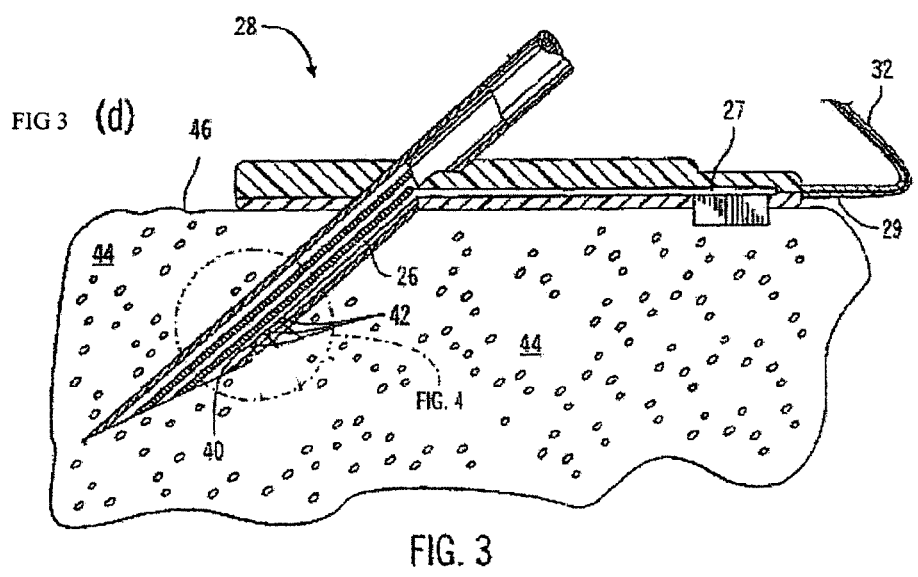
FIG. 3

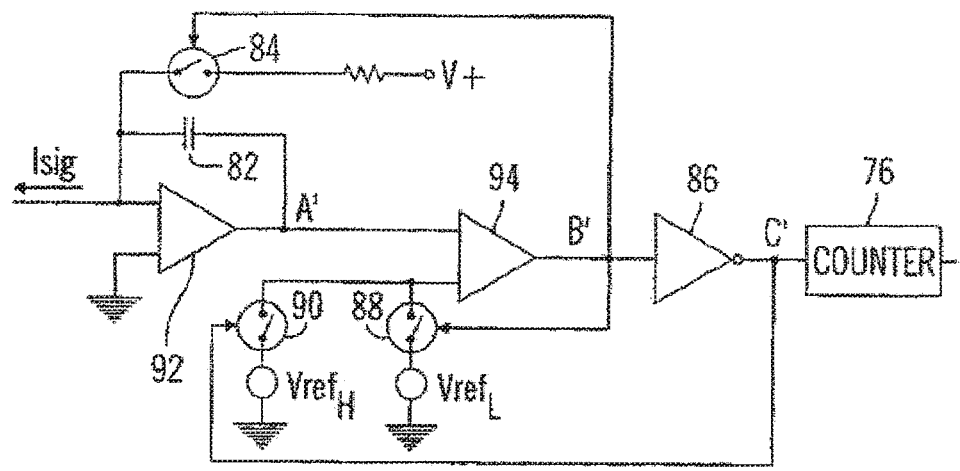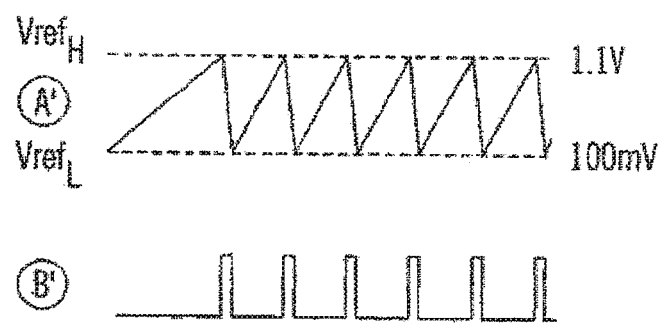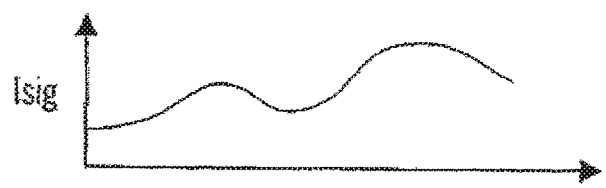
FIG. 12

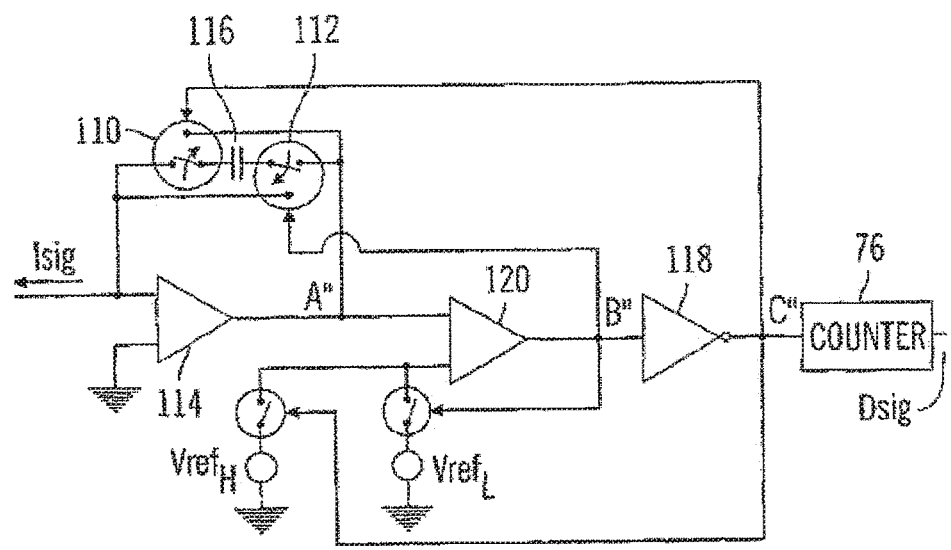
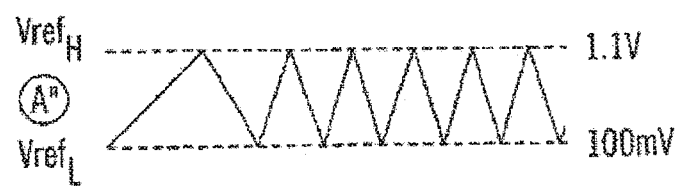
FIG. 13

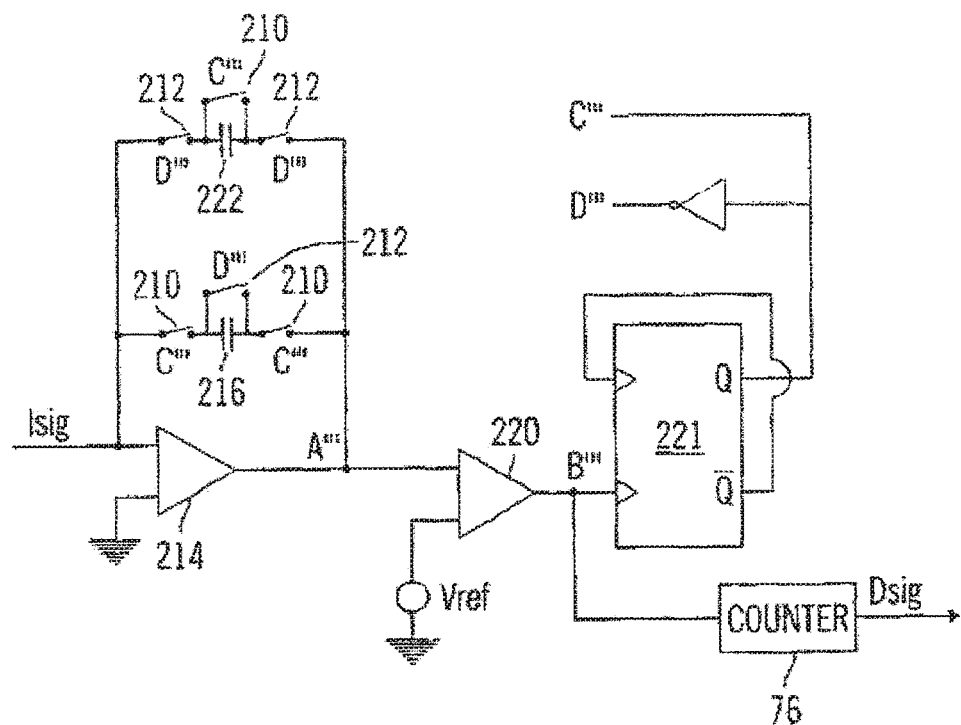
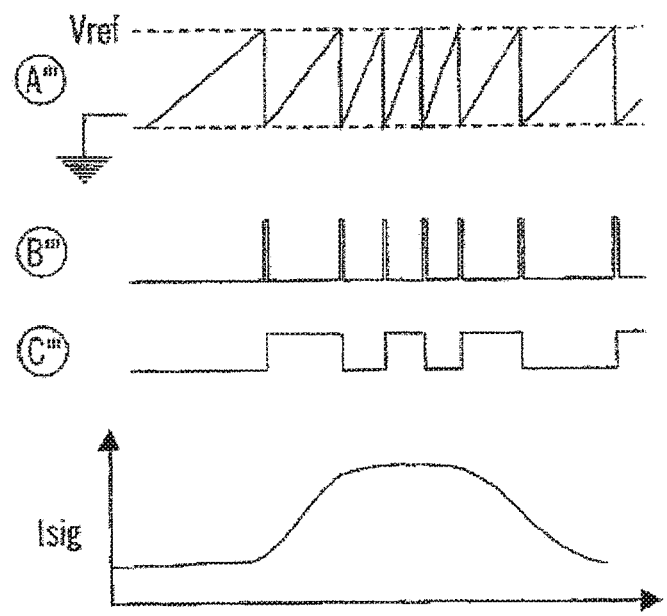
FIG. 14

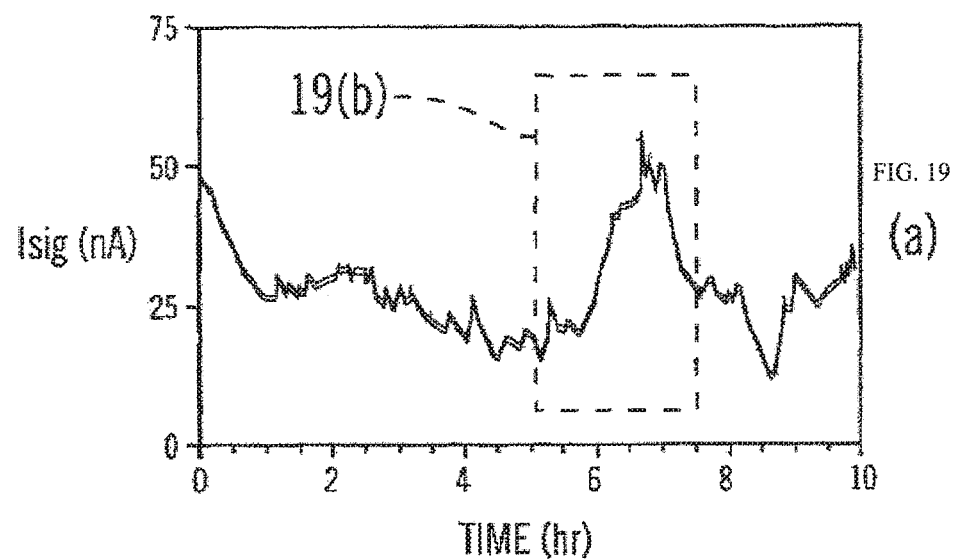
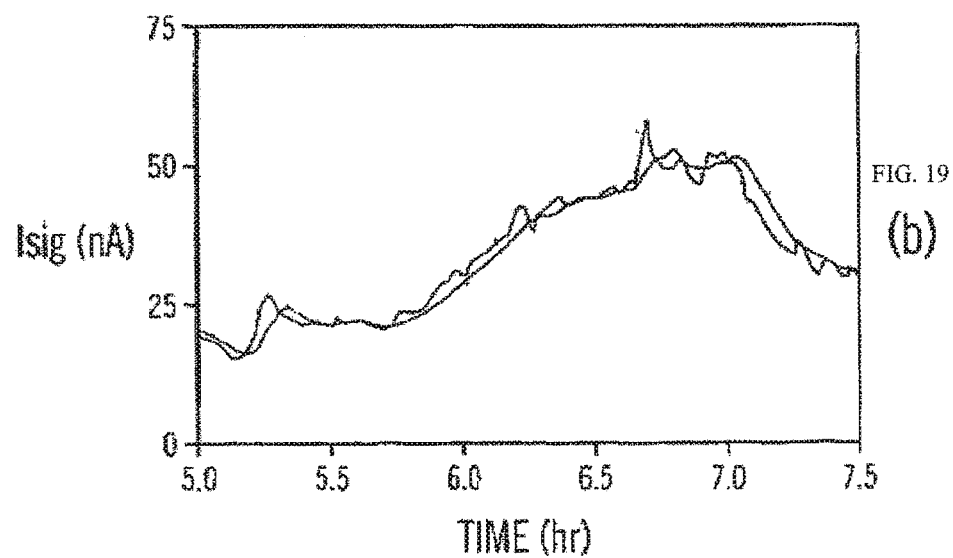
FIG. 19

FIG. 24

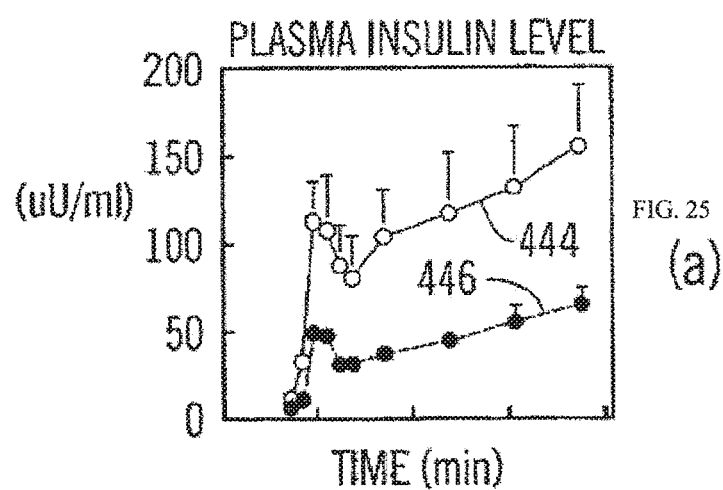
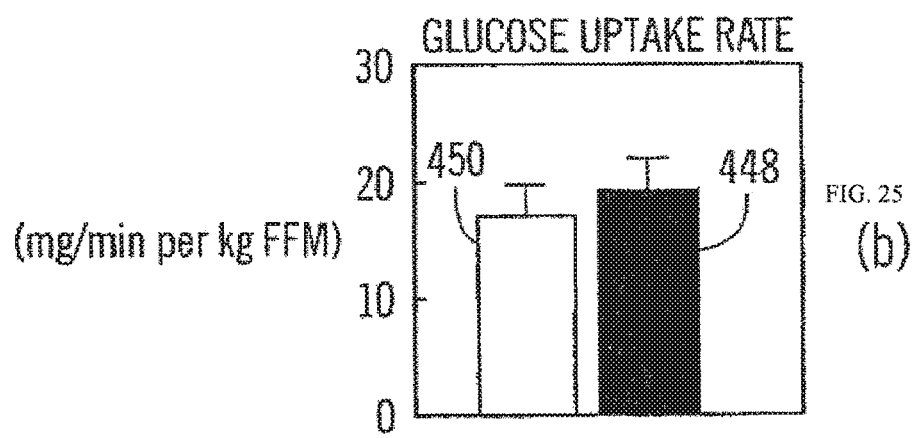
FIG. 25

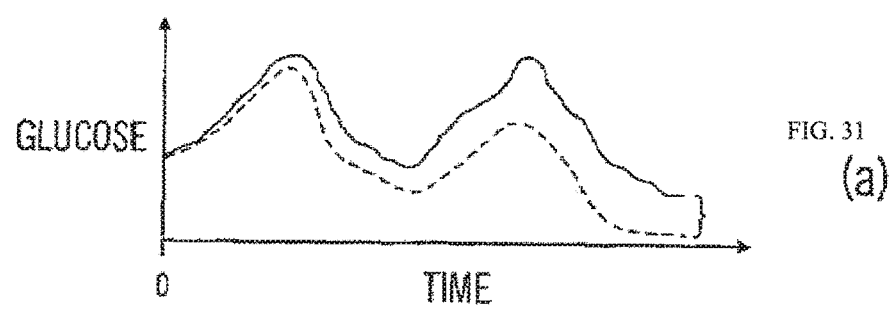
FIG. 31 (a)
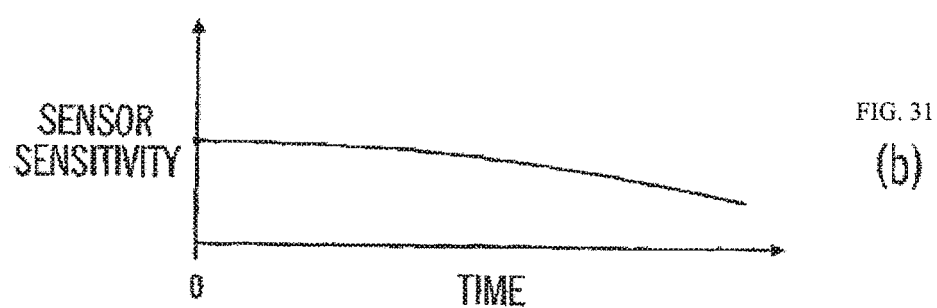
FIG. 31 (b)
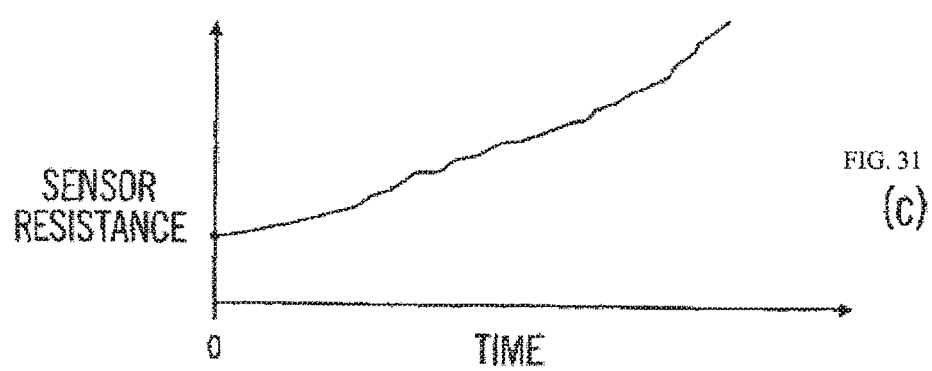
FIG. 31 (c)
FIG. 31

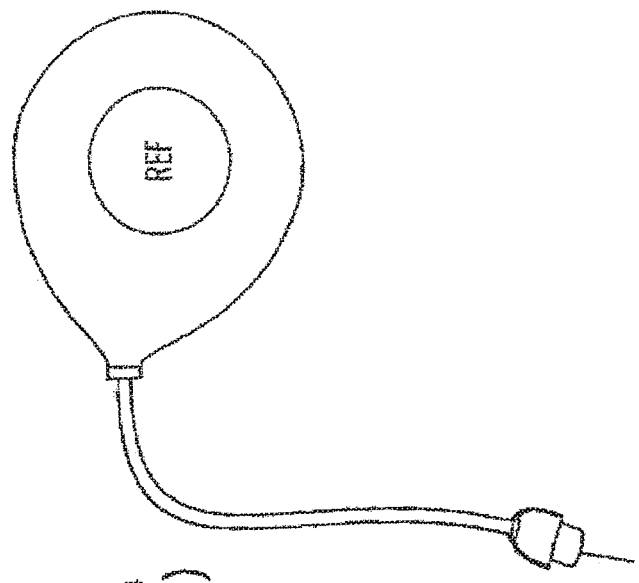
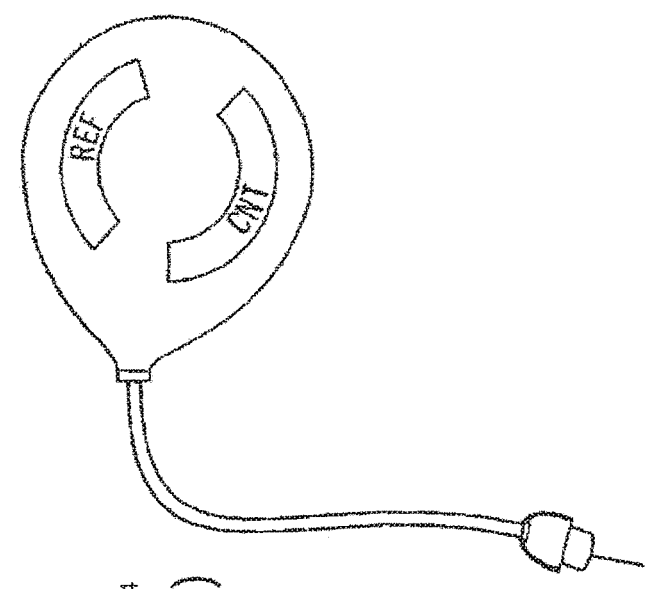
FIG. 34

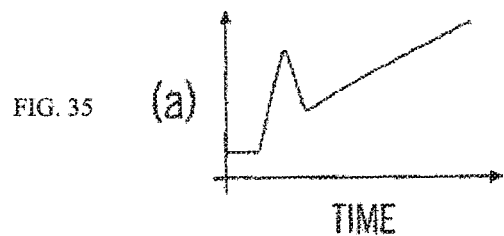
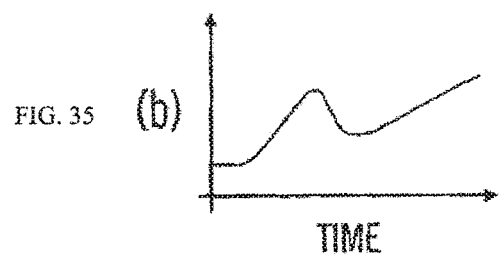
FIG. 35
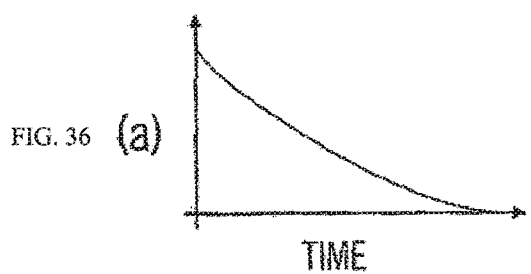
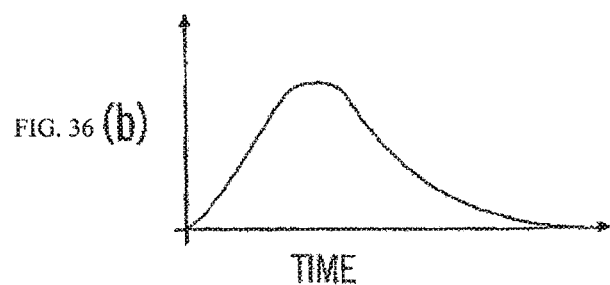
FIG. 36

CLOSED-LOOP GLUCOSE AND/OR INSULIN CONTROL SYSTEM

CROSS REFERENCE TO RELATED APPLICATIONS

This is a divisional of U.S. patent application Ser. No. 12/486,708 filed on Jun. 17, 2009, titled "CLOSED-LOOP GLUCOSE AND/OR INSULIN CONTROL SYSTEM," assigned to the assignee of claimed subject matter and incorporated herein by reference in its entirety.

BACKGROUND

1. Field

Subject matter disclosed herein relates to monitoring and/or controlling blood-glucose levels in patients.

2. Information

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if .β-cells produce insufficient quantities of insulin, Type II diabetes), then insulin must be provided to the body from another source.

Traditionally, since insulin cannot be taken orally, insulin has been injected with a syringe. More recently, use of infusion pump therapy has been increasing, especially for delivering insulin to diabetics. For example, external infusion pumps are worn on a belt, in a pocket, or the like, and deliver insulin into the body via an infusion tube with a percutaneous needle or a cannula placed in the subcutaneous tissue. As of 1995, less than 5% of Type I diabetics in the United States were using infusion pump therapy. Presently over 7% of the more than 900,000 Type I diabetics in the U.S. are using infusion pump therapy. And the percentage of Type I diabetics that use an infusion pump is growing at an absolute rate of over 2% each year. Moreover, the number of Type I diabetics is growing at 3% or more per year. In addition, growing numbers of insulin using Type II diabetics are also using infusion pumps. Physicians have recognized that continuous infusion provides greater control of a diabetic's condition, and are also increasingly prescribing it for patients.

A closed-loop infusion pump system may include an infusion pump that is automatically or semi-automatically controlled to infusion insulin at times and in amounts based upon blood glucose measurements obtained from an embedded blood-glucose sensor in real-time. Closed-loop infusion pump systems may also employ delivery of glucose in addition to delivery of insulin for controlling blood-glucose and/or insulin levels in a patient.

SUMMARY

Briefly, one embodiment relates to a method, system and/or apparatus for determining a recommended therapy for a patient derived from signals representative of blood-glucose sensor measurements; and generating a signal to initiate an alarm to an attendant in response to detection of a suggested change in said recommended therapy based, at least in part, on signals representative of subsequent blood-glucose sensor measurements. In particular embodiments, the recommended therapy may comprise infusion of insulin in the patient at a set infusion rate, an infusion of a bolus of glucose and/or a continuous infusion of glucose. In one particular implementation, a size of a bolus of glucose or insulin may be based, at least in part, on the magnitude of at least one PID command associated with a command cycle of a PID controller for use in determining the recommended therapy.

In another embodiment, a blood-glucose level in the patient may be forecasted based on a subsequent command cycle of the PID controller; and determination of the suggested change may commence in the subsequent command cycle based, at least in part, on said forecasted blood-glucose level. For example, the method, system and/or apparatus may be further directed to calculating an insulin infusion rate based, at least in part, on a PID command associated with said subsequent command cycle; and establishing a new insulin infusion rate for said subsequent command cycle as said calculated infusion rate if a difference between an insulin infusion rate in a current command cycle and said calculated infusion rate exceed a predetermined threshold.

In another embodiment, a PID command associated with said subsequent command cycle may be determined; and a rate of insulin infusion for the suggested change in said recommended therapy may determined based, at least in part, on the PID command if said forecasted blood glucose level exceeds a predetermined threshold blood glucose level.

In another implementation, a blood-glucose level in a patient may be forecasted in a subsequent command cycle; and a command for infusion of a bolus of glucose may be selectively provided based, at least in part, on a PID command associated with the subsequent command cycle if said forecasted blood-glucose level does not exceed a threshold blood glucose level.

In another implementation, at least one current PID command may be determined based, at least in part, on blood-glucose sensor measurements processed in a current command cycle; and at least one subsequent PID command may be determined based, at least in part, on blood-glucose sensor measurements processed in a subsequent command cycle. For example, the suggested change in said recommended therapy may be determined based, at least in part, on the at least one subsequent PID command. In another example, at least one component of the at least one subsequent PID command comprises a derivative component, where a blood glucose derivative is determined based, at least in part, on values of blood glucose sensor measurements obtained at times separated by a sample interval; and the sample value is limited to a predetermined minimum sample value. In yet another example, at least one component of the at least one subsequent PID command comprises an integral component, where a difference between an estimated blood glucose and a target blood glucose is integrated over an integration interval; and the integration interval is limited to a predetermined maximum integration interval.

Another embodiment relates to a method, system and/or apparatus for receiving a signal representative of a measurement value entered at an operator interface; and executing instructions on a special purpose computing apparatus to determine a maximum interval to alert an operator following the receipt of signal representative of said measurement value. In one particular implementation, the maximum interval is based, at least in part, on the measurement value.

In another embodiment, instructions on the special purpose computing apparatus may be further executed to determine the maximum interval based, at least in part, on a signal representative of measured rate of change in blood glucose of a patient.

In another embodiment, signals representative of blood glucose sensor measurements may be received from a patient subsequent to receipt of the signal representative of said measurement value, and instructions on the special purpose computing apparatus may be further executed to determine one or more PID commands based, at least in part, on the blood glucose sensor measurements; and determine the maximum interval based, at least in part, on the one or more PID commands.

In another embodiment, instructions on the special purpose computing apparatus may be further executed determine the maximum interval based, at least in part, on whether a glucose bolus was infused to a patient contemporaneously with receipt of the signal representative of said measurement.

In yet another embodiment, instructions on the special purpose computing apparatus may be further executed to determine the maximum interval based, at least in part, on one or more signals representative of a measured rate of change in blood glucose of a patient.

In yet another embodiment, the entered measurement value may comprise a blood glucose sample measurement value.

Another embodiment relates to a method, system and/or apparatus for a method directed to determining a function for estimating a blood-glucose concentration based, at least in part, on one or more signals representative of a plurality of blood-glucose reference measurements; and selectively determining a y-intercept offset of said function as either a predetermined constant or a calculated value, the calculated value being determined based, at least in part, on a relationship between at least one blood-glucose reference measurement and one or more signals representative of at least one sensor measurement value. The function is to determine estimates of said blood-glucose concentration based on sensor signal values In one particular embodiment, the y-intercept may be selectively determined as either said predetermined constant or calculated value based, at least in part, on a number of blood-glucose reference measurements obtained over a set time period. In another implementation, the calculated value may be selected as said y-intercept offset if at least one of the following conditions are present: at least one of said blood-glucose reference measurements is in a range of about 80.0 to 150.0 mg/dl; a correlation of blood-glucose reference measurements is at least 0.9; or the difference between maximum and minimum blood-glucose reference samples is at least 50 ml/dl and at least 50% of the minimum blood-glucose reference samples.

Particular embodiments may be directed to an article comprising a storage medium including machine-readable instructions stored thereon which, if executed by a special purpose processor, are directed to enable the special purpose processor to execute at least a portion of the aforementioned method according to one or more of the particular aforementioned implementations. In other particular embodiments, a sensor is adapted to generate one or more signals responsive to a blood glucose concentration in a body while a special purpose processor is adapted to perform the aforementioned method according to one or more of the particular aforementioned implementations based upon the one or more signals generated by the sensor.

In yet another embodiment, an apparatus comprises one or more blood-glucose sensors adapted to be coupled to a patient to obtain blood-glucose sensor measurements; and a controller coupled to the one or more blood-glucose sensors to receive one or more signals representative of said blood-glucose sensor measurements. The controller is adapted to determine a recommended therapy for a patient derived from blood-glucose sensor measurements; and initiate an alarm to an attendant in response to detection of a suggested change in said recommended therapy based, at least in part, on subsequent blood-glucose sensor measurements obtained from said blood-glucose sensor.

In yet another embodiment, an apparatus comprises an operator interface to receive an operator entered measurement value; and a controller to determine a maximum interval to alert said operator following said receipt of said measurement value.

In yet another embodiment, an apparatus comprises one or more blood-glucose sensors coupled to a patient to obtain blood-glucose sensor measurements; and a controller coupled to the one or more blood-glucose sensors to receive signals representative of said blood-glucose sensor measurements. The controller is further adapted to determine a function for estimating a blood-glucose concentration in said patient based, at least in part, on a plurality of blood-glucose reference measurements; and selectively determine a y-intercept offset of said function as either a predetermined constant or a calculated value, said calculated value being determined based, at least in part, on a relationship between at least one blood-glucose reference measurement and at least one sensor signal value. Here, the function is to determine estimates of said blood-glucose concentration based on said received signals, said received signals comprising sensor signal values.

BRIEF DESCRIPTION OF THE FIGURES

Non-limiting and non-exhaustive features will be described with reference to the following figures, wherein like reference numerals refer to like parts throughout the various figures.

FIG. 12 is a circuit diagram of an I-F A/D converter of FIG. 10 accompanied by charts of node signals in accordance with an embodiment.

FIG. 13 is another circuit diagram of an I-F A/D converter of FIG. 10 accompanied by charts of node signals in accordance with an embodiment.

FIG. 14 is still another circuit diagram of an I-F A/D converter of FIG. 10 accompanied by charts of node signals in accordance with an embodiment.

FIG. 19(a) is a plot of a filtered and an unfiltered sensor signal over time in accordance with an embodiment.

FIG. 19(b) is close up of a section of the plot of FIG. 19(a) in accordance with an embodiment.

FIG. 25(a) is a plot of insulin responses to a glucose clamp for exercise trained and normal individuals.

FIG. 25(b) is a bar chart of glucose uptake rates for exercise trained and normal individuals.

FIG. 31(a) is a representative drawing of blood glucose compared to sensor measured blood glucose over time in accordance with an embodiment.

FIG. 31(b) is a representative plot of sensor sensitivity over the same period of time as shown in FIG. 31(a) in accordance with an embodiment.

FIG. 31(c) is a representative drawing of sensor resistance over the same period of time as shown in FIG. 31(a) in accordance with an embodiment.

FIG. 34(a) is a bottom view of a telemetered characteristic monitor in accordance with an embodiment.

FIG. 34(b) is a bottom view of a different telemetered characteristic monitor in accordance with an embodiment.

FIG. 35(a) is a plot of a blood plasma insulin response to a glucose clamp in a normal glucose tolerant (NGT) individual in accordance with an embodiment.

FIG. 35(b) is a plot of a blood plasma insulin response of FIG. 35(a) when delayed due to insulin being delivered to the subcutaneous tissue instead of directly into the blood stream in accordance with an embodiment.

FIG. 36(a) is a plot of blood plasma insulin concentration over time after an insulin bolus is delivered directly into the blood stream in accordance with an embodiment.

FIG. 36(b) is a plot of a blood plasma insulin concentration over time after an insulin bolus is delivered into the subcutaneous tissue in accordance with an embodiment.

DETAILED DESCRIPTION

Figure 1:
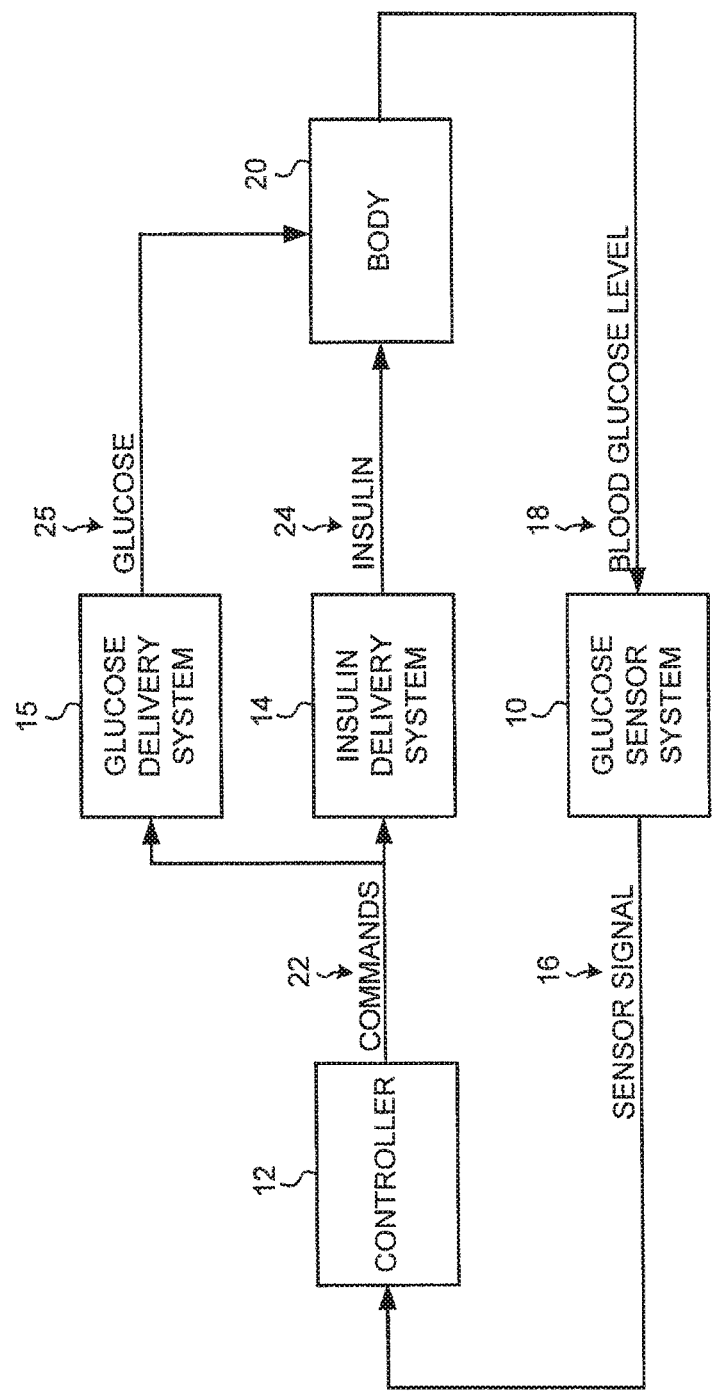
FIG. 1 is a block diagram of a closed loop glucose control system in accordance with one embodiment.

In one implementation, blood-glucose measurements are employed in a closed loop infusion system for regulating a rate of fluid infusion into a body. In particular embodiments, a control system is adapted to regulate a rate of insulin and/or glucose infusion into the body of a patient based, at least in part, on a glucose concentration measurement taken from the body (e.g., from a blood-glucose sensor). In particular implementations, such a system is designed to model a pancreatic beta cell (β-cell). Here, such a system may control an infusion device to release insulin into a body of a patient in a similar concentration profile as would be created by fully functioning human β-cells if responding to changes in blood glucose concentrations in the body.

Thus, such a closed loop infusion system may simulate a body's natural insulin response to blood glucose levels and, not only make efficient use of insulin, but also account for other bodily functions as well since insulin has both metabolic and mitogenic effects.

According to an embodiment, embodiments of a closed-loop system as described herein may be implemented in a hospital environment to monitor and/or control levels of glucose and/or insulin in a patient. Here, as part of a hospital procedure, a caretaker or attendant may be tasked with interacting with the closed-loop system to, for example, enter blood-glucose reference measurements into control equipment to calibrate blood glucose measurements obtained from blood-glucose sensors, making manual adjustments to devices and/or making changes to therapies, just to name a few examples. While there is a desire to have an attendant or caretaker interact with a closed loop system often to reduce risks to a patient's health, there is also a desire to reduce the use of such an attendant or caretaker resource for any particular patient, freeing up the attendant or caretaker for other tasks.

In one embodiment, a closed loop system may determine a recommended therapy, such as the infusion of insulin or glucose, for a patient based, at least in part, on blood-glucose sensor measurements. If subsequently obtained blood-glucose measurements suggest that the recommended therapy should be changed, an alarm message may be transmitted to an attendant or caretaker. Upon receiving the alarm message, the attendant may interact with the closed loop system to, for example, assess the actual need for the suggested change in the recommended therapy and/or implement the suggested change.

In another embodiment, a closed loop system may receive blood-glucose reference measurements from time to time from an operator to, for example, calibrate measurements from a blood glucose sensor. Following such entry of a blood glucose reference sample, an alarm message may be transmitted to an attendant or caretaker if particular events and/or conditions occur. In one particular implementation, a maximum duration (following entry of a blood-glucose reference sample) to alert an attendant or caretaker may be determined based, at least in part, on one or more conditions existing when the sample is entered.

In yet another embodiment, blood glucose measurements from a blood glucose sensor in a closed-loop system may, from time-to-time, be calibrated based, at least in part, on blood-glucose reference samples obtained from a patient. Such a calibration may include determining a function for estimating a blood-glucose concentration from sensor signal values obtained from the blood glucose sensor. In one particular implementation, such a function may be determined based, at least in part, on a plurality of blood-glucose reference measurements. Also, a y-intercept offset of the function may be selected as either a predetermined constant or a calculated value, where the calculated value is determined based, at least in part, on a relationship between at least one blood-glucose reference measurement and at least one sensor signal value. Here, under certain conditions, determination of such a y-intercept offset as a calculated value may produce an unreliable or inaccurate function. Under such conditions, selection of a predetermined constant instead may produce a more reliable or accurate function.

Particular embodiments include a glucose sensor system 10, a controller 12, an insulin delivery system 14 and a glucose delivery system 15, as shown in FIG. 1. Glucose sensor system 10 generates a sensor signal 16 representative of blood glucose levels 18 in body 20, and provides sensor signal 16 to controller 12. Controller 12 receives sensor signal 16 and generates commands 22 that are communicated to insulin delivery system 14 and/or glucose delivery system 15. Insulin delivery system 14 receives commands 22 and may infuse insulin 24 into body 20 in response to commands 22. Likewise, Glucose delivery system 15 receives commands 22 and may infuse glucose 25 into body 20 in response to commands 22.

Glucose sensor system 10 includes a glucose sensor, sensor electrical components to provide power to sensor and generate the sensor signal 16, a sensor communication system to carry sensor signal 16 to controller 12, and a sensor system housing for the electrical components and the sensor communication system.

Controller 12 may include electrical components and software to generate commands for the insulin delivery system 14 and/or glucose delivery system 15 based on sensor signal 16, and a controller communication system to receive sensor signal 16 and carry commands to insulin delivery system 14 and/or glucose delivery system 15. In particular implementations, controller 12 may include a user interface and/or operator interface (not shown) comprising a data input device and/or a data output device. For example, such a data output device may generate signals to initiate an alarm, or a display or printer for showing status of the controller 12 and/or a patient's vital indicators. Such a data input device may comprise dials, buttons, pointing devices, manual switches, alphanumeric keys and/or the like for receiving user and/or operator inputs. It should be understood, however, that these are merely examples of an input and output devices that may be a part of an operator and/or user interface, and that claimed subject matter is not limited in this respect.

Insulin delivery system 14 may include an infusion device and an infusion tube to infuse insulin 24 into body 20. Similarly, glucose delivery system 15 may include an infusion device and an infusion tube to infuse glucose 25 into body 20. In alternative embodiments, insulin 24 and glucose 25 may be infused into body 20 using a shared infusion tube. In yet another alternative embodiment, insulin 24 and glucose 25 may be infused using an intravenous system for providing fluids to a patient in a hospital environment.

In particular embodiments, an infusion device includes infusion electrical components to activate an infusion motor according to commands 22, an infusion communication system to receive commands 22 from controller 12, and an infusion device housing (not shown) to hold the infusion device.

In particular embodiments, controller 12 may be housed in an infusion device housing, and an infusion communication system may comprise an electrical trace or a wire that carries commands 22 from controller 12 to the infusion device. In alternative embodiments, controller 12 may be housed in a sensor system housing and the sensor communication system may comprise an electrical trace or a wire that carries the sensor signal 16 from sensor electrical components to controller electrical components. In other alternative embodiments, controller 12 has its own housing or is included in a supplemental device. In another alternative embodiment, controller 12 is located with an infusion device and a sensor system all within one housing. In further alternative embodiments, the sensor, controller, and/or infusion communication systems may utilize a cable, a wire, fiber optic lines, RF, IR, or ultrasonic transmitters and receivers, and/or the like instead of electrical traces.

System Overview

Figure 2:
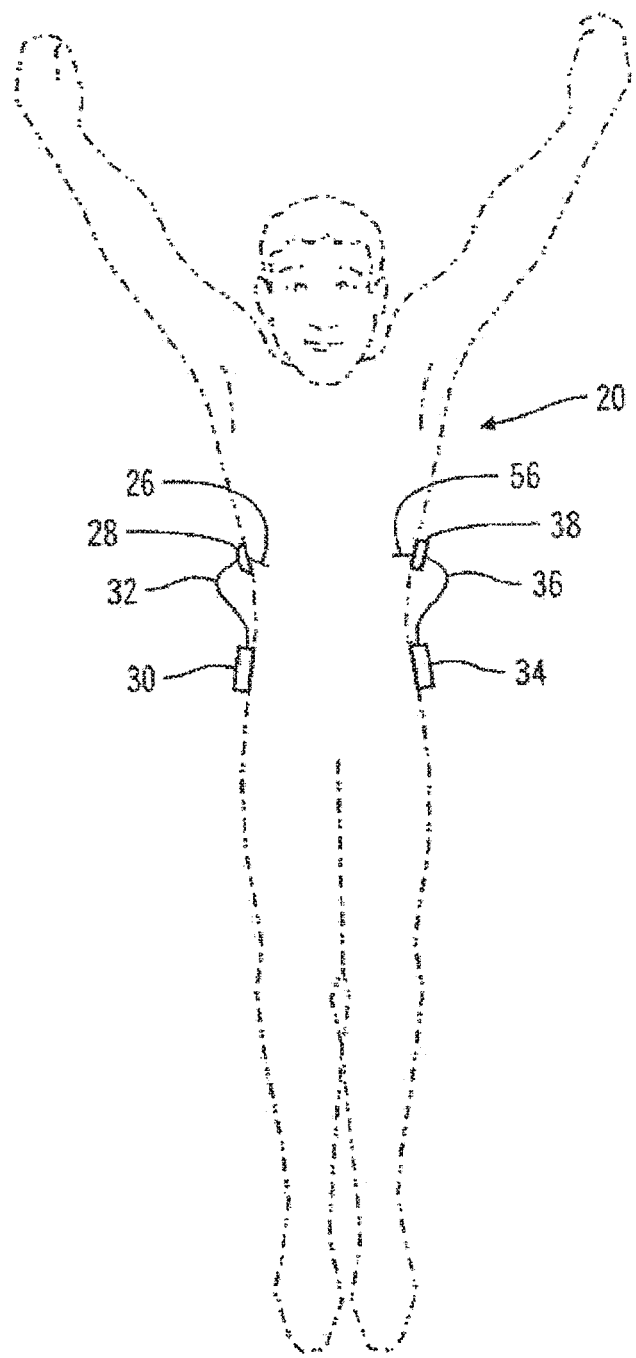
FIG. 2 is a front view of closed loop hardware located on a body in accordance with an embodiment.
Figure 3:
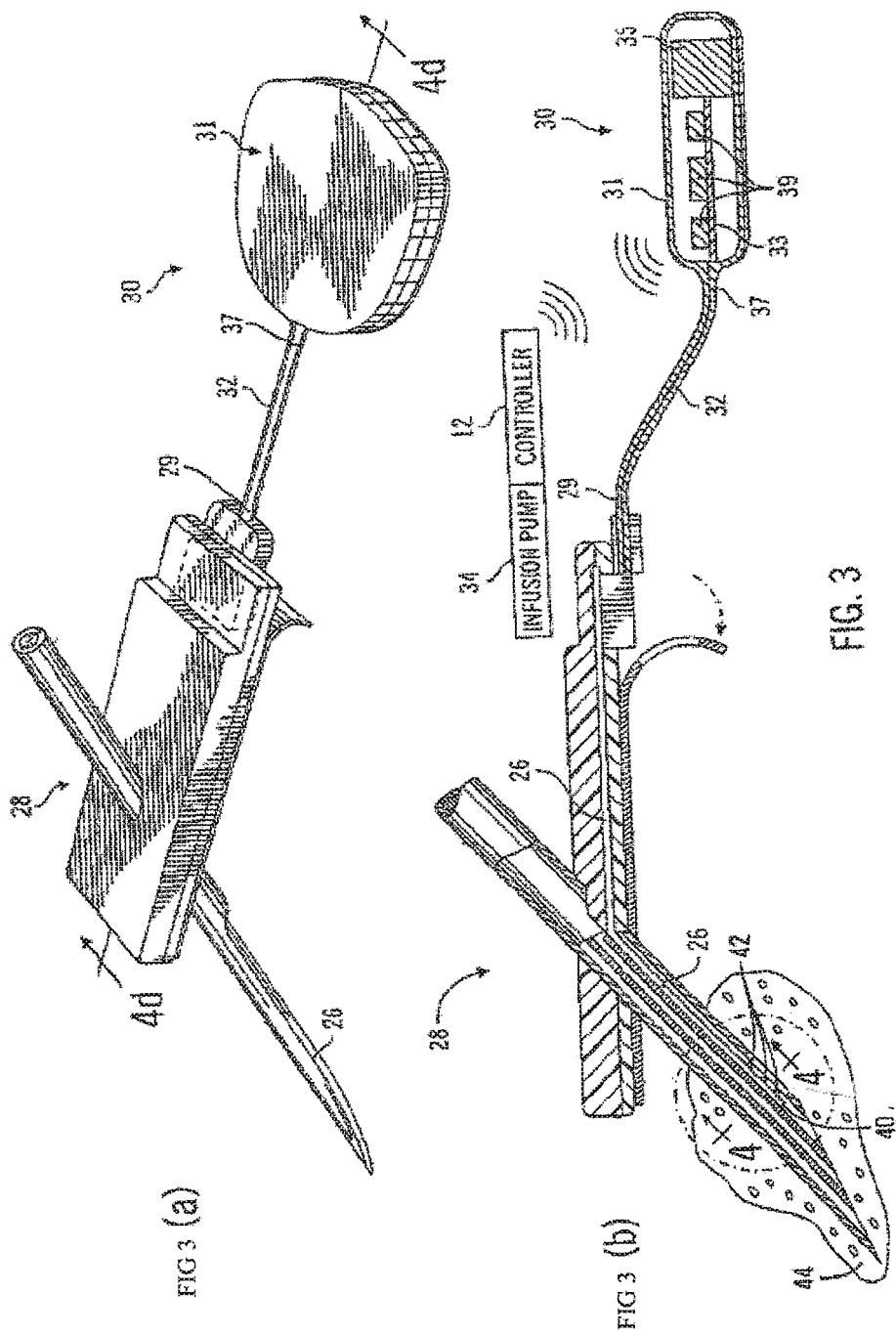
FIG. 3(a) is a perspective view of a glucose sensor system for use in an embodiment.
FIG. 3(b) is a side cross-sectional view of the glucose sensor system of FIG. 3(a).
FIG. 3(c) is a perspective view of a sensor set of the glucose sensor system of FIG. 3(a) for use in an embodiment.
FIG. 3(d) is a side cross-sectional view of the sensor set of FIG. 3(c).
Figure 4:
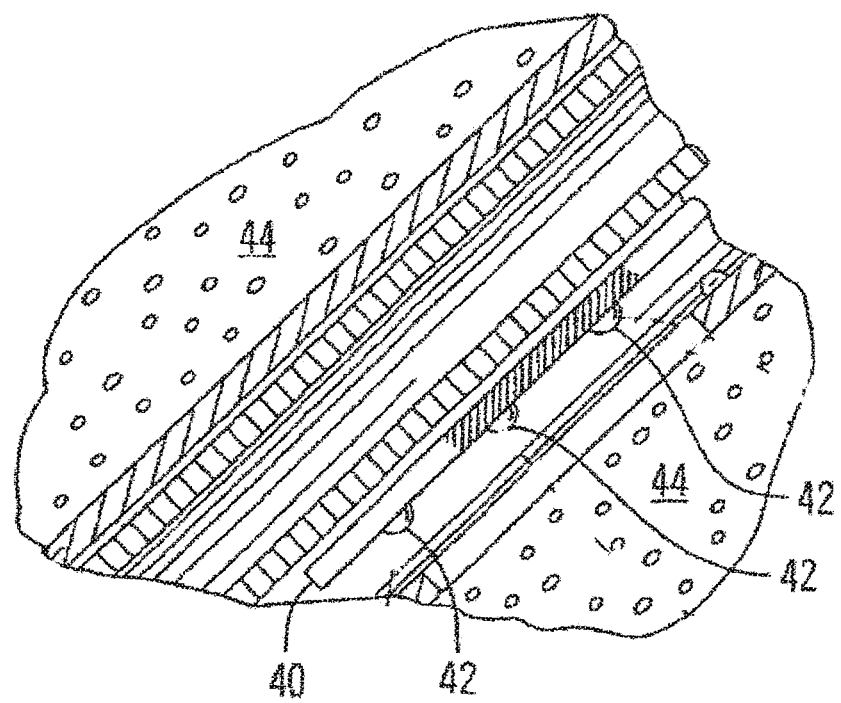
FIG. 4 is a cross sectional view of a sensing end of the sensor of FIG. 3(d).

Particular embodiments may include a sensor 26, a sensor set 28, a telemetered characteristic monitor 30, a sensor cable 32, an infusion device 34, an infusion tube 36, and an infusion set 38, all worn on the body 20 of a user or patient, as shown in FIG. 2. Telemetered characteristic monitor 30 includes a monitor housing 31 that supports a printed circuit board 33, batteries 35, antenna (not shown), and a sensor cable connector (not shown), as seen in FIGS. 3(*a*) and 3(*b*). A sensing end 40 of the sensor 26 has exposed electrodes 42 and is inserted through skin 46 into a subcutaneous tissue 44 of a user's body 20, as shown in FIGS. 3(*d*) and 4. Electrodes 42 are in contact with interstitial fluid (ISF) that is present throughout subcutaneous tissue 44. Sensor 26 is held in place by sensor set 28, which is adhesively secured to the user's skin 46, as shown in FIGS. 3(*c*) and 3(*d*). Sensor set 28 provides for a connector end 27 of sensor 26 to connect to a first end 29 of sensor cable 32. A second end 37 of sensor cable 32 connects to monitor housing 31. Batteries 35 included in monitor housing 31 provide power for sensor 26 and electrical components 39 on printed circuit board 33. Electrical components 39-sample sensor signal 16 and store digital sensor values (Dsig) in a memory and then periodically transmit the digital sensor values Dsig from the memory to controller 12, which is included in the infusion device.

Figure 5:
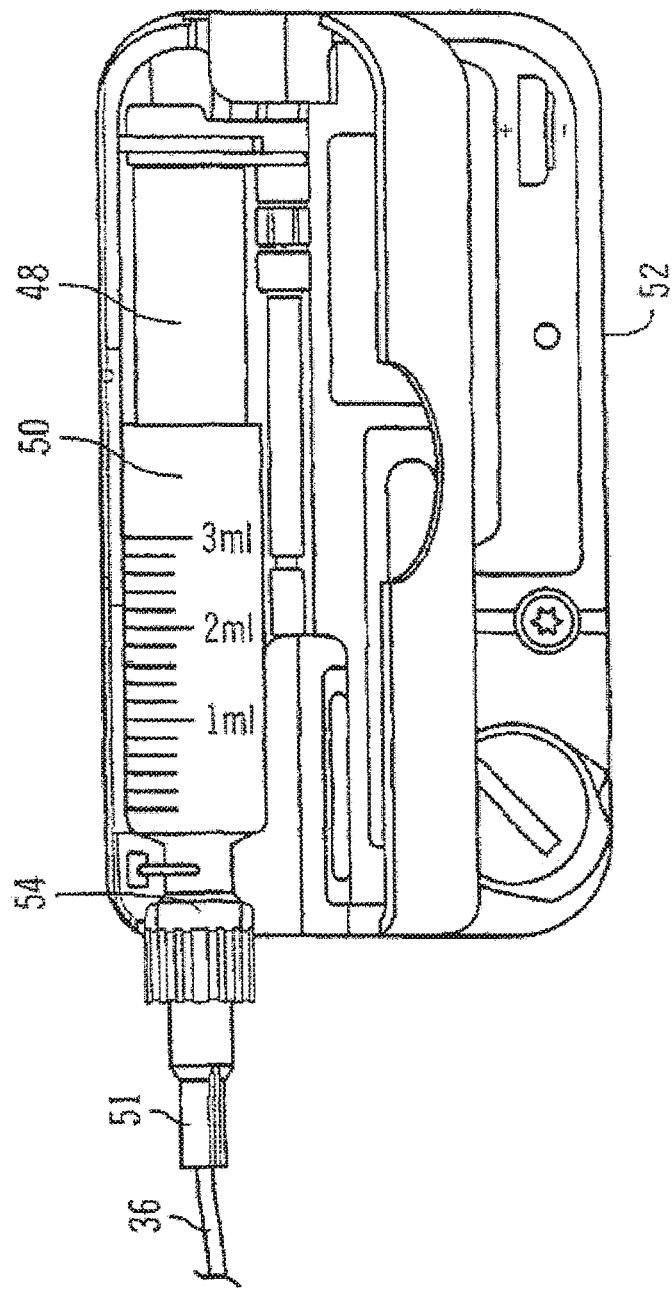
FIG. 5 is a top view of an infusion device with a reservoir door in the open position, for use according to an embodiment.

Controller 12 processes the digital sensor values Dsig and generates commands 22 for infusion device 34. Infusion device 34 may respond to commands 22 and actuate a plunger 48 that forces insulin 24 out of a reservoir 50 located inside the infusion device 34, as shown in FIG. 5. Glucose may be infused from a reservoir responsive to commands 22 using a similar device (not shown). In alternative implementations, glucose may be administered to a patient orally.

Figure 6:
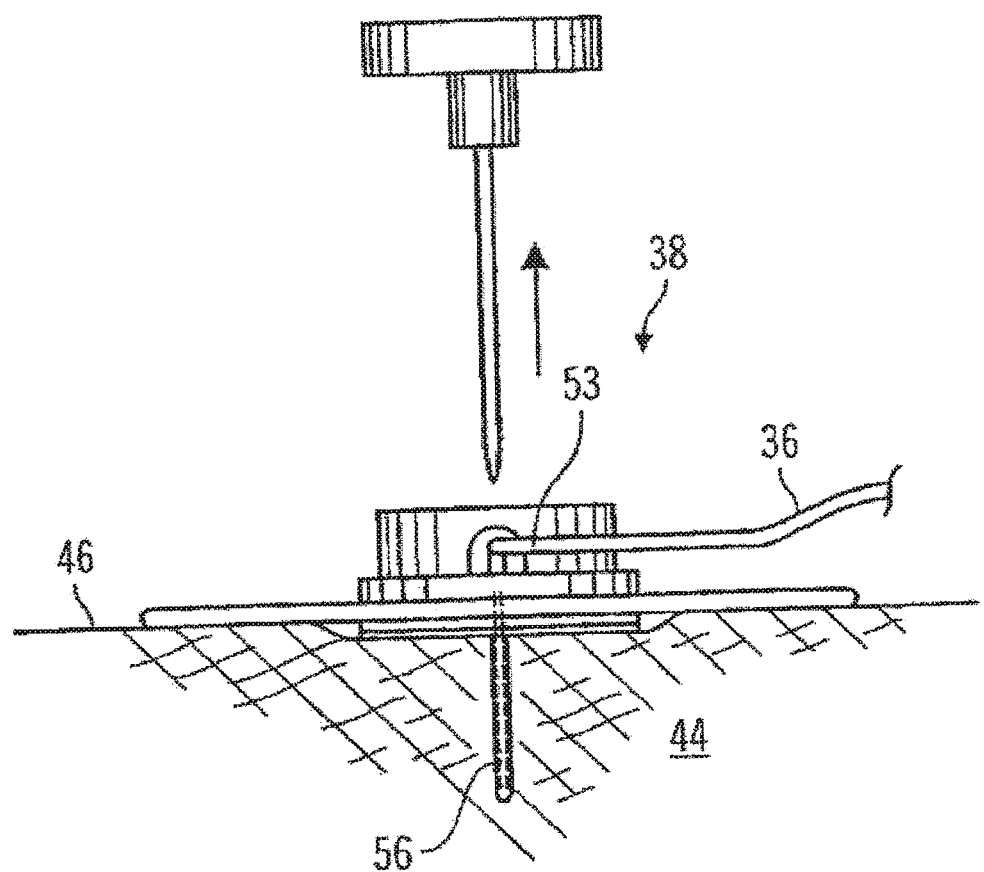
FIG. 6 is a side view of an infusion set with the insertion needle pulled out, for use in an embodiment.
Figure 7:
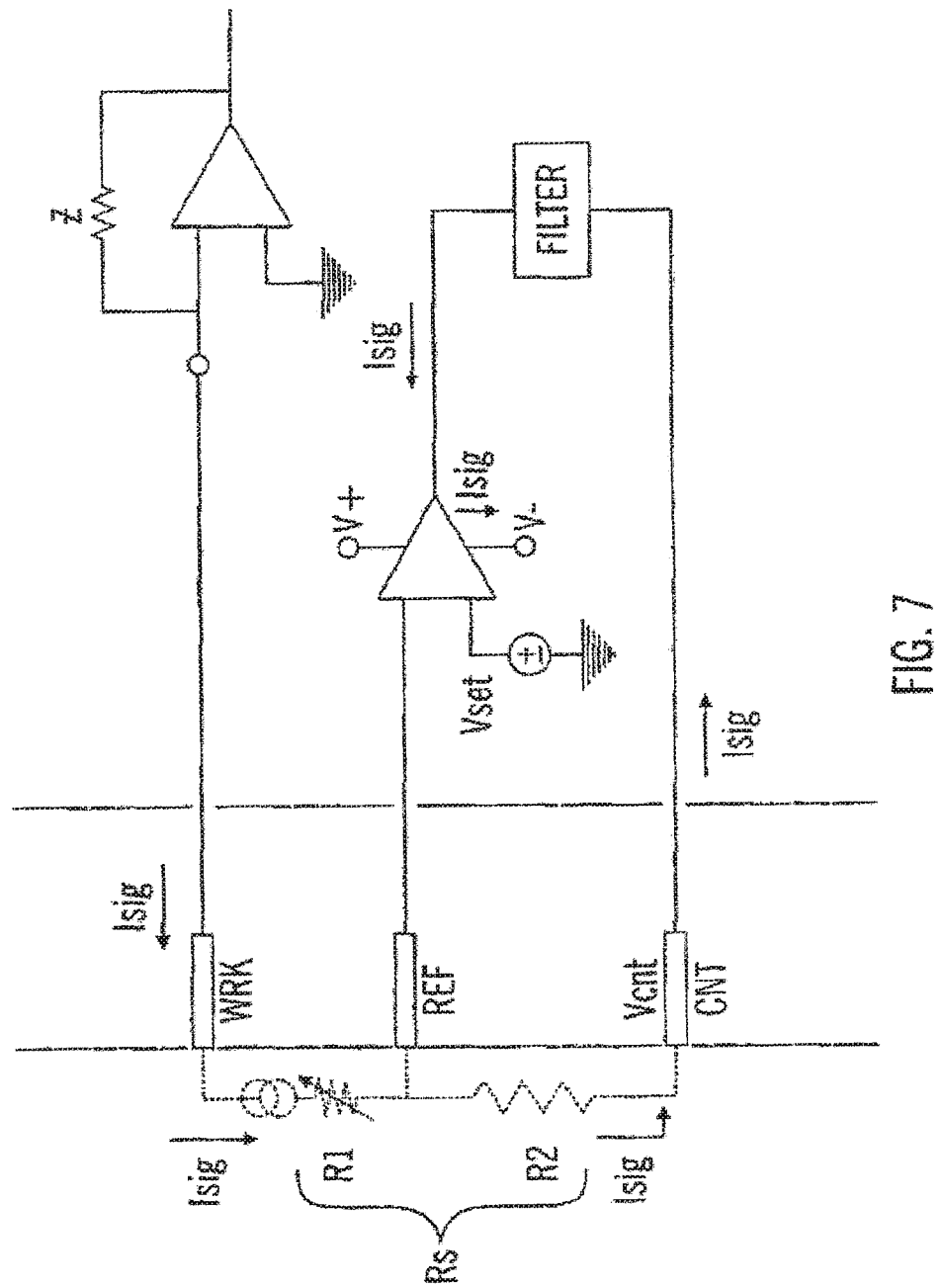
FIG. 7 is a circuit diagram of a sensor and its power supply in accordance with an embodiment.

In particular embodiments, a connector tip 54 of reservoir 50 extends through infusion device housing 52 and a first end 51 of infusion tube 36 is attached to connector tip 54. A second end 53 of infusion tube 36 connects to infusion set 38. Insulin 24 is forced through infusion tube 36 into infusion set 38 and into body 16. Infusion set 38 is adhesively attached to the user's skin 46, as shown in FIG. 6. As part of infusion set 38, a cannula 56 extends through skin 46 and terminates in subcutaneous tissue 44 completing fluid communication between the reservoir 50 and subcutaneous tissue 44 of the user's body 16.

In alternative embodiments, as pointed out above, a closed-loop system in particular implementations can be a part of a hospital-based glucose management system. Given that insulin therapy during intensive care has been shown to dramatically improve wound healing, reduce blood stream infections, renal failure, and polyneuropathy mortality, irrespective of whether subjects previously had diabetes (See Van den Berghe G. et al. NEJM 345: 1359-67, 2001), particular implementations can be used in a hospital setting to control the blood glucose level of a patient in intensive care. In these alternative embodiments, since an intravenous (IV) hookup may be implanted into a patient's arm while the patient is in an intensive care setting (e.g., ICU), a closed loop glucose control can be established which piggy-backs off the existing IV connection. Thus, in a hospital based system, IV catheters which are directly connected to a patient vascular system for purposes of quickly delivering IV fluids, can also be used to facilitate blood sampling and direct infusion of substances (e.g. insulin, glucose, anticoagulants) into the intra-vascular space. Moreover, glucose sensors may be inserted through the IV line to give real-time glucose levels from the blood stream. Therefore, depending on the type of hospital-based system, the alternative embodiments would not necessarily need the described system components such as the sensor 26, the sensor set 28, the telemetered characteristic monitor 30, the sensor cable 32, the infusion tube 36, and the infusion set 38—Instead, standard blood glucose meters or vascular glucose sensors as described in co-pending U.S. patent application Ser. No. 12/121,647, filed May 15, 2008, can be used to provide the blood glucose values to the infusion pump control and the existing IV connection can be used to administer the insulin to the patient.

Figure 39A:
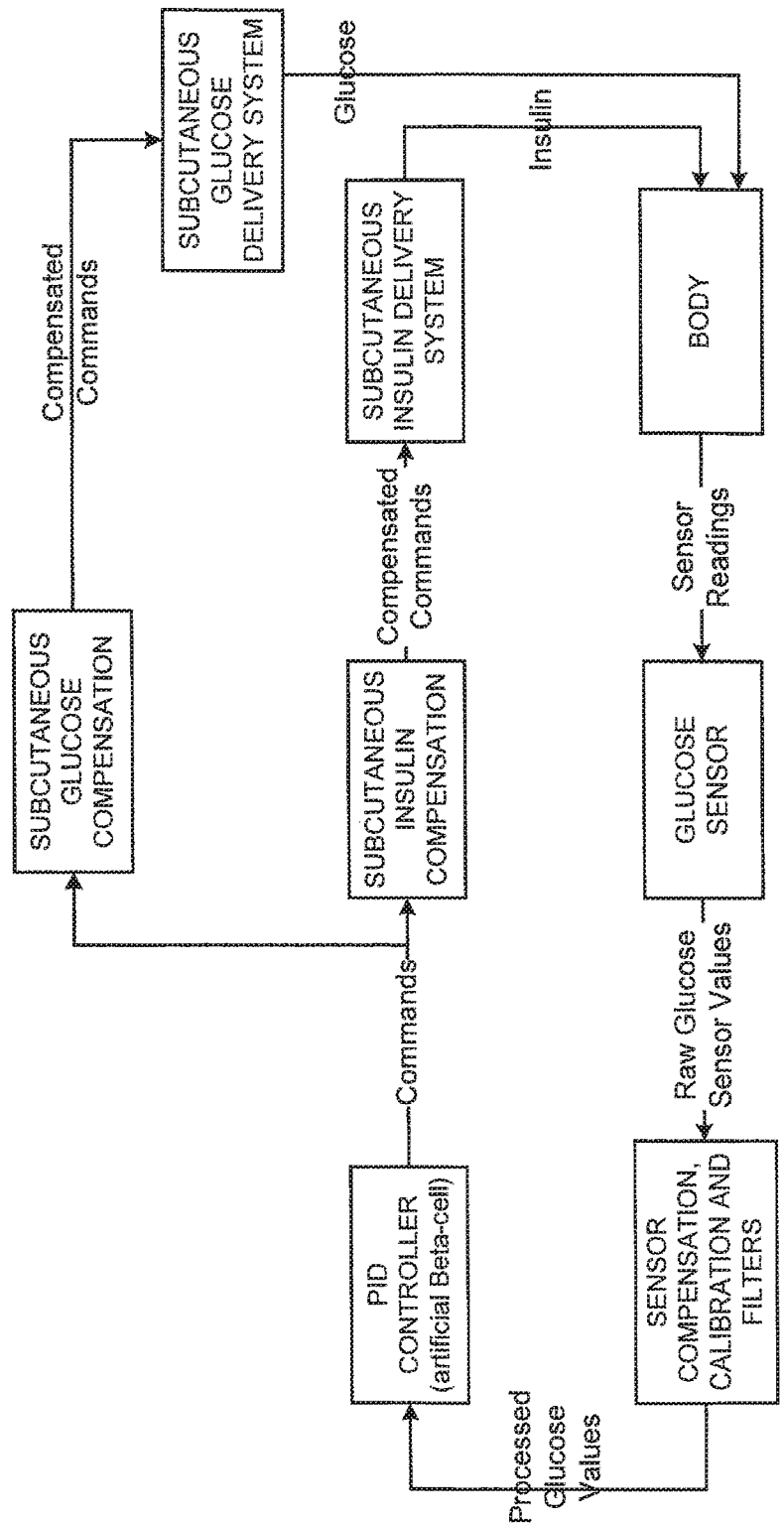
FIGS. 39(a) and (b) are a block diagrams of a closed loop glucose control system in accordance with embodiments.
Figure 39B:
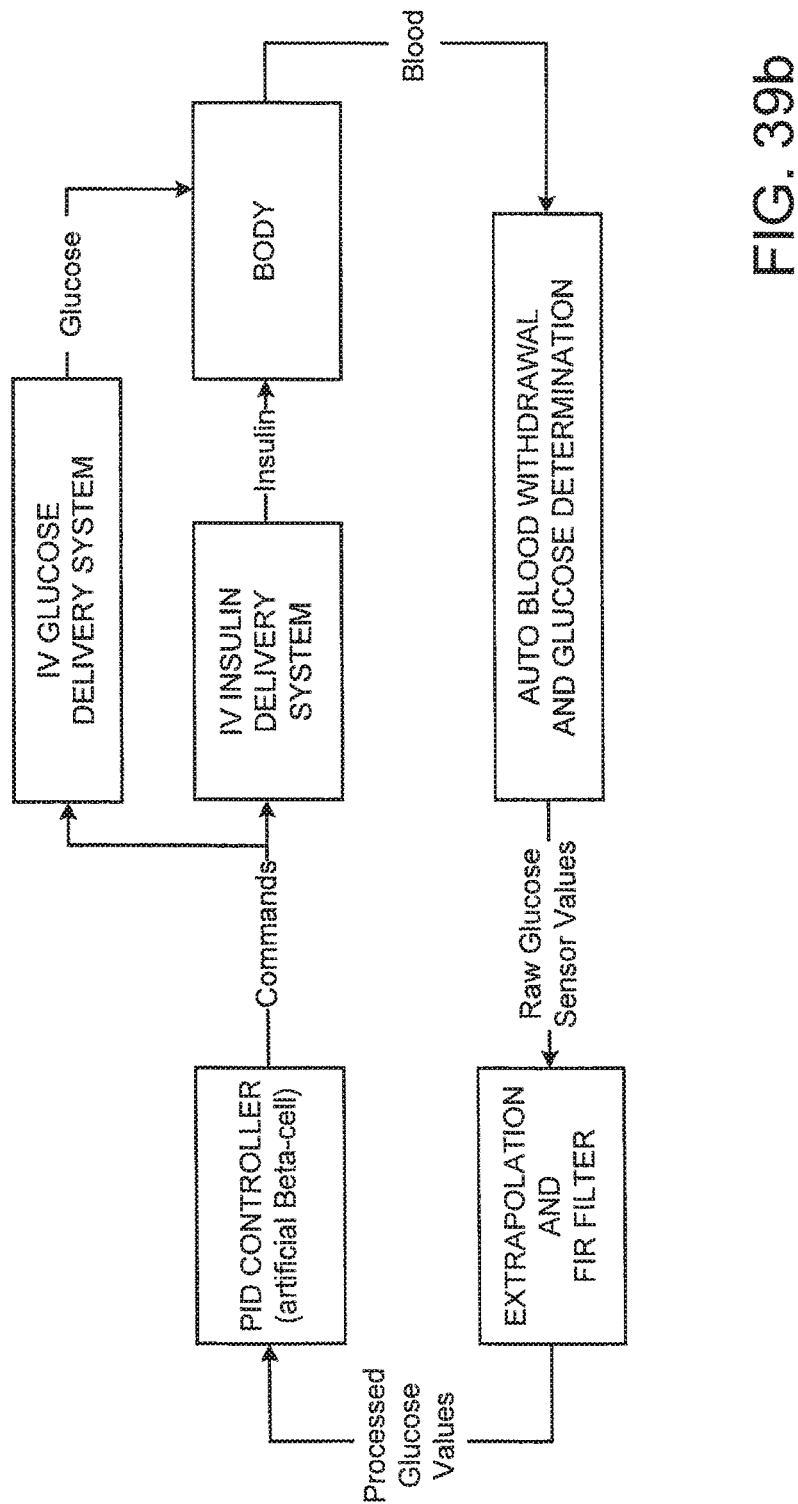
Figure 40:
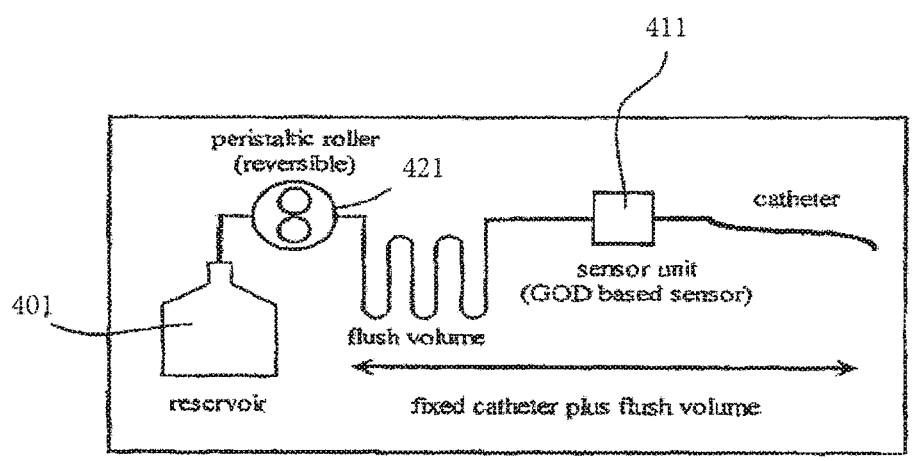
FIG. 40 is a block diagram illustrating auto blood withdrawal and return in accordance with an embodiment.

It is important to appreciate that numerous combinations of devices in the hospital-based system can be used with a closed loop controller as described herein. For example, an auto blood glucose/intravenous insulin infusion system can automatically withdraw and analyze blood for glucose concentration at fixed intervals (e.g., 5-20 minutes), extrapolate blood glucose values at a more frequent interval (e.g., one minute), and use the extrapolated signal for calculating an IV-insulin and/or glucose infusion according to a controller. It is important to appreciate that numerous combinations of devices in the hospital-based system can be used with a closed loop controller according to particular embodiments. For example, as described in FIG. 39*b* compared to the system shown in FIG. 39*a*, an auto blood glucose/intravenous insulin and/or glucose infusion system can automatically withdraw and analyze blood for glucose concentration at fixed intervals (e.g., 5-20 minutes), extrapolate the blood glucose values at a more frequent interval (e.g., one minute), and use the extrapolated signal for calculating an iv-insulin infusion according to the controller described below. The modified auto blood glucose/intravenous insulin infusion system may then eliminate the need for subcutaneous sensor compensation and subcutaneous insulin compensation (as described with regards to a lead-lag compensator below). Such automatic withdrawal of blood, and subsequent glucose determination can be accomplished with existing technology (e.g., VIA, Biostator and/or like blood glucose analyzer) or by the system shown in FIG. 40. Here, the system shown in FIG. 40 uses a peristaltic pump 421 to withdraw blood across an amperometric sensor 411 (e.g., such as that of sensor 26) and then returns the blood with added flush (0.5 to 1.0 ml) from the reservoir 401. Such a flush can consist of any makeup of saline, heparin, glucose solution and/or the like. If the blood samples are obtained at intervals longer than 1.0 minute but less than 20 minutes, the blood glucose determinations can be extrapolated on a minute-to-minute basis with extrapolation based on the present (n) and previous values (n−1) to work with the logic of the controller as described in detail below. For blood samples obtained at intervals greater than 20 minutes, a zero-order-hold may be used for extrapolation. Based on these blood glucose values, an infusion device can administer insulin and/or glucose based, at least in part, on the closed loop controller described below.

In other modifications, a manual blood-glucose/intravenous insulin system can be used where frequent manual entry of blood-glucose values or blood-glucose reference measurements from a standard blood glucose meter (e.g. YSI, Beckman, etc) and extrapolate the values at more frequent intervals (e.g., 1.0 min) to create a surrogate signal for calculating IV insulin infusion. Alternatively, a sensor blood glucose/intravenous insulin system can use a continuous glucose sensor (e.g. vascular, subcutaneous, etc.) for frequent blood glucose measurement. Moreover, insulin can be administered subcutaneously rather than intravenously in any one of the previous examples according to controller embodiments described below.

In still further alternative embodiments, system components may be combined in a smaller or greater number of devices and/or the functions of each device may be allocated differently to suit the needs of the user.

Controller

Once hardware for a closed loop system is configured, as described above, the effects of the hardware on a human body are determined by the controller. In particular embodiments, controller 12 is designed to model a pancreatic beta cell (β-cell). In other words, controller 12 commands infusion device 34 to release insulin 24 into body 20 at a rate that causes the insulin concentration in the blood to follow a similar concentration profile as would be caused by fully functioning human β-cells responding to blood glucose concentrations in the body 20.

A controller that simulates the body's natural insulin response to blood glucose levels not only makes efficient use of insulin but also accounts for other bodily functions as well since insulin has both metabolic and mitogenic effects. Controller algorithms that are designed to minimize glucose excursions in the body without regard for how much insulin is delivered may cause excessive weight gain, hypertension, and atherosclerosis. In particular embodiments, controller 22 is intended to emulate the in vivo insulin secretion pattern and to adjust this pattern to be consistent with in vivo β-cell adaptation. The in vivo β-cell response in subjects with normal glucose tolerance (NGT), with widely varying insulin sensitivity (SI), is the optimal insulin response for the maintenance of glucose homeostasis.

β-Cell and PID Control

Figure 23:
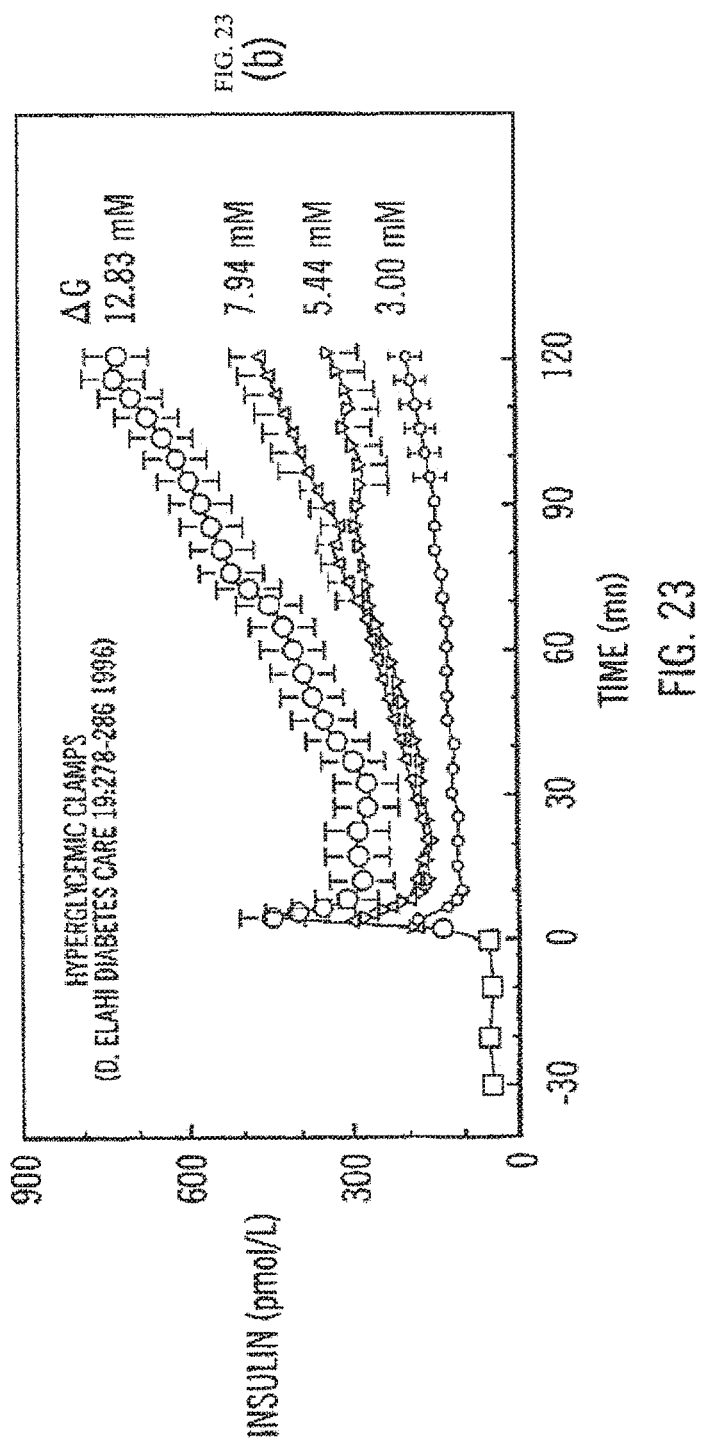
FIG. 23(a) is a diagram of a glucose clamp (glucose level with respect to time).
FIG. 23(b) is a plot of insulin concentration in a normal glucose tolerant (NGT) individual in response to various magnitudes of glucose clamps of FIG. 23(a).

In vivo β-cell response to changes in glucose may be characterized by "first" and "second" phase insulin responses. This biphasic insulin response is clearly seen during hyperglycemic clamps applied to NGT subjects, as shown in FIG. 23(*b*). During a hyperglycemic clamp the glucose level is rapidly increased from a basal level $G_B$ to a new higher level $G_C$ and then held constant at the higher-level $G_C$ as shown in FIG. 23(*a*). The magnitude of the increase in glucose (ΔG) affects the insulin response. Four insulin response curves are shown for four different glucose clamp levels in FIG. 23 (*b*).

According to an embodiment, a biphasic insulin response of a β-cell can be modeled using components of a proportional, plus integral, plus derivative (PID) controller. A PID controller may be selected since PID algorithms are stable for a wide variety of non-medical dynamic systems, and PID algorithms have been found to be stable over widely varying disturbances and changes in system dynamics.

Figure 24:
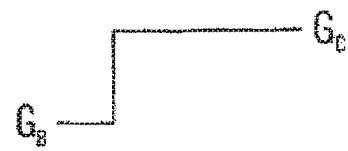
FIG. 24(a) is a diagram illustrating a glucose clamp.
FIG. 24(b) is a diagram of a proportional insulin response to the glucose clamp of FIG. 24(a) in accordance with an embodiment.
FIG. 24(c) is a diagram of an integral insulin response to the glucose clamp of FIG. 24(a) in accordance with an embodiment.
FIG. 24(d) is a diagram of a derivative insulin response to the glucose clamp of FIG. 24(a) in accordance with an embodiment.
FIG. 24(e) is a diagram of a combined proportional, integral, and derivative insulin response to the glucose clamp of FIG. 24(a) in accordance with an embodiment.
Figure 24:
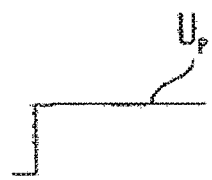
Figure 24:
Figure 24:
Figure 24:
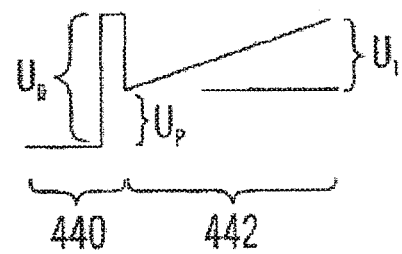

The insulin response of β-cells during a hyperglycemic clamp is diagrammed in FIGS. 24(*a-e*) using the components of a PID controller to model the β-cell. A proportional component $U_P$ and a derivative component $U_D$ of the PID controller may be combined to represent a first phase insulin response 440, which lasts several minutes. An integral component $U_I$ of the PID controller may represent a second phase insulin response 442, which is a steady increase in insulin release under hyperglycemic clamp conditions. The magnitude of each component's contribution to the insulin response is described by the following equations:

Proportional Component Response: $U_P = K_P(G - G_B)$;

Integral Component Response:

$$U_I = K_I \int_{t_0}^{t} (G - G_B) dt + I_B;$$

and

Derivative Component Response:

$$U_D = K_D \frac{dG}{dt}.$$

Where:

$U_P$ is the proportional component of the command sent to the insulin delivery system;

$U_I$ is the integral component of the command sent to the insulin delivery system;

$U_D$ is the derivative component of the command sent to the insulin delivery system;

$K_P$ is a proportional gain coefficient;

$K_I$ is a integral gain coefficient;

$K_D$ is a derivative gain coefficient;

G is a present blood glucose level;

$G_B$ is a desired basal glucose level;

t is the time that has passed since the last sensor calibration;

$t_0$ is the time of the last sensor calibration; and $I_B$ is a basal insulin concentration at $t_0$ or can also be described as $U_I(t_0)$ The combination of the PID components that model the two phases of insulin response by a β-cell is shown in FIG. 24(*e*) as it responds to the hyperglycemic clamp of FIG.

24(a). FIG. 24(e) shows that the magnitude of the first phase response 440 is driven by the derivative and proportional gains, $K_D$ and $K_P$. And the magnitude of the second phase response 442 is driven by the integral gain $K_I$.

According to an embodiment, the aforementioned components of the PID response may be computed at set sample intervals and/or command cycles to provide control commands (e.g., to insulin delivery system 14 and/or glucose delivery system 15). In the expression of the integral component response above, it should be observed that glucose level G is a function of time (t). Here, to address undue effects to the integral component response for extremely long sample intervals and/or command cycles (e.g., one hour or longer), the integration interval $t-t_0$ of the integral component response may be limited to a set maximum integration time. In particular embodiments, such a maximum integration time may be set to a maximum sample interval or maximum duration between consecutive PID commands.

According to an embodiment, the value of $$\frac{dG}{dt}$$

is determined based on consecutive blood glucose samples and/or estimates obtained from a blood glucose sensor (e.g., glucose sensor system 10). For example, the value of $$\frac{dG}{dt}$$

may be estimated based upon the difference between consecutive blood glucose sensor samples divided by the time interval between such samples and/or estimates. In using this particular technique, errors in estimating $$\frac{dG}{dt}$$

may be pronounced if such a time interval between samples and/or estimates is very small. Here, in a particular embodiment, a minimum time interval between samples and/or estimates, for purpose of estimating $$\frac{dG}{dt}$$

may be established to limit the effect of very short time intervals between samples in estimating $$\frac{dG}{dt}.$$

In one alternative implementation, if consecutive blood glucose samples and/or estimates are obtained at times that are apart less than such a minimum time interval, non-consecutive blood glucose samples and/or estimates may be selected for the purpose of estimating $$\frac{dG}{dt}.$$

The components of the PID controller can also be expressed in its discrete form and follows:
Proportional Component Response: $P_{con}{}^n = K_P(SG_f{}^n - G_{sp})$;
Integral Component Response: $I_{con}{}^n = I_{con}{}^{n-1} + K_I(SG_f{}^n - G_{sp})$, $I_{con}{}^0 = I_b$; and
Derivative Component Response: $D_{con}{}^n = K_D dGdt_f{}^n$.

Where $K_P$, $K_I$, and $K_D$ are the proportional, integral, and derivative gain coefficients, respectively, $SG_f$ and $dGdt_f$ are the filtered sensor glucose and derivative respectively, and the superscript n refers to discrete time. In a particular embodiment, a controller may provide one or more "PID commands" on a discrete command cycle n based, at least in part, on the values of $P_{con}{}^n$, $I_{con}{}^n$ and $D_{con}{}^n$. Thus, for a "current" command cycle n, an associated PID command may be based, at least in part, on the values of $P_{con}{}^n$, $I_{con}{}^n$ and $D_{con}{}^n$. Likewise, for a "subsequent" command cycle n+1, an associated command cycle may be based, at least in part, on the values of $P_{con}{}^{n+1}$, $I_{con}{}^{n+1}$ and $D_{con}{}^{n+1}$. In a particular implementation, for example, such a PID command may comprise a combination of $P_{con}{}^n$, $I_{con}{}^n$ and $D_{con}{}^n$ such as $P_{con}{}^n + I_{con}{}^n + D_{con}{}^n$. It should be understood, however that this merely an example of how a PID command may be determined for a particular command cycle and that claimed subject matter is not limited in this respect.

According to an embodiment, an acute insulin response may prevent wide postprandial glycemic excursions. An early insulin response to a sudden increase in glucose level may result in less total insulin being needed to bring the glucose level back to a desired basal glucose level. This is because an infusion of insulin may increase the percentage of glucose that is taken up by the body. Infusing a large amount of insulin to increase the percentage of glucose uptake while the glucose concentration is high may result in an efficient use of insulin. Conversely, infusing a large amount of insulin while the glucose concentration is low results in using a large amount of insulin to remove a relatively small amount of glucose. In other words, a larger percentage of a big number is more than a larger percentage of a small number. The infusion of less total insulin helps to avoid development of insulin resistance in the user. As well, first-phase insulin is thought to result in an early suppression of hepatic glucose output.

Insulin sensitivity is not fixed and can change dramatically in a body depending on the amount of exercise by the body. In one study, for example, insulin responses in highly exercise-trained individuals (individuals who trained more than five days a week) were compared to the insulin responses in subjects with normal glucose tolerance (NGT) during a hyperglycemic clamp. The insulin response in exercise-trained individuals 444 was about ½ of the insulin response of the NGT subjects 446, as shown in FIG. 25(a). But the glucose uptake rate for each of the individuals (exercise-trained 448 or normal 450) was virtually identical, as shown in FIG. 25(b). Thus, it can be speculated that the exercise-trained individuals have twice the insulin sensitivity and half of the insulin response leading to the same glucose uptake as the NGT individuals. Not only is the first phase insulin response 440 reduced due to the effects of exercise, but the second phase insulin response 442 has also been shown to adjust to insulin sensitivity, as can be seen in FIG. 25(a).

Figure 26:
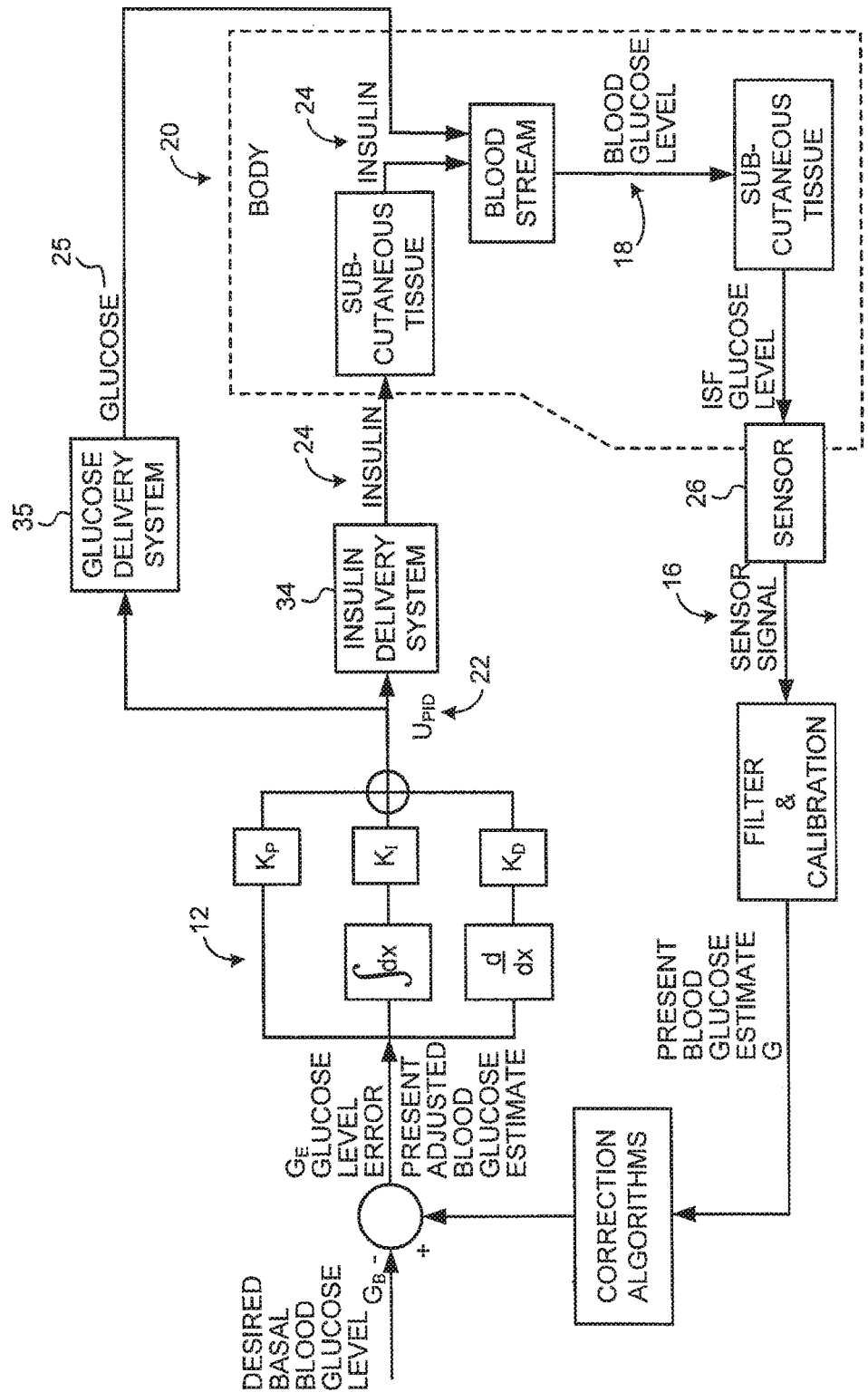
FIG. 26 is a block diagram of a closed loop system to control blood glucose levels through insulin infusion based on glucose level feedback in accordance with an embodiment.

In particular embodiments, a closed loop control system may be used for delivering insulin to a body to compensate for β-cells that perform inadequately. There is a desired basal blood glucose level $G_B$ for a particular body. The difference between the desired basal blood glucose level $G_B$ and an estimate of the present blood glucose level G is the glucose level error $G_E$ that is to be corrected. In a particular embodiment, glucose level error $G_E$ is provided as an input to the controller 12, as shown in FIG. 26.

If the glucose level error $G_E$ is positive (meaning that the present estimate of the blood glucose level G is higher than the desired basal blood glucose level $G_B$) then a command from controller 12 may generate a PID command to drive insulin delivery system 34 to provide insulin 24 to body 20. Likewise, if $G_E$ is negative (meaning that the present estimate of the blood glucose level G is lower than the desired basal blood glucose level $G_B$) then a command from controller 12 may generate a PID command to drive glucose delivery system 35 to provide glucose 25 to body 20. In terms of the control loop, glucose may be considered to be positive, and therefore insulin is negative. Sensor 26 may sense an ISF glucose level and generate a sensor signal 16. Sensor signal 16 is filtered and calibrated to create an estimate of the present blood glucose level. In particular embodiments, an estimate of the present blood glucose level G may be adjusted with correction algorithms before it is compared to the desired basal blood glucose level $G_B$ to calculate a new glucose level error $G_E$ to start the loop again.

If the glucose level error $G_E$ is negative (meaning that the present estimate of the blood glucose level is lower than the desired basal blood glucose level $G_B$) then controller 12 reduces or stops the insulin delivery depending on whether the integral component response of the glucose error $G_E$ is still positive. In alternative embodiments, as discussed below, controller 12 may initiate infusion of glucose 25 if glucose level error $G_E$ is negative.

If the glucose level error $G_E$ is zero, (meaning that the present estimate of the blood glucose level is equal to the desired basal blood glucose level $G_B$) then the controller 12 may or may not issue commands to infuse insulin 24 or glucose 25 depending on the derivative component (whether the glucose level is raising or falling) and the integral component (how long and by how much glucose level has been above or below the basal blood glucose level $G_B$).

To more clearly understand the effects that the body has on the control loop, a more detailed description of the physiological affects that insulin has on the glucose concentration in the interstitial fluid (ISF) is provided. In particular embodiments, infusion delivery system 34 delivers insulin into the ISF of subcutaneous tissue 44 of the body 20. Alternatively, insulin delivery system 34 or a separate infusion device (not shown) may similarly deliver glucose into the ISF of subcutaneous tissue 44. Here, insulin may diffuse from the local ISF surrounding the cannula into the blood plasma and then spread throughout the body 20 in the main circulatory system. Infused insulin may then diffuse from the blood plasma into the interstitial fluid ISF substantially through out the entire body. Here, insulin 24 binds with and activates membrane receptor proteins on cells of body tissues. This facilitates glucose permeation into the activated cells. In this way, the tissues of the body 20 take up the glucose from the ISF. As the ISF glucose level decreases, glucose diffuses from the blood plasma into the ISF to maintain glucose concentration equilibrium. Finally, the glucose in the ISF permeates the sensor membrane and affects the sensor signal 16.

In addition, insulin has direct and indirect affects on liver glucose production. Increased insulin concentration decreases liver glucose production. Therefore, acute and immediate insulin response not only helps the body to efficiently take up glucose but also substantially stops the liver from adding to the glucose in the blood stream. In alternative embodiments, as pointed out above, insulin and/or glucose may be delivered more directly into the blood stream instead of into the interstitial fluid, such as delivery into veins, arteries, the peritoneal cavity, or the like. Accordingly, any time delay associated with moving insulin and/or glucose from the interstitial fluid into the blood plasma is diminished. In other alternative embodiments, the glucose sensor is in contact with blood or body fluids other than interstitial fluid, or the glucose sensor is outside of the body and measures glucose through a non-invasive means. The embodiments that use alternative glucose sensors may have shorter or longer delays between the blood glucose level and the measured blood glucose level.

Selecting Controller Gains

In particular embodiments, controller gains $K_P$, $K_I$, and $K_D$, are selected so that the commands from the controller 12 direct infusion device 34 to release insulin 24 into the body 20 at a rate, that causes the insulin concentration in the blood to follow a similar concentration profile, as would be caused by fully functioning human β-cells responding to blood glucose concentrations in the body. Similarly, controller gains $K_P$, $K_I$, and $K_D$, may be selected so that the commands from the controller 12 direct infusion device 34 to release glucose 25 in response to insulin excursions. In particular embodiments, the gains may be selected by observing the insulin response of several normal glucose tolerant (NGT) individuals, with healthy normally functioning β-cells. A first step in determining a set of controller gains is to take periodic measurements of blood glucose and blood insulin concentrations from the group of NGT individuals. Second, each individual in the group may be subjected to a hyperglycemic clamp, while continuing to periodically measure and record the blood glucose and blood insulin concentrations. Third, a least squares curve fit may be applied to the recorded blood insulin concentrations measured over time for each individual. The result is a set of curves representing the insulin responses to the hyperglycemic clamp for each individual of the group. Fourth, the curves may be used to calculate the controller gains $K_P$, $K_I$, and $K_D$, for each individual. Finally, proportional gains from each of the individuals may be averaged together to obtain an average proportional gain, $K_P$, to be used in controller 12. Similarly, integral gains, $K_I$, and the derivative gains, $K_D$, may be averaged to obtain an average integral gain, $K_I$, and an average derivative gain, $K_D$, for controller 12. Alternatively, other statistical values may be used instead of averages such as, for example, maximums, minimums, the high or low one, two or three sigma standard deviation values, and/or the like. The gains calculated for various individuals in a group may be filtered to remove anomalous data points before statistically calculating the gains to be used in a controller.

Figure 27:
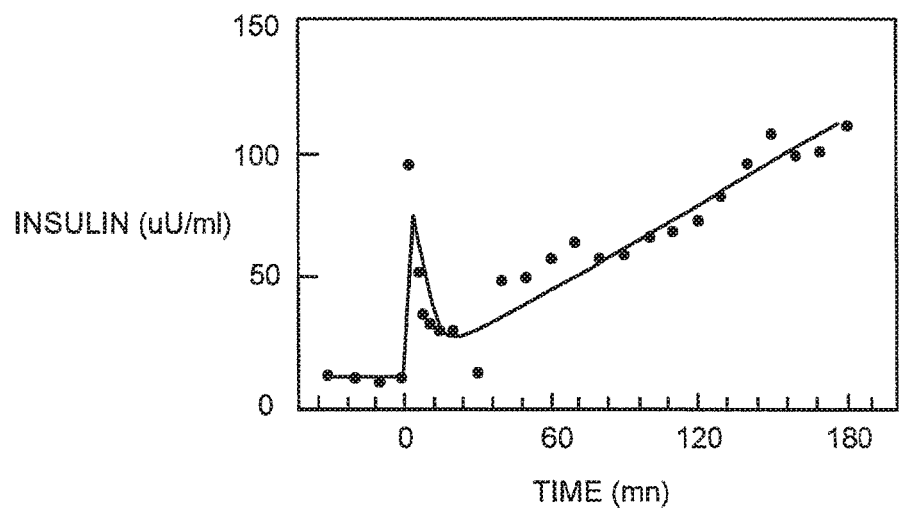
FIGS. 27 and 28 are plots of measured insulin responses of two different normal glucose tolerant (NGT) individuals to a glucose clamp for use with an embodiment.
Figure 28:
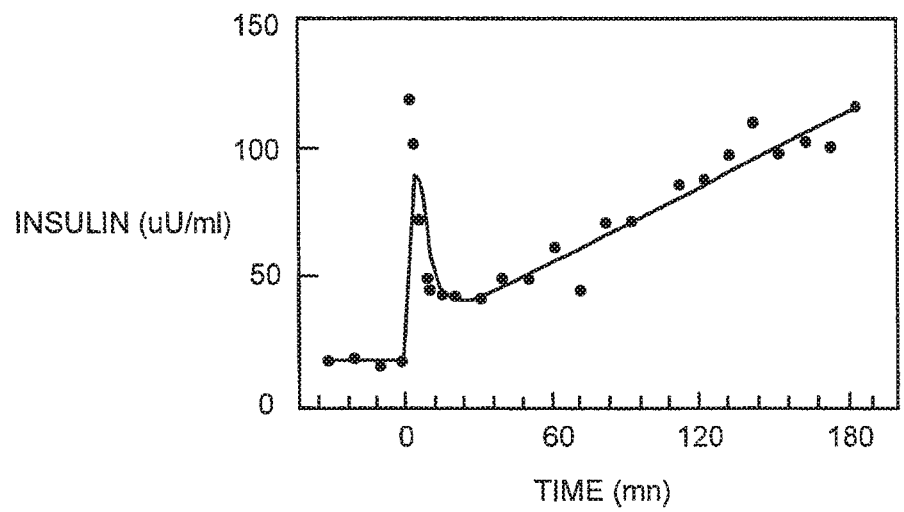

In one particular example, a least squares curve-fitting method was used to generate representative insulin response curves from two fasted individuals in a group, as shown in FIGS. 27 and 28. Then, controller gains were calculated from insulin response curves of the two representative individuals and are shown in Table 1. When calculating the controller gains, the insulin clearance rate (k) was assumed to be 10 (ml of insulin)/min/(kg. of body weight). Here, the insulin clearance rate k is the rate that insulin is taken out of the blood stream in a body. Finally, the average value for each type of gain is calculated using the measurements from the group, as shown in Table 1.

TABLE 1

PID Controller Gains Calculated from the Insulin Response Curves of Two NGT Individuals

| Individuals | Proportional Gain, $K_P$ | Integral Gain, $K_I$ | Derivative Gain, $K_D$ |
|---|---|---|---|
| a | 0.000406 | 0.005650 | 0.052672 |
| b | 0.000723 | 0.003397 | 0.040403 |
| Average | 0.000564 | 0.004523 | 0.046537 |

Controller gains may be expressed in various units and/or may be modified by conversion factors depending on preferences for British or S. I. Units, floating-point or integer software implementation, the software memory available, and/or the like. The set of units for the controller gains for the particular implementation of Table 1 is:

$K_P$: (mU of insulin)/min/(Kg of body weight) per (mg of glucose)/(dl of plasma);

$K_I$: (mU of insulin)/min/(Kg of body weight) per (mg of glucose)/(dl of plasma)/min.; and $K_D$: (mU of insulin)/min/(Kg of body weight) per (mg of glucose)/(dl of plasma)*min.

In alternative embodiments, other curve fitting methods may be used to generate insulin response curves from the measurements of blood insulin concentrations.

An estimate of an insulin clearance rate (k), the individual's body weight (W), and the insulin sensitivity $S_I$ may be used to calculate controller gains from insulin response curves for each NGT individual. The insulin clearance rate (k) may be substantially proportional to body weight and is well documented in literature. An individual's insulin sensitivity $S_I$ may be measured using an intravenous glucose tolerance test, a hyperinsulinemic clamp, or in the case of a diabetic patient, comparing the individual's daily insulin requirement to the individual's daily carbohydrate intake.

In particular embodiments, two parameters, insulin sensitivity $S_I$ and insulin clearance rate k, may be measured for each individual. In other embodiments, an insulin clearance rate k may be estimated from literature given an individual's body weight. In other particular embodiments, longer or shorter insulin clearance times may be used. In still other embodiments, all of the parameters are estimated. In additional embodiments, one or more parameters are measured, while at least one parameter is estimated from literature.

In other alternative embodiments, controller gains may be calculated using a group of individuals with similar body types. For example, an insulin response to a hyperglycemic clamp may be measured for several tall, thin, NGT, males in order to calculate the controller insulin response gains for each individual in the group. Then, gains may be statistically combined to generate a set of representative controller gains for tall, thin, NGT, males. The same could be done for other groups such as, but not limited to, short, heavy, NGT, females; medium height, medium weight, highly exercised trained, females; average height and weight ten year olds; and/or the like. Then, controller gains may be selected for each individual user based on the group that best represents the individual. In further alternative embodiments, controller gains may be uniquely selected for each individual user. In particular embodiments, controller gains for a user may be selected based on measurements of insulin sensitivity, insulin clearing time, insulin appearance time, insulin concentration, body weight, body fat percentage, body metabolism, or other body characteristics such as pregnancy, age, heart conditions, and/or the like.

In other alternative embodiments, the controller gains are estimated as a function of a user's body weight W and insulin sensitivity $S_I$. A series of observations are used to justify this method. In a first observation, controller gains may be proportional to one another. For example, small changes in glucose concentration may cause a small derivative response $U_D$, a small proportional response Up and a small integral response $U_I$. Also, larger changes in glucose concentration cause a proportionally larger derivative response $U_D$, a proportionally larger proportional Up response and a proportionally larger integral response $U_I$, as shown in FIG. 23(b). Changes in glucose concentration may proportionally affect all three components of a controller response $U_{PID}$. In a second observation, a first phase insulin response (φ1) may be proportional to the derivative gain $K_D$. In a third observation, two constants may be readily obtained form information in published literature or may be measured from a cross-section of the general population. The two constants are the insulin clearance rate k for a human given a body weight W and the disposition index (DI) for a human given a change in glucose concentration.

While multiple sources for the information may be used to calculate the insulin clearance rate k, one source is the article "Insulin clearance during hypoglycemia in patients with insulin-dependent diabetes mellitus", written by Kollind M et al., published in Horm Metab Res, 1991 July; 23(7):333-5. Here, the insulin clearance rate k may be obtained from insulin infused divided by the steady state plasma insulin concentration. An insulin clearance constant $A_k$, which is independent of an individual's body weight, may be obtained by dividing the insulin clearance rate k (measured from a particular individual) by the individual's body weight. An insulin clearance constant $A_k$ may be assumed to be about the same for all humans, except under extenuating circumstances such as after an individual has contracted HIV, other metabolic affecting diseases, and/or the like.

The disposition index DI for a human given a change in glucose concentration may be available from information presented in the article "Quantification of the relationship between insulin sensitivity and beta-cell function in human subjects. Evidence for a hyperbolic function", written by Khan S E et al., published in Diabetes, 1993 November; 42(11):1663-72.

Both, the disposition index DI and the insulin clearance rate k may be measured directly from tests. The disposition index DI may be calculated given the first phase insulin response measured form a glucose clamp test and the individual's insulin sensitivity measured from an insulin sensitivity test. The insulin clearance rate k may be measured from an insulin clearance test. The glucose clamp test and the insulin clearance test are described in the above-mentioned articles and are well known in the art. An insulin sensitivity $S_I$ may be measured using an intravenous glucose tolerance test or a hyperinsulinemic clamp test.

Given these observations, then the following parameters may be measured from an NGT individual's insulin response to a glucose clamp: a desired first phase insulin response φ1, the ratio of $K_D$ to $K_P$, and the ratio of $K_D$ to $K_I$. Then the derivative gain $K_D$ may be calculated from the first phase insulin response φ1 using the constants k and DI. Finally $K_P$ and $K_I$ may be calculated using the ratios of $K_D$ to $K_P$ and $K_D$ to $K_I$.

The first phase insulin response φ1 may be observed in a NGT individual as the area under the insulin response curve during approximately the first ten minutes of such a glucose clamp. An increase in glucose concentration during the glucose clamp may be expressed as:

$$\Delta G = (G \times G_B),$$

where G is equal to Gc, the glucose concentration during the clamp, and $G_B$ is the basal glucose concentration before the clamp.

The role of the first phase insulin response φ1 has been emphasized by studies indicating that, in NGT subjects, the product of first phase insulin response φ1 and insulin sensitivity (SI) is a constant known as the disposition index as follows:

$$DI = \varphi 1 S_I.$$

Accordingly, $$\varphi 1 = \frac{DI}{S_I}$$

For a different ΔG there is a different φ1 and therefore a different DI. But, the ratio DI/ΔG may be substantially constant even for different individuals with different insulin sensitivities.

Insulin sensitivity $S_I$ may be defined as the percentage of the glucose concentration that the body tissues will take up for a given amount of insulin. A β-cell may naturally adapt to changes in insulin sensitivity by adjusting an amount of insulin it secretes during the first phase insulin response φ1. This suggests that the body may naturally seek an optimal level of glucose tolerance. A controller that mimics this characteristic of a β-cell may more accurately simulate a body's natural insulin response.

The instantaneous insulin response (RI) may be calculated given the insulin clearance rate (k) and the first phase insulin response φ1, $$R_I = k \varphi 1$$

As pointed out above, an insulin clearance rate k may be proportional to body weight W. Therefore substituting a proportional constant $A_k$ and the user's body weight W for k and replacing φ1 with the ratio of DI over $S_I$ yields the following:

$$R_I = A_k W \frac{DI}{S_I}$$

The instantaneous insulin response $R_I$ may also be expressed as the product of the derivative gain $K_D$ and the change in glucose concentration ΔG as follows:

$$R_I = K_D \Delta G.$$

Setting the two expressions for $R_I$ equal to each other and solving for $K_D$ yields the following:

$$K_D = \frac{W A_k 2 DI}{S_I \Delta G}.$$

As mentioned above, DI/ΔG and $A_k$ may be treated as constants available or calculated from data in published literature. Such constants may be combined and reduced to a single constant, Q, as follows:

$$Q = \frac{A_k DI}{\Delta G}.$$

This may provide an expression for the derivative gain $K_D$ that is a function of the user's body weight W and the user's insulin sensitivity $S_I$ as follows:

$$K_D = \frac{W}{S_I} Q.$$

Here, once derivative gain $K_D$ is determined, proportional and integral gains may be calculated using ratios. A ratio of $K_D/K_P$ can be set to the dominant time constant for insulin action, ranging from 10-60 minutes, but more typically 20-40 minutes (e.g., 30 minutes). For example, calculating $K_P$ given $K_D$ using a time constant of 30 minutes, may provide the following relationship:

$$\frac{K_D}{K_P} = 30 \Rightarrow K_P = \frac{K_D}{30}.$$

In a similar fashion, the ratio of $K_D/K_I$ can be set to the average ratio measured from a population of NGT individuals. Also, $K_I$ can be calculated from $K_D$.

In particular embodiments, an individual may enter a patient's body weight W and insulin sensitivity $S_I$ into a device containing the controller. Controller gains may then be automatically calculated and used by the controller. In alternative embodiments, an individual may enter a patient's body weight W and insulin sensitivity $S_I$ into a device and the device provides the information to the controller to calculate the gains.

Figure 29:
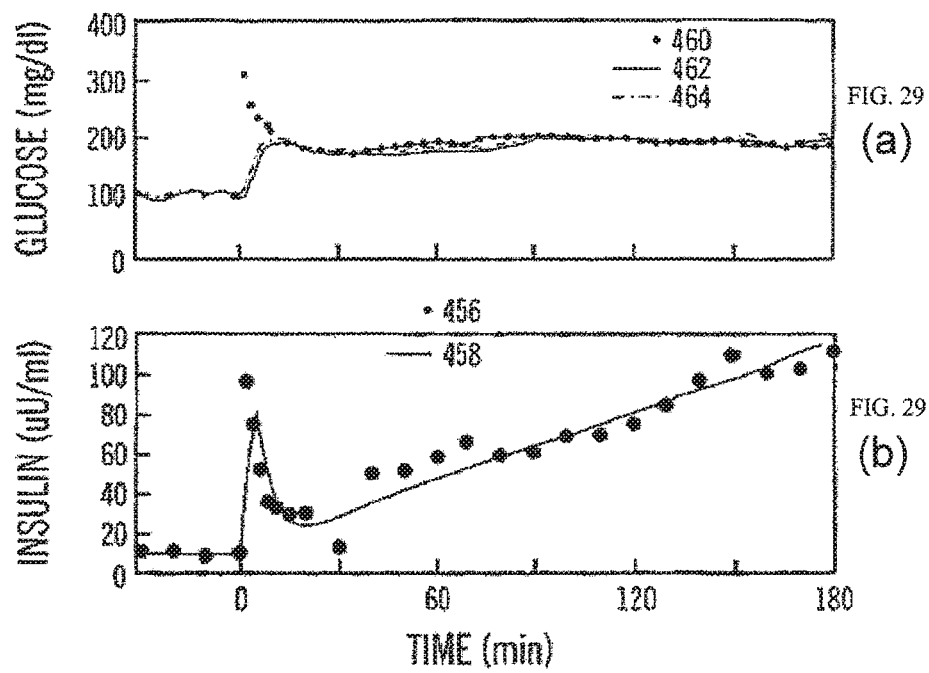
FIG. 29(a) is a plot of two different glucose sensor outputs compared to glucose meter readings during a glucose clamp in accordance with an embodiment.
FIG. 29(b) is a plot of actual insulin concentration in blood compared to a controller commanded insulin concentration in response to the glucose clamp of FIG. 29(a) in accordance with an embodiment.
Figure 30:
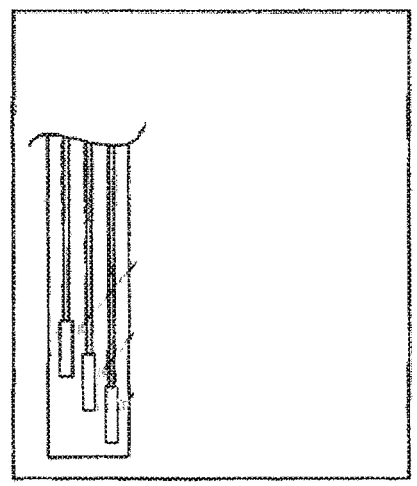
FIG. 30 is a top view of an end of a multi-sensor for measuring both glucose concentration and pH in accordance with an embodiment.
Figure 32:
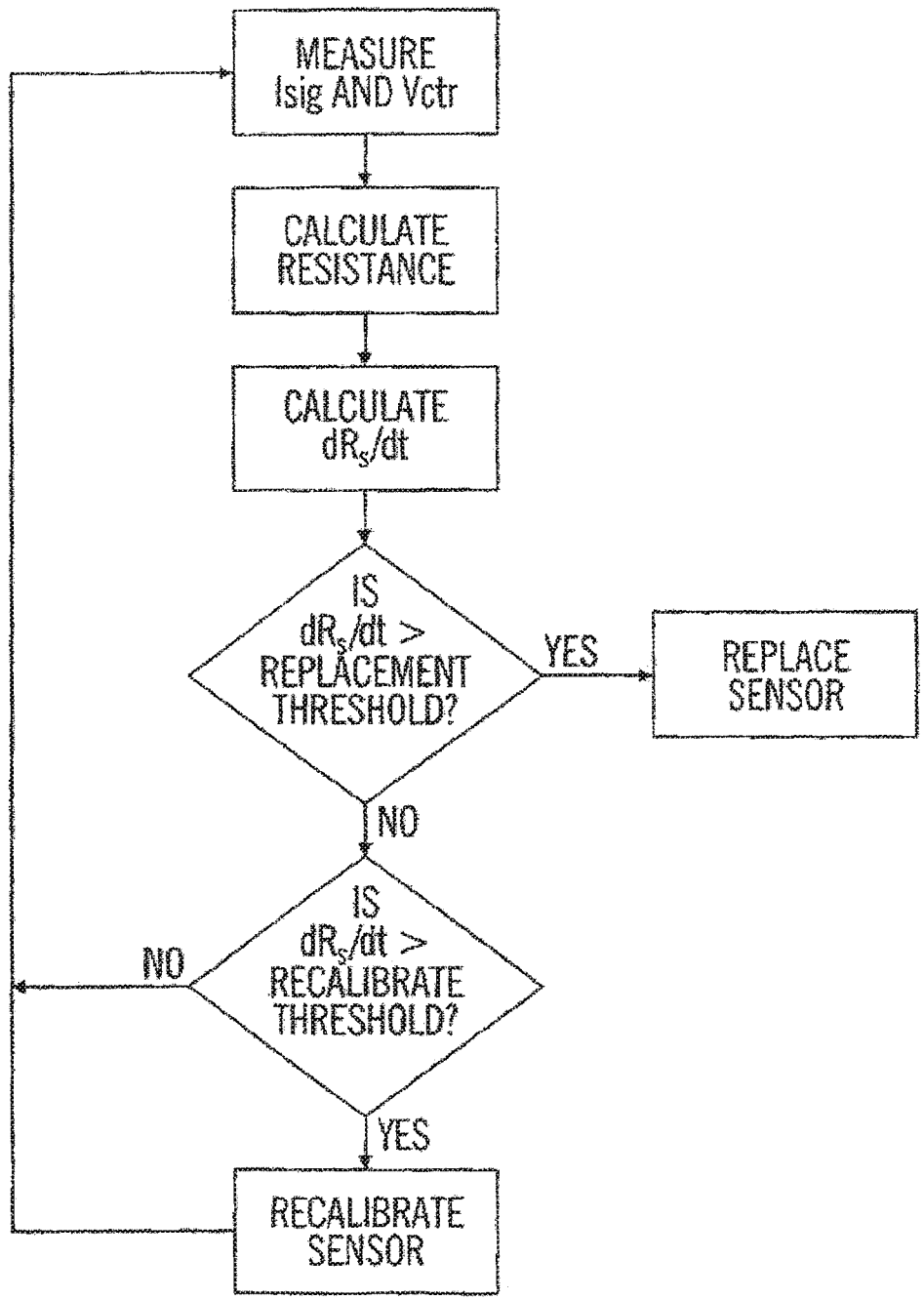
FIG. 32 is a block diagram using the derivative of sensor resistance to determine when to recalibrate or replace the sensor in accordance with an embodiment.
Figure 33:
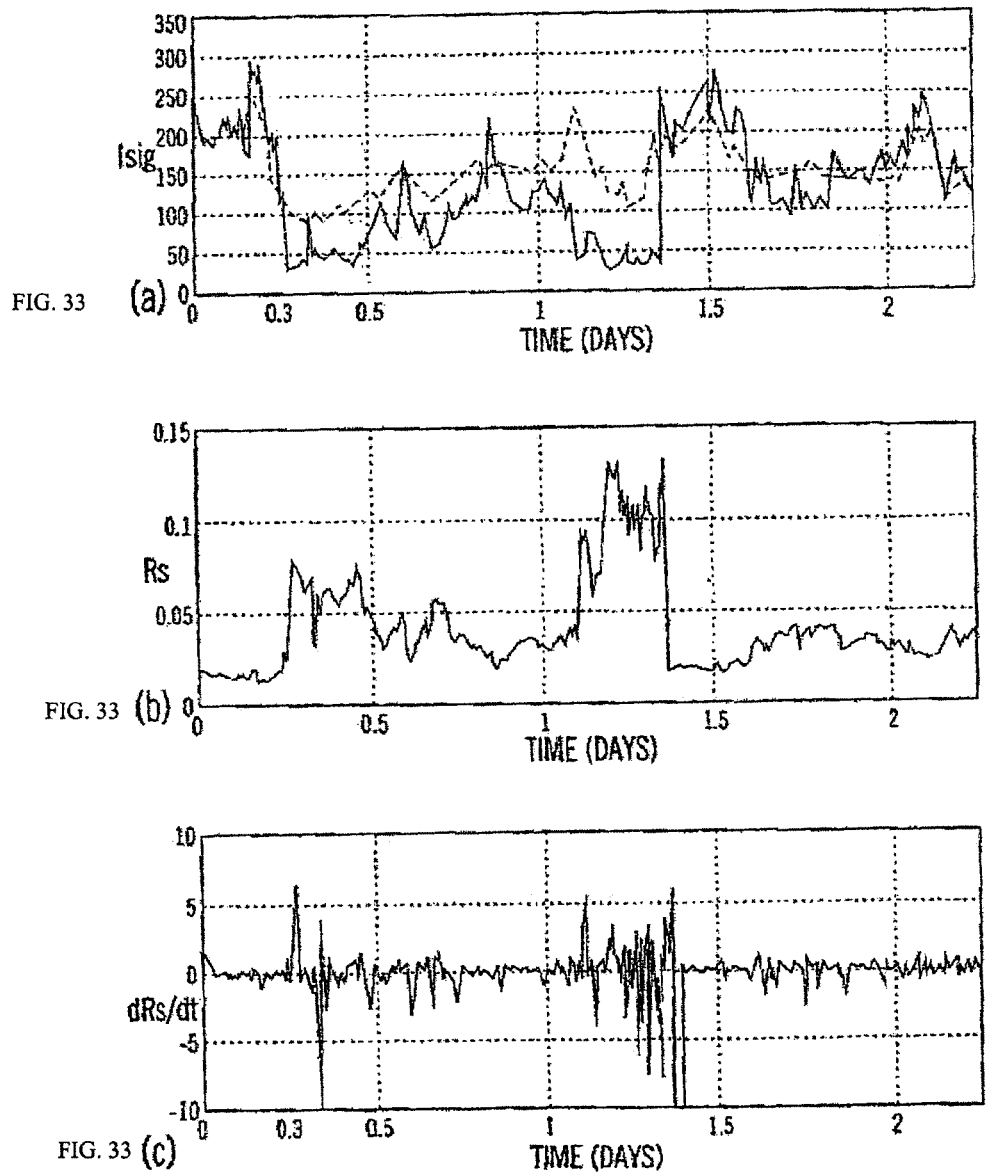
FIG. 33(a) is a plot of an analog sensor signal Isig over time in accordance with an embodiment.
FIG. 33(b) is a plot of sensor resistance over the same period of time as FIG. 32(a) in accordance with an embodiment.
FIG. 33(c) is a plot of the derivative of the sensor resistance of FIG. 32(b) in accordance with an embodiment.

A study was conducted to confirm that the insulin response for an individual could be reproduced using the glucose sensor as an input. In the study, glucose and insulin measurements were taken while a hyperglycemic clamp was applied to a NGT individual. The glucose level measurements, shown in FIG. 29(a), were used as the inputs to a mathematical model created to simulate a PID insulin response controller. The insulin dosing commanded by the controller in response to the glucose clamp very closely approximates the actual insulin appearance in the NGT individual, as shown in FIG. 29(b). The insulin concentration measured from periodic blood samples 456 taken from the individual during the test are represented by dots in FIG. 29(b). The output from the mathematical model simulating the insulin response commanded by the controller is shown as a solid line 458 in FIG. 29(b).

Three different devices were used to measure the individual's blood glucose during the study. Blood glucose meter readings 460 from periodic blood samples taken from the individual are represented by the dots in FIG. 29(a). Two MiniMed sensors (such as those described below) were placed in the individual's subcutaneous tissue, and the sensor readings 462, 464 are shown as lines in FIG. 29(a). The sensor readings 462, 464 are slightly delayed compared to the meter readings 460. The delay is most likely due to the delay between blood glucose and interstitial fluid (ISF) glucose and can be substantially corrected through the use of a filter if needed. In this study, the delay was not corrected by a filter and did not significantly affect the controller's ability to command an insulin response that matches the natural response of the NGT individual. This study indicates that the PID insulin response controller model is a good minimal model of insulin secretion that captures the biphasic response of healthy β-cells. Correction of the delay is only expected to increase the accuracy of the model. Fuzzy Logic to Select Between Multiple Sets of Controller Gains In particular referred embodiments, one set of controller gains is used for a particular individual. In alternative embodiments, more than one set of controller gains is used, and fuzzy logic is used to select between and/or among sets of controller gains and to determine when to change from one set of controller gains to another. In particular alternative embodiments, controller gains are different if the glucose level is above or below the desired glucose basal level. In other alternative embodiments, the controller gains are different if the glucose level is increasing or decreasing. A justification for different sets of gains comes from physiological studies that indicate that β-cells turn off faster than they turn on. In still other alternative embodiments, controller gains are different depending on whether the glucose level is above or below the desired glucose basal level and whether the glucose level is increasing or decreasing, which results in four sets of controller gains. In additional alternative embodiments, controller gains may change depending on the magnitude of the hypoglycemic excursion. In other words, the controller gains for small changes in glucose are different than those for large changes in glucose.

Self-Tuning Controller Gains

Further embodiments may include a controller that self tunes one or more the gains, $K_P$, $K_I$ and $K_D$, to accommodate changes in insulin sensitivity. In particular embodiments, previous measurements of glucose levels are compared to the desired basal glucose level $G_B$. For example, desired basal glucose level $G_B$ is subtracted from previous glucose level measurements. Then any negative values, within a predefined time window, are summed (in essence integrating the glucose level measurements that were below the basal glucose level $G_B$). If the resulting sum is greater than a pre-selected hypoglycemic integral threshold, then the controller gains are increased by a factor $(1+\alpha)$. Conversely, if the integral of the glucose level measurements that were measured above the basal glucose level $G_B$ within the predefined time window is greater than a pre-selected hyperglycemic integral threshold, then the controller gains are decreased by a factor $(1-\alpha)$.

In particular embodiments, a predefined time window over which the glucose concentration integrals are evaluated may be set at 24 hours, and controller gains may be adjusted if needed at the end of each such predefined time window. In alternative embodiments, integrals of the glucose level measurements may be continuously calculated over a moving window of time, and if either integral exceeds a threshold, the gains may be immediately adjusted. In particular embodiments, such a moving time window may be one hour, and the time window may be restarted whenever the gains are adjusted. In other alternative embodiments, the time window may be longer or shorter depending on the sensor accuracy, the rate at which an individual's insulin sensitivity changes, the computational capabilities of the hardware and/or the like.

In particular embodiments, the adjustment amount ($\alpha$) is 0.01. In alternative embodiments, the adjustment amount a is greater or smaller depending on the sensor accuracy, the rate at which an individual's insulin sensitivity changes, the rate at which the sensor sensitivity $S_I$ changes, and/or the like. In still other alternative embodiments, adjustment amount a is made larger or smaller depending on the amount that the integral of the measured glucose levels exceeds a threshold. In this way, gains may be adjusted by greater amounts if the measured glucose level G is significantly deviating from the desired blood glucose level $G_B$ and less if the measured glucose level G is closer to the desired blood glucose level $G_B$. In additional alternative embodiments, the controller employs a Kalman filter to establish glucose level G based on a series of blood glucose sensor measurements.

Modifying the PID Controller to Incorporate an Integrator Leak

In particular embodiments, a PID control response was described with constant gain components, $K_P$, $K_I$ and $K_D$. Although a control response may guarantee zero steady-state error (i.e. steady state glucose minus a desired basal glucose ($G_B=0$)), inherently, the integral component may destabilize feedback control because there is no temporal wind down of the insulin response while the integral component models an increase in insulin response. Here, the integral component may be expressed as follows:

$$U_I = K_I \int_{t_0}^{\tau} (G - G_B) dt + U_I(t_0).$$

Without any correction, integral component $U_I$ may have a tendency to over-estimate an increase in the insulin response. Since a small difference between steady-state glucose and $G_B$ is typically acceptable in insulin response control, an alternative modeling of the integral component can incorporate an integrator leak to reduce the magnitude of the destabilizing effect. Specifically, changes in $U_I(t)$ can be described by a term proportional to the error in glucose and a term that leaks in proportion to the magnitude of $U_I$. This can be shown by the following expression:

$$\frac{dU_I}{dt} = K_I(G - G_B) - K_{LEAK} U_I;$$

with initial condition $U_I = U_I(t_0)$.

The parameter $K_{LEAK}$ is the reciprocal time constant of the rate of leaking ($\tau_{LEAK}$ in min=$1/K_{LEAK}$), where $\tau_{LEAK}$ is a tuning parameter that can be set based on empirical data, and be tied with the other gain components $K_P$, $K_I$ and $K_D$. However, realization of an artificial β-cell may have $\tau_{LEAK}$ as a user input. $U_I$ can also be expressed in discrete form by standard methods.

Post-Controller (Lead/Lag) Compensator

In particular embodiments, commands may be issued from a controller without regard to where in the body the insulin delivery system is to infuse the insulin. In essence, the assumption is that the insulin is either delivered directly into the blood stream for immediate use by the body, or that any time delays caused by delivering the insulin somewhere in the body other than the blood stream can be compensated for by adjusting $K_P$, $K_I$ and/or $K_D$. In this case, commands attempt to model a β-cell insulin secretion profile, an example of which is shown in FIG. 35(a). Since β-cells secrete insulin directly into the blood stream, the β-cell insulin secretion profile is the intended blood plasma insulin concentration profile. However, an insulin delivery delay may distort the intended blood plasma insulin concentration profile, as shown in FIG. 35(b). Here, an insulin delivery delay is the amount of time between the instant that the command is given to the insulin delivery system to infuse insulin and the time that insulin reaches the blood plasma.

Figure 20:
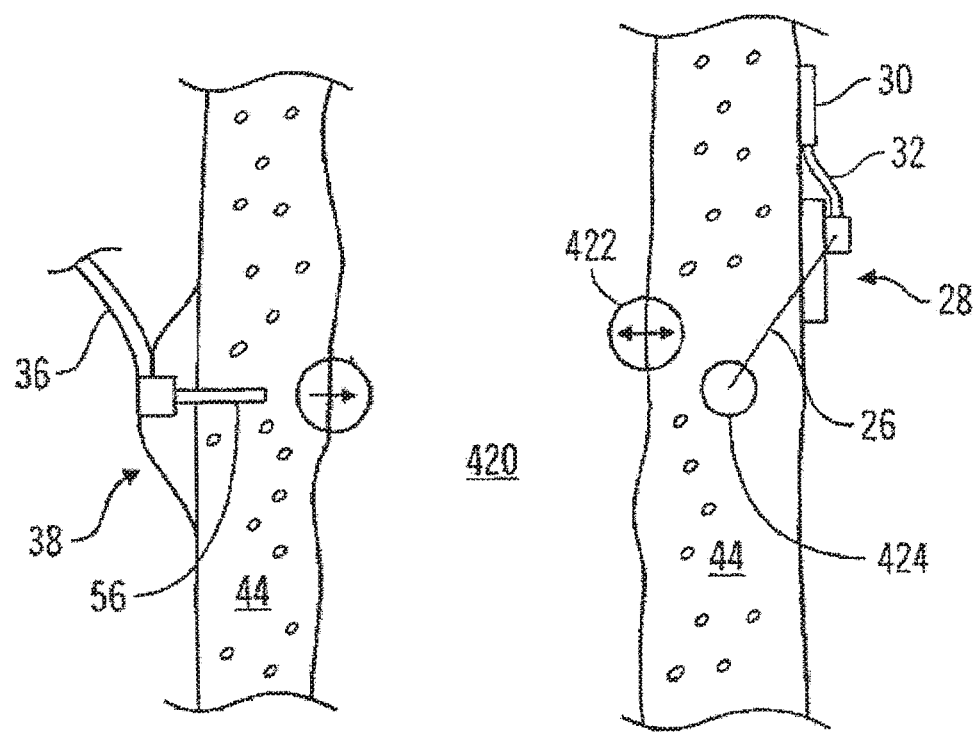
FIG. 20 is a cross-sectional view of a sensor set and an infusion set attached to the body in accordance with an embodiment.

An insulin delivery delay may be caused by a diffusion delay, represented by a circle with an arrow 528 in FIG. 20, which is the time required for insulin that has been infused into a tissue to diffuse into the blood stream. Other contributors to insulin delivery delay may include, time for the delivery system to deliver the insulin to the body after receiving a command to infuse insulin, time for the insulin to spread through out the circulatory system once it has entered the blood stream, and/or by other mechanical or physiological causes. In addition, the body clears insulin even while an insulin dose is being delivered from the insulin delivery system into the body. Since insulin is continuously cleared from the blood plasma by the body, an insulin dose that is delivered to the blood plasma too slowly or is delayed is at least partially, if not significantly, cleared before the entire insulin dose fully reaches the blood plasma. Therefore, the insulin concentration profile in the blood plasma never achieves the same peak (nor follows the same profile) it would have achieved if there were no delay. Given an insulin dose delivered all at once into the blood plasma at time zero, an insulin concentration in the blood plasma is raised virtually instantaneously (not shown) and then would decrease exponentially over time as the body clears (uses or filters out) the insulin, as shown in FIG. 36(*a*) per the following expression:

$$C_P = \frac{I_0}{V_P} e^{-P_I t},$$

where:

$C_P$ is the concentration of insulin in the blood plasma;
$I_0$ is a mass of the insulin dose delivered directly to the blood plasma at time zero;
$V_P$ is a volume of the blood plasma in the body;
$P_I$ is a reciprocal time constant for insulin clearance; and
t is the time that has passed since the delivery of the insulin dose directly into the blood plasma.

Time constant for insulin clearance $P_I$ may be calculated as follows:

$$P_I = \frac{k}{V_P},$$

where:

k is the volume insulin clearance rate; and
$V_P$ is a volume of the blood plasma in the body.

Alternatively, time constant for insulin clearance $P_I$ may be obtained by providing insulin to an individual that does not generate his own insulin, and then periodically testing blood samples from the individual for insulin concentration. Then, using an exponential curve fitting routine, generate a mathematical expression for a best-fit curve for the insulin concentration measurements, and observe the time constant in the mathematical expression.

Given the same insulin dose (delivered at time zero all at once) into the subcutaneous tissue, instead of directly into the blood plasma, the concentration of insulin in the blood plasma may begin to rise slowly as insulin diffuses from the interstitial fluid ISF into the blood plasma, as shown in FIG. 36(*b*). At the same time that insulin is entering the blood plasma, the body may be clearing insulin from the blood. While the rate at which insulin is entering the blood plasma exceeds the insulin clearance rate, the insulin concentration in the blood plasma may continue to increase. If the insulin clearance rate exceeds the rate at which insulin is entering the blood plasma from the interstitial fluid ISF, the insulin concentration in the blood plasma may begin to decrease. So, the result of delivering insulin into the interstitial fluid ISF instead of directly into the blood stream is that the insulin concentration in the blood plasma is spread over time rather than increased virtually instantaneously to a peak followed by a decay.

The following bi-exponential expression may be used to model the insulin concentration in blood plasma given an insulin dose delivered to the subcutaneous tissue:

$$C_P = \frac{I_0 D}{V_P V_{ISF}(P_3 - P_2)} (e^{-P_2 t} - e^{-P_3 t}),$$

where:

$C_P$ is the concentration of insulin in the blood plasma;
$I_0$ is the mass of the insulin dose delivered to the subcutaneous tissue at time zero;
D is a diffusion coefficient (the rate at which insulin diffuses from the interstitial fluid ISF into the blood glucose);
$V_p$ is a volume of the blood plasma in the body;
$V_{ISF}$ is a volume of interstitial fluid ISF that the insulin is delivered to;
$P_2$ is a time constant;
$P_3$ is a time constant greater than or equal to $P_2$; and
t is time since the delivery of the insulin dose into the interstitial fluid ISF.

Time constants may be calculated using the following quadratic formula:

$$P_2, P_3 = -\frac{a_1 \pm \sqrt{a_1^2 - 4a_0}}{2},$$

where:

$$a_1 = \frac{D+K}{V_P} + \frac{D}{V_{ISF}}; \text{ and}$$

$$a_0 = \left(\frac{D+K}{V_P}\right)\left(\frac{D}{V_{ISF}}\right) - \frac{D^2}{V_{ISF} V_P}.$$

Figure 37:
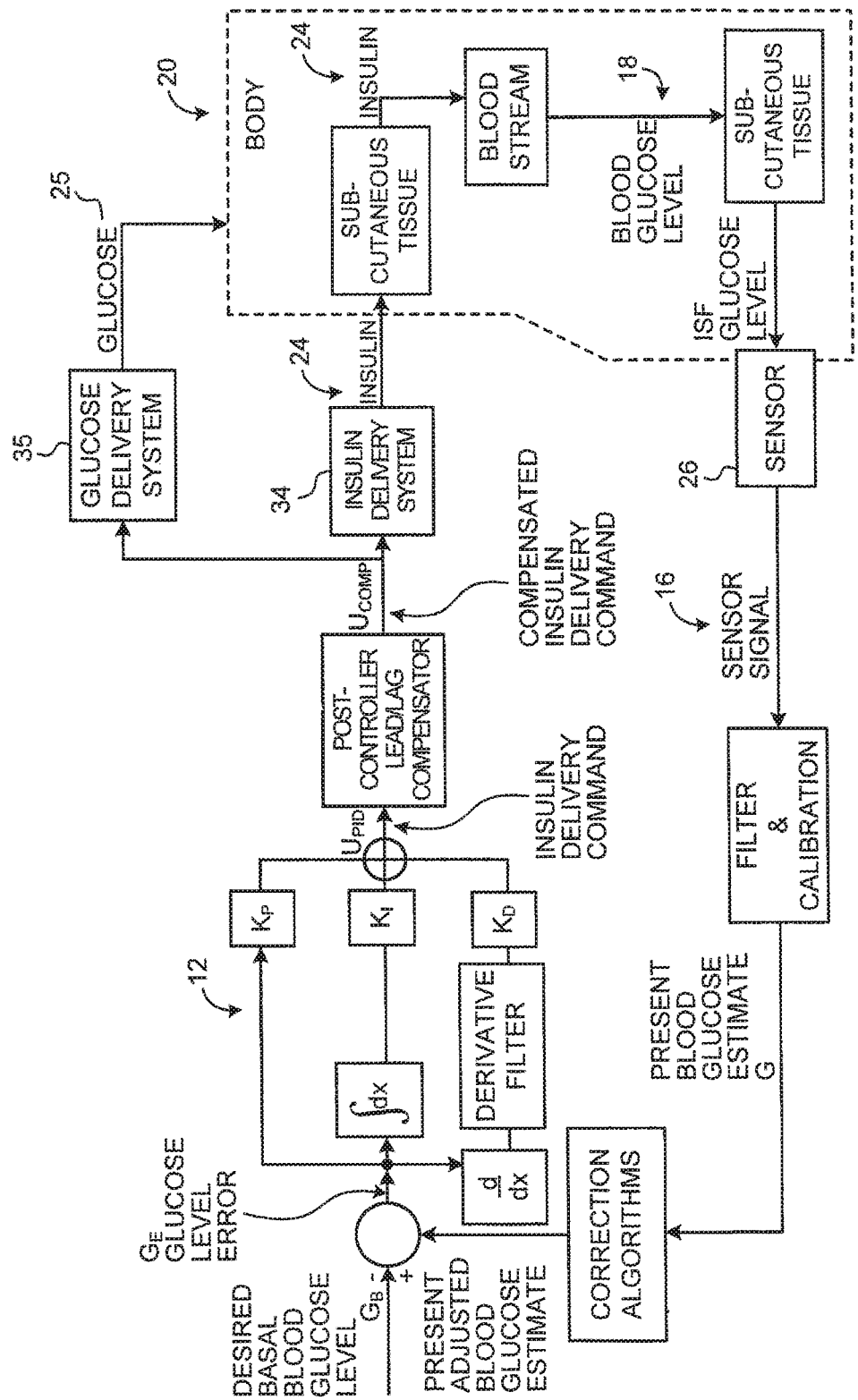
FIG. 37 is a schematic diagram of an embodiment of the closed loop system of FIG. 26 with the addition of a post-controller compensator and a derivative filter in accordance with an embodiment.
Figure 38:
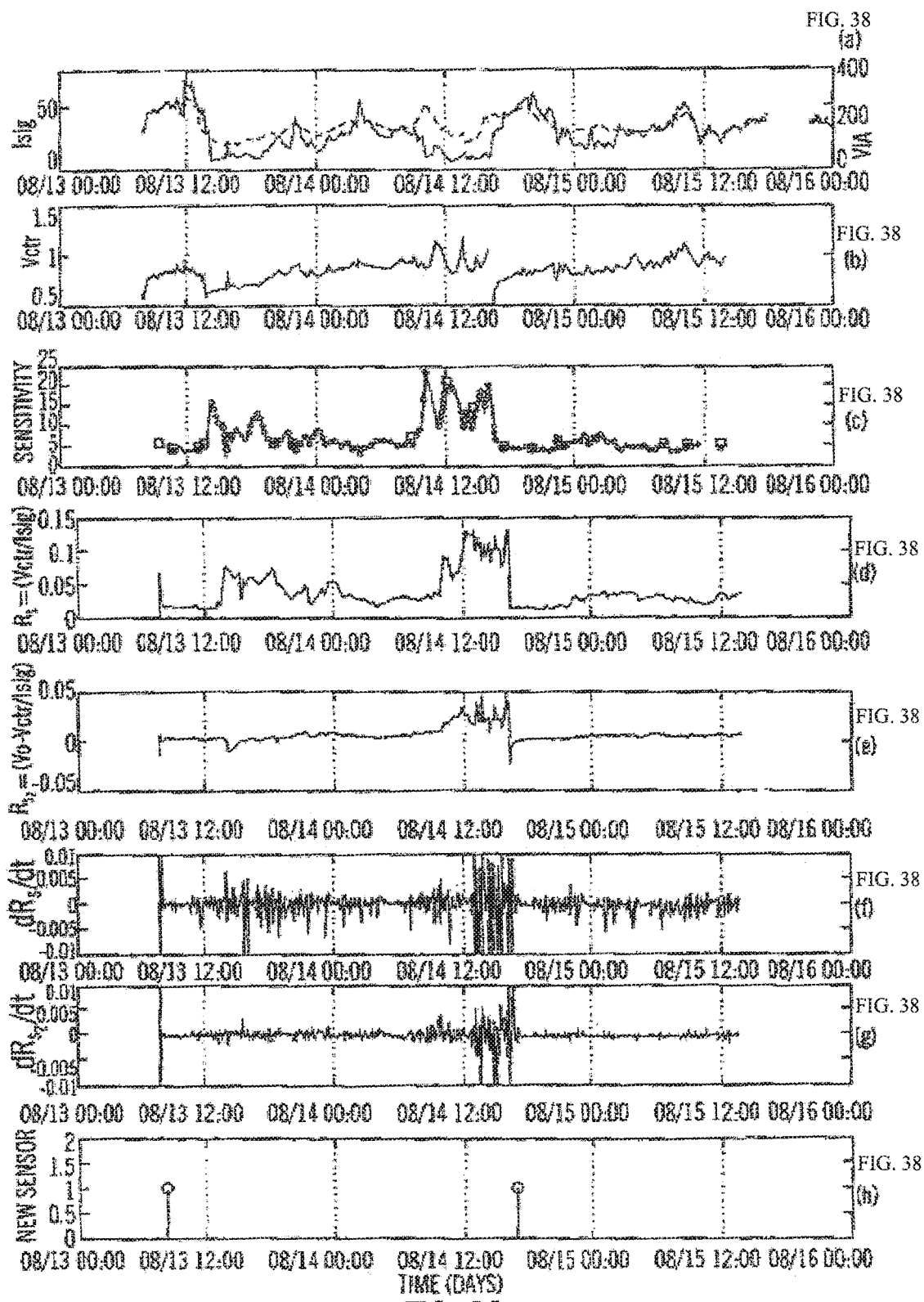
FIG. 38(a) is a plot of sensor signal measurements and $V_{ia}$ measurements with respect to time in accordance with an embodiment.
FIG. 38(b) is a plot of a measured counter electrode voltage $V_{ctr}$ with respect to time in accordance with an embodiment.
FIG. 38(c) is a plot of calculated sensor sensitivity with respect to time in accordance with an embodiment.
FIG. 38(d) is a plot of a calculation of sensor resistance $Rs_1$ with respect to time in accordance with an embodiment.
FIG. 38(e) is a plot of another calculation of sensor resistance $Rs_2$ with respect to time in accordance with an embodiment.
FIG. 38(f) is a plot of the derivative of sensor resistance $Rs_1$ of FIG. 38(d) with respect to time in accordance with an embodiment.
FIG. 38(g) is a plot of the derivative of the sensor resistance $Rs_2$ of FIG. 38(e) with respect to time in accordance with an embodiment.
FIG. 38(h) is a plot of when sensors were replaced with respect to time in accordance with an embodiment.

In alternative embodiments, a post-controller lead-lag compensator 522 may modify commands (e.g., $U_{PID}$) to compensate for insulin delivery delay and/or insulin clearance rate k, as shown in FIG. 37. Here, post-controller lead-lag compensator 522 may modify comments according to the following expression:

$$\frac{U_{COMP}}{U_{PID}} = \frac{s + \alpha}{s + \gamma},$$

Where:

$1/\alpha$ is a lead constant;
$1/\gamma$ is a lag constant;
s is the Laplace variable, and
$U_{COMP}$ is the compensated commands calculated by the lead-lag compensator 522.

A PID controller may generate commands ($U_{PID}$) for a desired insulin delivery rate and/or glucose delivery rate into the blood plasma. Commands $U_{PID}$ are calculated and issued periodically depending on the update rate for the control loop, which is selected based on a maximum anticipated rate of change of the blood glucose level, an insulin delivery system minimum insulin dosage, insulin sensitivity, a maximum and a minimum acceptable glucose concentration, or the like. Commands $U_{PID}$ may be used as inputs to post-controller lead-lag compensator 522.

In particular embodiments, compensated commands ($U_{COMP}$) issued from the post-controller lead-lag compensator 522 may use more than one value from the controller. In particular embodiments, post-controller lead-lag compensator 522 may use a present command ($U_{PID}^n$) provided in a current command cycle and a command ($U_{PID}^{n-1}$) provided in a previous command cycle to calculate a compensated command $U_{COMP}$ per a compensation expression as follows:

$$U_{COMP}^n = (1-\gamma)U_{COMP}^{n-1} + U_{PID}^n + (1-\alpha)U_{PID}^{n-1},$$

where:

$U_{PID}^n$ is the command provided in and/or associated with the current command cycle;

$U_{PID}^{n-1}$ is the command provided in and/or associated with the previous command cycle;

$U_{COMP}^{n-1}$ is the compensated control output provided in and/or associated with the previous command cycle;

$\alpha$ is the reciprocal lead time constant in $\min^{-1}$; and $\gamma$ is the reciprocal lag time constant in $\min^{-1}$.

Here, the above expression comprises a first forward difference equation. However, other forms can be used alternatively (e.g. first backward or bilinear) to provide a compensated control output ($U_{COMP}$) that is comprised of a weighted history of both past PID outputs ($U_{PID}$), and past compensated outputs ($U_{COMP}$).

An alternative method of modifying the commands ($U_{PID}$) to compensate for the insulin delivery delay and/or the insulin clearance can be performed based on a weighted history of past insulin delivery. By giving the most recent delivery history more weight, the weighted history of the previous insulin delivered can then be subtracted from the present PID control output to yield a compensated control output. This may be expressed in Laplace domain as follows:

$$U_{COMP} = PID \times E - \frac{\lambda}{s+\alpha}U_{COMP},$$

where:

E is the Laplace transformed error signal ($G-G_B$);

$\lambda$ determines how much the PID output is reduce in proportion to the weighted history of past control outputs; and $\alpha$ is the reciprocal time constant determining how long a history is weighted (e.g., value of a could be equal to the reciprocal dominant time constant or subcutaneous insulin appearance, $P_2$).

The compensated signals may be solved as a function of the error as follows:

$$\frac{U(s)}{E(s)} = PID\frac{s+\alpha_w}{s+(\alpha+\lambda)} = PID\frac{s+\alpha_w}{s+\gamma},$$

which is identical to the previously described lead-lag compensation.

In other alternative embodiments, additional previous command values may be used. In still other alternative embodiments, lead-lag compensation may compensate for both time constants $P_2$ and $P_3$.

In still other alternative embodiments, controller gains may be modified to include effects of the post-controller lead/lag compensator so that the post-controller lead/lag compensator is not needed to modify the commands to account for insulin and/or glucose delivery delay.

In particular embodiments, an insulin delivery system and/or glucose delivery system may provide finite doses of insulin and/or glucose into the body in response to commands from the controller. For example, the smallest amount of insulin that a insulin delivery system can deliver is the minimum finite insulin dose. The controller may generate commands for a dose of insulin to be delivered that is not an integer number multiple of the minimum finite insulin dose. Therefore, either too much or too little insulin may be delivered by the insulin delivery system in response to the commands. Likewise, the smallest amount of glucose that a glucose delivery system can deliver may be the minimum finite glucose dose. The controller may generate commands for a dose of glucose to be delivered that is not an integer number multiple of the minimum glucose dose. Accordingly, either too much or too little glucose may be delivered by the glucose delivery system.

In particular alternative embodiments, post-controller lead-lag compensator may truncate command to the nearest whole number multiple of the minimum finite insulin dose and adds the remaining commanded volume of insulin/glucose to the next command. In other alternative embodiments, a compensator rounds the command to the nearest integer number multiple of doses. In still other alternative embodiments, other methods are used to compensate for the difference between the commands and the nearest integer number multiple of the minimum finite doses. In other embodiments, no such compensation is needed.

Eliminating the Lead-Lag Compensator with Feedback of Predicted Plasma Insulin

In yet in another alternative embodiment, PID control commands may be modified to emulate the effect of plasma insulin on a β-cell to determine optimal insulin administration by feeding back a predicted plasma insulin based on the subcutaneous insulin infusion. The net effect of such feedback is to replace an undesired dynamic with a more desirable one and achieve a plasma insulin profile that a β-cell would achieve. This is explained below using Laplace transformed variables. Here, assume the relation between glucose above basal ($G-G_B$) and insulin delivery (ID) is described by a linear transfer function as follows:

$$ID(s) = C(s)(G(s)-G_B)$$

where C(s) may be, but is not necessarily, described by the PID controller transfer function.

If a β-cell is using plasma insulin ($I_p(s)$) levels to suppress insulin secretion, an expression for the predicted rate of insulin delivery may be modified as follows:

$$ID(s) = C(s)(G(s)-G_B) - kI_p(s)$$

For portal insulin delivery the relation between ID(s) and plasma insulin $I_p(s)$ is known to be approximated by a single time delay as follows:

$$I_p(s) = \frac{k_1}{s+\alpha}ID(s).$$

Substituting $I_p(s)$ value into the previous formula and making k large results in:

$$ID(s) = \frac{C(s)[G(s) - G_B]}{1 + \frac{kk_1}{s + \alpha}} \approx C(s)\frac{s + \alpha}{kk_1}[G(s) - G_B]; \quad 1 << \frac{kk_1}{s + \alpha}$$

As such, the undesirable time constant $1/\alpha$ can be completely cancelled. In practice, a lower value of k may be used to provide:

$$ID(s) = C(s)[G(s) - G_B] - \frac{kk_1}{s + \alpha}ID(s)$$
$$= C(s)\frac{s + \alpha}{S + \gamma}[G(s) - G_B]$$

where $\gamma = \alpha + kk_1$ (i.e., something greater than $\alpha$).

Thus, the effect for the β-cell of adding a plasma insulin feedback is to replace the portal insulin delivery time constant ($\alpha$) with a faster time constant ($\gamma = \alpha + kk_1; \gamma > \alpha$). In block diagram form:

$$G - G_B \rightarrow C(s)\frac{s + \alpha}{S + \gamma} \xrightarrow{ID} \frac{k_1}{s + \alpha} \xrightarrow{I_P},$$

which is equivalent to:

$$G - G_B \rightarrow C(s)\frac{1}{s + \gamma} \xrightarrow{I_P}$$

To apply this mechanism to subcutaneous insulin delivery all that is needed is the transfer function between sc insulin delivery and plasma insulin. This transfer function may be approximated by a bi-exponential time course (bolus response) as follows:

$$\frac{I_P(s)}{IDsc(s)} = \frac{k_2}{(s + \alpha_1)(s + \alpha_2)}, \text{ thus}$$
$$ID(s) = C(s)[G(s) - G_B] - \frac{kk}{(s + \alpha_1)(s + \alpha_2)}ID(s)$$
$$= C(s)\left[1 + \frac{kk_2}{(s + \alpha_1)(s + \alpha_2)}\right]^{-1}[G(s) - G_B]$$

In the limiting case as $kk_2/(s+\alpha_1)(s+\alpha_2) >> 1$, this transfer function may be approximated as follows:

$$ID(s) = C(s)\frac{(s + \alpha_1)(s + \alpha_2)}{kk_2}[G(s) - G_B]$$

Again, undesirable time constants associated with subcutaneous insulin delivery have been eliminated. In practice such undesirable rate constants may just be replaced with more desirable rate constants (e.g., faster time constants). Correction of Hypoglycemic Excursion Around ~200 Minutes (Wind-Down)

Figure 41:
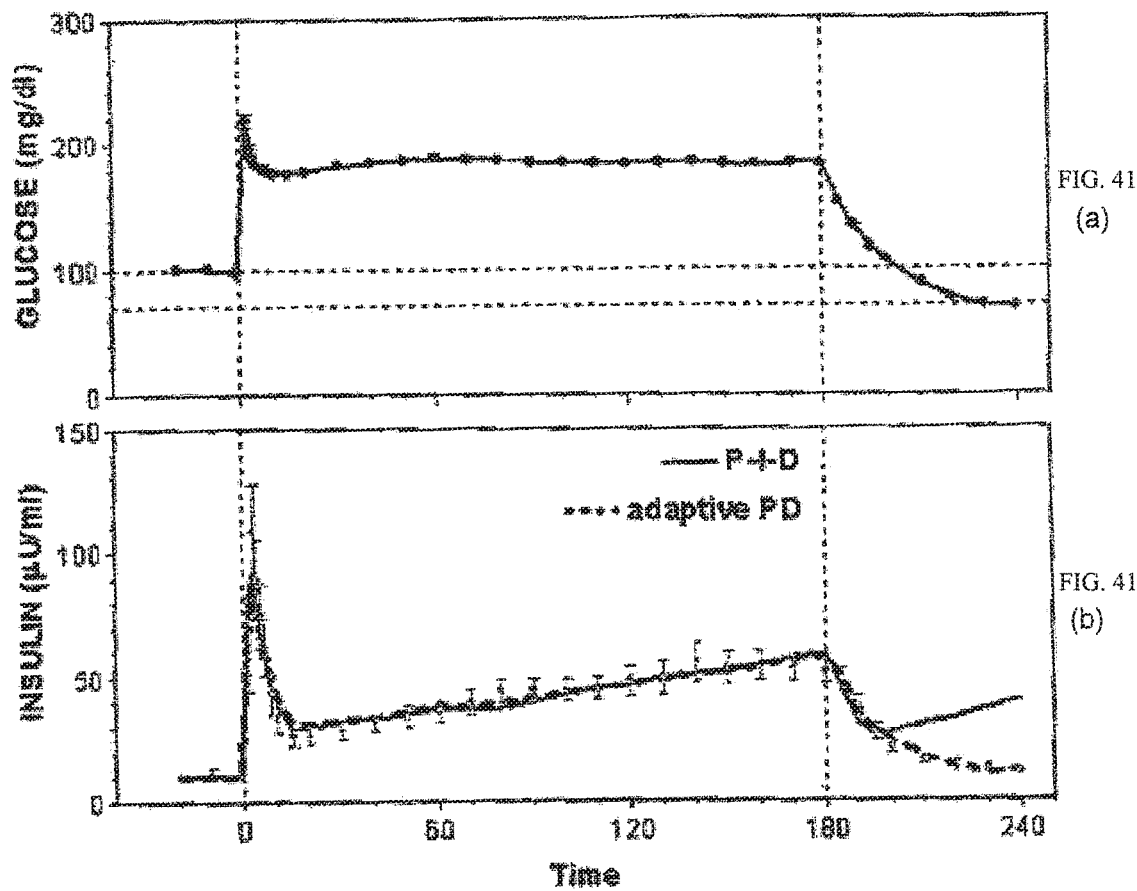
FIG. 41(a) is a plot of actual blood glucose concentration in accordance with an embodiment.
FIG. 41(b) is a plot of actual insulin concentration in blood compared to a controller commanded insulin concentration in response to the blood glucose in FIG. 41(a) in accordance with an embodiment.

Modeling of β-cells using a PID controller can be used to predict "first" and "second" phase insulin responses during prolonged periods of increased glucose appearance. However, if such periods of increased glucose appearance is followed by a rapid decrease in glucose appearance, the PID controller may not be able to correctly predict the wind down of the insulin response to lower glucose levels. FIG. 41(b) illustrates an insulin response to the blood glucose level of FIG. 41(a) based on the clinical data (shown as data points), the PID modeling (shown as a solid line), and correction of the PID for the hypoglycemic excursion (shown as a dashed line).

In particular embodiments, hypoglycemic excursion may be corrected by modifying the PID controller to a PD control with Adaptive Proportional Gain (or Bilinear PID controller), which is modified form of the original PID expressions. As described previously, a discrete PID expression may be provided as follows:

Proportional Component Response: $P_{con}^{n} = K_P(SG_f^{n} - G_{sp})$,
Integral Component Response: $I_{con}^{n} = I_{con}^{n-1} + K_I(SG_f^{n} - G_{sp})$, $I_{con}^{0} = I_b$; and
Derivative Component Response: $D_{con}^{n} = K_D dGdt_f^{n}$, where $K_P$, $K_I$, and $K_D$ are the proportional, integral, and derivative gain coefficients, $SG_f$ and $dGdt_f$ are the filtered sensor glucose and derivative, respectively, and the superscript n refers to discrete time.

In the Bilinear PID controller, the proportional gain $K_P$ is based on the integrated error term. The magnitude of each component's contribution to the insulin response is described by the following expressions:

$$P_{con}^{n} = K_P^{n}(SG_f^{n} - INT)$$

$$D_{con}^{n} = K_D dGdt_f^{n}$$

$$K_P^{n} = K_P^{n-1} + K_1(SG_f^{n} - G_{sp}), \text{ where}$$

$$K_P^{0} = K_{P0}.$$

The proportional gain now integrates at rate $K_I$ (initial value $K_{P0}$) and the proportional component is related to an intercept value (INT) where (INT<$G_{sp}$). The modified formulation can be seen to fit the hypoglycemic glucose excursion without systematic error as the adaptive PD line shown as a dashed line in FIG. 41(b).

In additional embodiments, the Bilinear PID controller can also incorporate an integrator leak by modifying the formula to multiply the previous $K_P$ with a value such as a as follows:

$$K_P^{n} = \alpha K_P^{n-1} + K_I(SG_f^{n} - G_{sp}), \text{ where } \alpha \approx 0.99.$$

An alternative method of correcting the hypoglycemic glucose excursion can be performed by integrator clip into the PID control. In a particular implementation, a PID controller may have integrator-reset rules that prevent excessive "winding" and such a rule can be used to correct hypoglycemic glucose excursion. For example, the integrator can be clipped as follows:

If (SG≤60 mg/dl and $I_{con}^{n-1} > K_P$(SP−60), then $I_{con}^{n-1} = K_P$(SP−60).

In this particular example, the integrator may be reset such that if the sensor glucose falls below 60 mg/dl the insulin delivery is zero for all stable or falling sensor glucose signals. The clipping limit may represent an absolute threshold, similar to the human counter regulatory response.

In other particular implementations, a β-cell may be emulated using piecewise continuous functions. For example, the following function allows for progressive clipping to be tuned:

$$\gamma(SG) = \gamma_0 + (1-\gamma_0)\left[\frac{T_I - SG}{T_I - 60}\right] \text{ if}$$

$$SG \leq T_I \text{ mg}/dl \text{ and } I_{con}^{n-1} > \gamma K_P(PS-60),$$

then $I_{con}^{n-1} = \gamma K_P(PS-60)$.

This technique introduces two additional tuning parameters ($\gamma_0$ and $T_I$) and starts to check the integrator output at a higher threshold. For example, if $\gamma_0=5$ and $T_I=100$ mg/dl, and SP=120 mg/dl, the integrator output would be clipped to 4 $K_P$60 if glucose fell to 90 mg/dl, 3 $K_P$60 if glucose fell to 80 mg/dl and so forth until glucose reached 60 where it would be clipped at $K_P$60. It should be understood, however, that this is merely an example of how behavior of a β-cell may be modeled in a particular implementation, and that others techniques may be used (e.g., using functions based on the rate of fall of glucose or percent decrease in $I_{con}$) without deviating from claimed subject matter.

Application of PID to Control Delivery of Insulin and/or Glucose

As discussed above in relation to FIG. 1, delivery of insulin and glucose is controlled by commands from controller 12. Here, for example, controller may determine whether to deliver insulin or glucose, and specific amounts to be delivered by insulin delivery system 14 and glucose delivery system 15. In a particular implementation, insulin or glucose may be delivered in an amount based, at least in part, on the value of $U_{PID}$ or $U_{COMP}$. In a particular implementation, if $U_{PID}$ or $U_{COMP}$ is greater than zero, insulin may be delivered at a rate based, at least in part, on a magnitude of $U_{PID}$ or $U_{COMP}$ as determined above. Similarly, if $U_{PID}$ or $U_{COMP}$ is less than zero, glucose may be delivered in an amount based, at least in part, on a magnitude of $U_{PID}$ or $U_{COMP}$.

In one particular implementation, an insulin infusion rate may be determined as follows:

If $U_{PID/COMP} \leq 0$, $Ins_{rate}=0$;

otherwise, $Ins_{rate}=U_{PID/COMP}$, $InSInf_{rate}=Ins_{rate}*W$ where:
$U_{PID/COMP}=U_{PID}$ or $U_{COMP}$, whichever is applicable;
W=bodyweight of patient in kg; and
$InsFus_{rate}$=insulin infusion rate.

In one particular implementation, $InsFus_{rate}$ may be limited to a maximum value such as 0.999 U/kg/hr, for example. However, this is merely an example of a maximum infusion rate that may be set or programmed into controller 12 and claimed subject matter is not limited in this respect.

According to an embodiment, after infusion of insulin as been stopped, controller 12 may require a threshold minimum level of patient blood glucose level before commencing infusing insulin again. In one particular implementation, and as illustrated above, controller 12 may generate commands to insulin delivery system 14 on periodic intervals and/or command cycles. For example, during a current command cycle, controller 12 may determine commands to be applied and/or transmitted to insulin delivery system 14 in a subsequent command cycle. In an instance where infusion of insulin has been stopped, the value of $Ins_{rate}$ (as determined above) may be zero (making the insulin infusion rate $InsInf_{rate}$ zero). Here, in determining a command to insulin delivery system 14 for a subsequent command cycle, controller 12 may determine whether a blood glucose level forecasted for the subsequent command cycle exceeds a threshold minimum blood glucose level as follows:

If $$Ins_{rate}^{n-1} = 0, \text{ and } G^{n-1} + \frac{dG}{dt}\Delta t < G_{min}, Ins_{rate}^{n} = 0;$$

If $$Ins_{rate}^{n-1} = 0, \text{ and } G^{n-1} + \frac{dG}{dt}\Delta t \geq G_{min}, Ins_{rate}^{n} = U_{PID/COMP};$$

where:
$Ins_{rate}^{n-1}$ rate is the value of parameter $Ins_{rate}$ for determining insulin infusion rate in command cycle n−1;
$Ins_{rate}^{n}$ is the value of parameter $Ins_{rate}$ for determining insulin infusion rate in command cycle n;
$G^{n-1}$ is blood glucose estimated in command cycle n−1;
$G_{min}$ is the threshold minimum blood glucose before insulin infusion may recommence; and
$\Delta t$ s the period of a command cycle.

In one particular application, as pointed out above, the system of FIG. 1 may be implemented in a hospital environment where actions of the controller 12 to control infusion of insulin and/or glucose are monitored by an attendant or caretaker such as a nurse. Here, such a caretaker may be tasked to check the system of FIG. 1 upon the occurrence of certain events such as, for example, changes in the rate of infusion of insulin and/or glucose.

In a particular embodiment, changes in the rate of insulin infusion may be controlled to be at least a minimum change. This would avoid the occurrence of events arising from very small or insignificant changes in the rate of insulin infusion that would require a caretaker to physically check the closed-loop system. In a particular implementation, controller 12 may be configured change an insulin infusion rate in minimum amounts. Here, a change in insulin infusion rate for a subsequent command cycle n may be determined as follows:

if $|Ins_{rate}^{n-1} - U_{PID/COMP}| < \Delta Ins_{rate}^{min}$, then
$Ins_{rate}^{n}=Ins_{rate}^{n-1}$ where:
$\Delta Ins_{rate}^{n}$ is the minimum allowed change in insulin infusion rate.

In an alternative implementation, a minimum change may be defined as a minimum percentage change. Here, a change in infusion rate for a subsequent command cycle n may be determined as follows:

If $$\frac{|Ins_{rate}^{n-1} - U_{PID/COMP}|}{Ins_{rate}^{n-1}} \times 100 < \% \Delta Ins_{rate}^{min}, \text{ then } Ins_{rate}^{n} = Ins_{rate}^{n-1},$$

where:
% $\Delta Ins_{rate}^{n}$ is the minimum allowed percentage change in insulin infusion rate.

As mentioned above, if $U_{PID}$ or $U_{COMP}$ is less than zero, glucose may be delivered in a bolus amount based, at least in part, on a magnitude of $U_{PID}$ or $U_{COMP}$. In one particular implementation, such a glucose bolus amount may be calculated as follows:

If $U_{PID/COMP} \geq 0$, $G_{rate}=0$;

otherwise, $G_{rate} = U_{PID/COMP} * W(kg) * 0.24$ mL/hr of D25W;

$$G_{bolus} = G_{rate} * Tinf2bolus,$$

Where Tinf2bolus is a time period until the next suggested blood glucose measurement.

According to an embodiment, controller 12 may be configured and/or programmed to provide commands for bolus amounts having a minimum size. This may avoid the use of bolus amounts that are of insignificant size. Here, a glucose bolus amount may be further determined as follows:

If $-U_{PID/COMP} < 0.5 \text{MinInfusSet}\Delta$, then $G_{rate} = 0$, where MinInfusSet$\Delta$ is the minimum absolute infusion change allowed with particular delivery devices used (e.g., glucose delivery system 15).

In certain applications, it may be desirable to limit the size of a glucose bolus to avoid severe hyperglycemia. For example, it may be desirable to limit infusion of glucose only in situations when blood glucose is high. Also, according to another embodiment, controller 12 may be configured and/or programmed to limit the infusion of glucose to conditions where blood glucose is high. Here, controller 12 may further determine whether a bolus of glucose should be infused in a subsequent command cycle n as follows:

If $$G^{n-1} + \frac{dG}{dt}\Delta t > G_{max}, \text{ then } G_{rate}^n = 0,$$

where $G_{rate}^n$ is the parameter $G_{rate}$ for determining a command for a glucose bolus in subsequent command cycle n.

Application of Closed-Loop System to Hospital Environment

As discussed above according to a particular implementation, a hospitalized patient may receive insulin and/or glucose infusion via one or more of embodiments of a closed-loop system described herein. For example, such a patient, having a body 20, may receive insulin and/or glucose infusion via the closed-loop system described above with reference to FIG. 1. In this particular example, the patient may receive infusions of insulin and/or glucose via an intravenous tube based, at least in part, on measurements of blood-glucose concentrations in the patient obtained using one or more techniques described herein.

According to an embodiment, an attendant or caretaker, such as a hospital nurse, may be tasked to interact with a closed-loop system to, among other things, monitor changes in and/or implement changes in therapy being applied to the patient via the closed-loop system. In one embodiment, a caretaker may be tasked to check the state of the closed loop system (e.g., present blood-glucose level, insulin infusion rate, etc.) periodically. In another embodiment, a closed-loop system such as that shown in FIG. 1, may initiate an alarm to an individual in response to one or more detected conditions and/or events.

In a particular implementation, for example, a closed loop system, such as that discussed above with reference to FIG. 1, may initiate an alarm to an attendant in response to a suggested change in a recommended therapy being applied to a patient. As discussed above, such a recommended therapy may comprise, for example, an infusion of insulin at a set infusion rate or a bolus of glucose. In other embodiments, a recommended therapy may comprise a glucose infusion rate.

In yet other embodiments, such a recommended change in therapy may comprise one or more of the following changes in a recommended therapy:

discontinuing, increasing or decreasing medication associated with hyperglycemia (e.g., corticosteroids or catecholamine vasopresssors);

discontinuing, increasing or decreasing other sources of glucose such as glucose containing fluids (e.g., IV dextrose, nutritional support via feedings, enternal nutrition or total parenteral nutrition); or initiation or cessation of renal replacement therapy (e.g., dialysis, continuous venovenous hemofiltration).

Again, these are merely examples of changes in a recommended therapy that may initiate an alarm according to particular implementations and claimed subject matter is not limited in this respect. Further, such example implementations are not limited to closed-loop systems adapted to infuse glucose or insulin.

Also, as discussed above, such a change in a recommended therapy may be based, at least in part, on blood-glucose sensor measurements taken from the patient. However, such a change in a recommended therapy may be based on other information without deviating from claimed subject matter. For example, such a change in a recommended therapy may be determined based on other factors instead of or in addition to blood-glucose sensor measurements. Such factors may indicate a predisposition for hypoglycemia, for example. Such factors may include one or more of the following predetermined conditions in the patient:

an indication of a diagnosis of sepsis infection;

an APACHE score or other indication of illness based on admission diagnosis;

an indication of diagnosis of organ failure (e.g., liver or renal failure);

an indication of diagnosis of hemodynamic shock;

a history of diabetes mellitus; and any evidence of previous hypoglycemic episodes during hospital stay.

According to an embodiment, a controller in a closed-loop system (e.g., controller 12) may determine a suggested change in the recommended therapy (e.g., increasing or decreasing insulin infusion rate, and infusion of a bolus of glucose) based, at least in part, on subsequent blood-glucose sensor measurements. In other embodiments, such a controller in a closed-loop system may determine such a change based on one or more of the aforementioned predetermined conditions in patient instead of or in addition to such subsequent blood-glucose sensor measurements. In one particular implementation, such predetermined conditions may be indicated by entries to an operator interface to the controller (e.g., provided by an attendant). In another particular implementation, a controller may receive information indicating such predetermined conditions from a remote database that is accessible by the controller over an electronic data communications network.

In response to changes in a recommended therapy, controller 12 may initiate an alarm to an attendant. Such an alarm may comprise, for example, a wireless paging message, email message, phone call, audible noise, vibration of mobile device, visual indication on an infusion device, colored indicator on a display panel, displayed message, just to name a few examples.

In one particular embodiment, the attendant or caretaker may be able to take action to implement and/or enable the suggested change. For example, such an attendant or caretaker may interact with controller 12 to approve the suggested change in recommended therapy. Alternatively, such an attendant or caretaker may manually adjust an infusion rate of glucose or insulin.

In one particular embodiment, controller 12 may determine at least one PID command based, at least in part, on blood-glucose measurements processed in a current command cycle. Then, controller 12 may determine at least one subsequent PID command based, at least in part, on blood-glucose sensor measurements processed in a subsequent command cycle. In a particular implementation, although claimed subject matter is not limited in this respect, controller 12 may detected the suggested change in the recommended therapy based, at least in part, on the subsequent PID command.

In one implementation, as discussed above, the subsequent PID command may comprise a derivative component $U_D$ that is based, at least in part, on values of blood glucose sensor measurements obtained at times separated by a sample interval. Here, the sample interval may be limited to be at least a predetermined minimum sample interval.

In another implementation, as discussed above, the subsequent PID command may comprise an integral component $U_I$ derived, at least in part, by integrating a difference between an estimated current blood glucose level G and a target blood glucose level $G_B$ over an integration level. Here, also as discussed above, the integration interval may be limited to a predetermined maximum integration interval to reduce undue effects to the integral component response for extremely long command cycles.

According to an embodiment, although claimed subject matter is not limited in this respect, a new insulin infusion rate determined for a suggested change in a recommended therapy may be based, at least in part, on a PID command issued from controller 12 for a subsequent command cycle. In a particular implementation, as discussed above, such a new insulin rate may be established for the suggested change in the recommended therapy if a difference between the new insulin rate for the subsequent command cycle and an insulin rate determined for a current command cycle exceeds a threshold difference (e.g., $\Delta\text{Ins}_{rate\ or}"\%\Delta\text{Ins}_{rate}"$).

In another implementation, controller 12 may forecast a blood-glucose level in a patient for a subsequent or future command cycle. Then, controller 12 may determine a suggested change in the recommended therapy commencing in the subsequent command cycle based, at least in part, on the forecasted blood-glucose level. For example, controller 12 may determine a PID command associated with the subsequent command cycle. Controller 12 may then also determine a rate of insulin infusion for the suggested change in recommended therapy based, at least in part, on the PID command if the forecasted blood glucose level exceeds a predetermined threshold blood glucose level $$\left(\text{e.g., } G^{n-1} + \frac{dG}{dt}\Delta t \geq G_{min}\right).$$

As indicated above, a recommended therapy may include infusion of a bolus of glucose. In one embodiment, the size of such a bolus of glucose to be infused in a command cycle may be determined based, at least in part, on a magnitude of at least one PID command from controller 12 associated with a command cycle. In another embodiment, controller 12 may selectively provide such a command for infusion of a bolus of glucose based upon such a PID command for a subsequent command cycle if a blood-glucose level forecasted for the subsequent command cycle does not exceed a threshold blood glucose level. This may prevent hyperglycemia as discussed above.

In another embodiment, an attendant and/or caretaker may be tasked to enter a blood glucose reference value into a controller (e.g., controller 12) from time to time to, among other things, calibrate glucose sensor measurements as discussed below. For example, such an attendant and/or caretaker may obtain blood glucose reference measurements from a patient's blood using glucose test strips. These measurements may then be used to calibrate sensor measurements using techniques such as those described in U.S. Pat. No. 6,895,263. Following entry of glucose reference measurement value, an attendant and/or caretaker may depart and return when alerted to any one of several events (e.g., detected insulin excursions, high blood glucose levels, etc.) as part of a "callback" procedure.

According to an embodiment, although claimed subject matter is not limited in this respect, a controller, such as controller 12, may determine a maximum duration following entry of a blood glucose measurement until initiating an alert to a caretaker and/or attendant as part of a callback procedure. In one particular implementation, such a maximum duration may be determined at a when an attendant enters a blood glucose reference measurement and based upon conditions that exist at that time (e.g., blood-glucose concentration, PID command). Also, it should be understood, however, that a blood glucose measurement is merely an example of a particular measurement that may be entered by an attendant and that other types of measurements may be used without deviating from claimed subject matter.

In particular embodiments, the maximum duration following entry of a measurement and providing a callback alert to an attendant ($\tau_{MD}$) may be determined as a default duration of time in the absence of certain predefined conditions. Also, $\tau_{MD}$ be determined as a duration that is longer or shorter than the default duration of time based, at least in part, on any one of several factors and/or conditions. In one particular implementation, such a maximum duration may be based, at least in part, on an estimated and/or measured rate of change in blood glucose of a patient. Here, this may be determined as $$\left|\frac{dG}{dt}\right|$$

as described above. For example, a particular maximum duration $\tau_{MD}$ may be chosen if $$\left|\frac{dG}{dt}\right|$$

>0.25 mg/dl/min. If $$\left|\frac{dG}{dt}\right| > 0.80\,mg/dl/min,$$

$\tau_{MD}$ may be assigned a shorter duration. Likewise, if $$\left|\frac{dG}{dt}\right| > 1.20\,mg/dl/min,$$

$\tau_{MD}$ may be assigned an even shorter duration. It should be understood, however, that these are merely examples how a rate of change in blood glucose may be used to determine $\tau_{MD}$, and claimed subject matter is not limited in this respect.

In another embodiment, $\tau_{MD}$ may be determined based, at least in part, one or more PID commands determined by a controller. Here, for example, $\tau_{MD}$ may be assigned a particular duration if a PID command based upon current blood glucose sensor measurements changes by at least 0.005 U/Kg/hr and 20%. It should be understood, however, that this is merely an example of how $\tau_{MD}$ may be determined based, at least in part, on a change in a PID command and claimed subject matter is not limited in this respect.

In another embodiment, $\tau_{MD}$ may be determined based, at least in part, on a blood glucose level when the measurement is entered by the caretaker and/or attendant. Here, for example, G<80 mg/dl, $\tau_{MD}$ may be determined as one particular duration. If G>$G_B$+30 mg/dl, $\tau_{MD}$ may be determined as a different particular duration. It should be understood, however, that this is merely an example of how $\tau_{MD}$ may be determined based, at least in part, on a blood-glucose level and claimed subject matter is not limited in this respect.

According to an embodiment, a maximum duration $\tau_{MD}$ following entry of a measurement until a callback alert may be shortened in the presence of particular combinations of events and/or conditions. As discussed above, a controller may determine $\tau_{MD}$ based upon the presence of a particular condition such as blood-glucose level, rate of change in blood-glucose level or PID command. In particular embodiments, such a controller may assign a shorter duration for $\tau_{MD}$ in the presence of multiple conditions. Here, for example, a shorter duration may be assigned to for an "early" callback alert if two more of the following conditions are present in the patient:
 a) at least twenty minutes have elapsed since the previous entry of a blood-glucose reference measurement to a controller;
 b) at least twenty minutes have elapsed since the previous callback alert message;
 c) blood glucose level based upon current $$\frac{dG}{dt}$$

is forecasted to be at or below 60.0 mg/dl within fifteen minutes;
 d) blood glucose level is approaching limits of target blood glucose range (e.g., if estimated blood glucose is within 10.0 mg/dl from a high or low limit of target blood glucose range);
 e) blood glucose level is approaching hypoglycemic or hyperglycemic warning limits (e.g., if estimated blood glucose level is within 10.0 mg/dl from a hypoglycemic limit or within 10.0 mg/dl from a hyperglycemic limit);
 f) a PID command based upon current estimate of blood glucose level has changed by at least 0.01 U/kg/hr and 40%; and
 g) G≤$G_B$+30 mg/dl, and change in PID command by at least 0.005 U/kg/hr and 20%.

In a particular implementation, an callback alert message may be generated as soon as one or more particular conditions are detected. For example, an early callback alert may be issued in the presence of conditions a) and b), in addition to the presence of any of condition c), d) or e). It should be understood, however, that these are merely examples of combinations of two or more conditions that may initiate an early callback alert message being issued to an attendant.

Particular embodiments described above are directed to determining a maximum duration $\tau_{MD}$ following entry of a blood glucose reference measurement by an operator to an operator interface. In other particular implementations, maximum duration $\tau_{MD}$ following entry of other information to an operator interface regarding status of a patient such as, factors indicating a predisposition for hypoglycemia. For example, such factors may include one or more of the following conditions:
 an indication of a diagnosis of sepsis infection;
 an APACHE score or other indication of illness based on admission diagnosis;
 an indication of diagnosis of organ failure (e.g., liver or renal failure);
 an indication of diagnosis of hemodynamic shock;
 a history of diabetes mellitus; and
 evidence of previous hypoglycemic episodes during hospital stay.

In one particular implementation, such status information may be indicated by entries to an operator interface to the controller (e.g., provided by an attendant). In another particular implementation, a controller may receive information indicating such predetermined conditions from a remote database that is accessible by the controller over an electronic data communications network.

System Configuration

The following sections provide exemplary, but not limiting, illustrations of components that may be utilized with the controller described above. Various changes in components, layout of various components, combinations of elements, or the like may be made without departing from the scope of claims subject matter.

Figure 8:
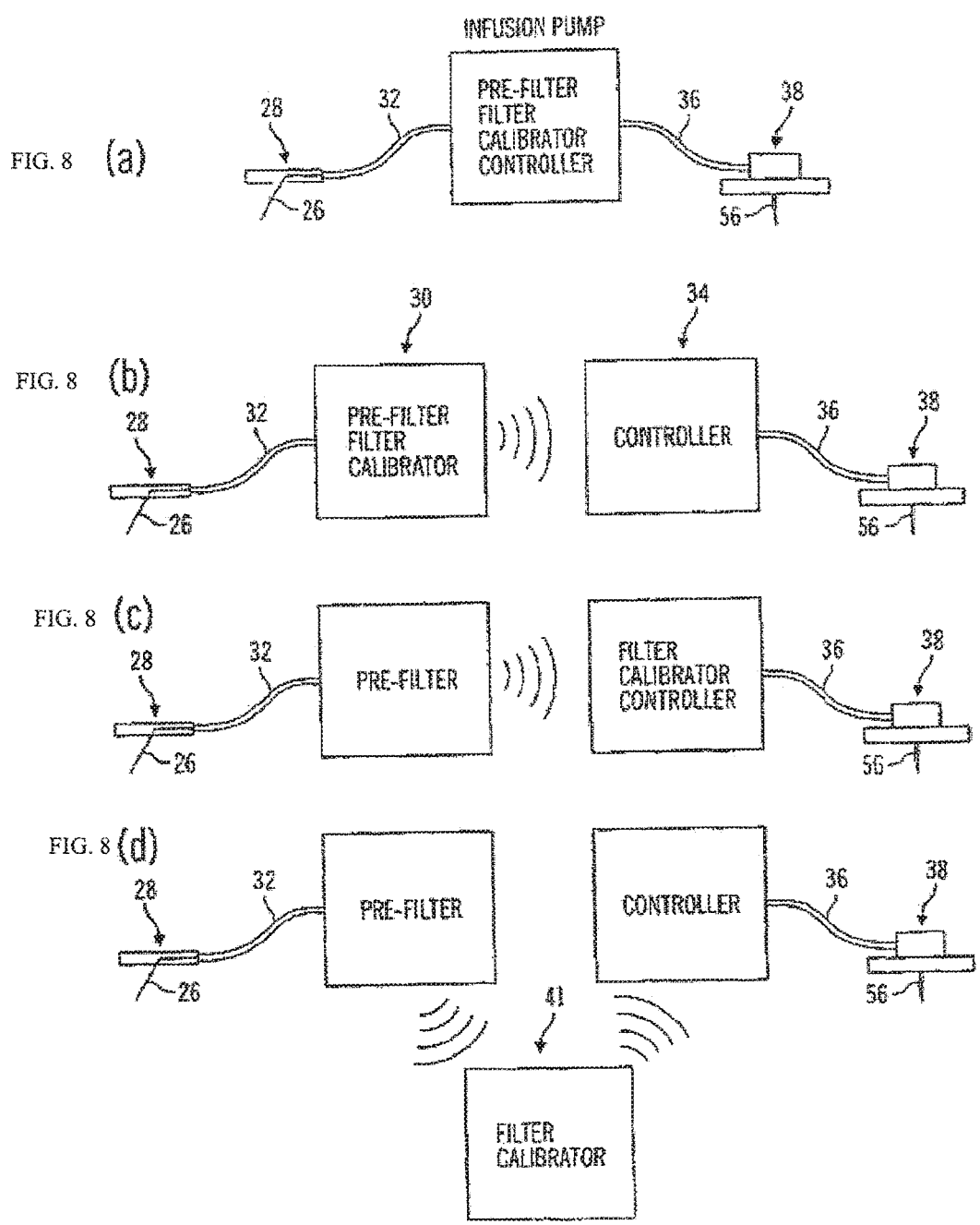
FIG. 8(a) is a diagram of a single device and its components in accordance with an embodiment.
FIG. 8(b) is a diagram of two devices and their components in accordance with an embodiment.
FIG. 8(c) is another diagram of two devices and their components in accordance with an embodiment.
FIG. 8(d) is a diagram of three devices and their components in accordance with an embodiment.
Figure 9A:
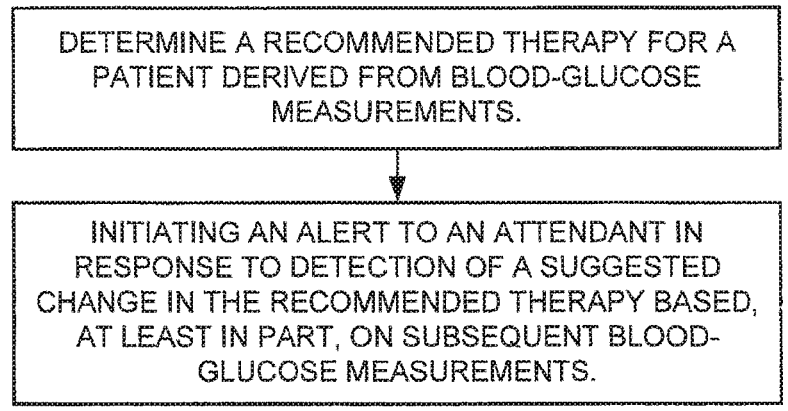
FIGS. 9(a) and 9(b) are flow diagrams illustrating applications of a closed-loop system.
Figure 9B:
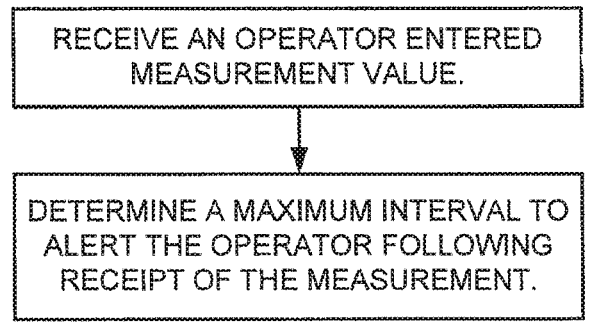

Before it is provided as an input to controller 12, sensor signal 16 may be subjected to signal conditioning such as pre-filtering, filtering, calibrating, and/or the like. Components such as a pre-filter, one or more filters, a calibrator, and the controller 12 may be separately partitioned or physically located together, and may be included with a telemetered characteristic monitor transmitter 30, infusion device 34, or a supplemental device. In particular embodiments, pre-filter, filters and the calibrator are included as part of telemetered characteristic monitor transmitter 30, and controller 20 is included with infusion device 34, as shown in FIG. 8(*b*). In alternative embodiments, a pre-filter may be included with telemetered characteristic monitor transmitter 30 and a filter and calibrator may be included with controller 12 in an infusion device, as shown in FIG. 8(*c*). In other alternative embodiments, a pre-filter may be included with telemetered characteristic monitor transmitter 30, while the filter and calibrator are included in supplemental device 41, and the controller is included in the infusion device, as shown in FIG. 8(*d*).

In particular embodiments, a sensor system generates a message that includes information based on the sensor signal such as digital sensor values, pre-filtered digital sensor values, filtered digital sensor values, calibrated digital sensor values, commands, or the like. Such a message may include other types of information as well such as a serial number, an ID code, a check value, values for other sensed parameters, diagnostic signals, other signals, or the like. In particular embodiments, the digital sensor values Dsig may be filtered in the telemetered characteristic monitor transmitter 30, and then the filtered digital sensor values may be included in the message sent to the infusion device 34 where the filtered digital sensor values are calibrated and used in the controller. In other embodiments, the digital sensor values Dsig may be filtered and calibrated before transmission to the controller 12 in infusion device 34. Alternatively, the digital sensor values Dsig may be filtered, and calibrated and used in the controller to generate commands 22 that are then sent from the telemetered characteristic monitor transmitter 30 to infusion device 34.

In further embodiments, additional optional components, such as a post-calibration filter, a display, a recorder, and a blood glucose meter may be included in the devices with any of the other components or they may stand-alone. Here, if a blood glucose meter is built into one of the devices, it may be co-located in the device that contains the calibrator. In alternative embodiments, one or more of the components are not used.

In particular embodiments, RF telemetry is used to communicate between devices, such as telemetered characteristic monitor transmitter 30 and the infusion device 34, which contain groups of components. In alternative embodiments, other communication mediums may be employed between devices such as wires, cables, IR signals, laser signals, fiber optics, ultrasonic signals, or the like.

Filtering

Figure 16:
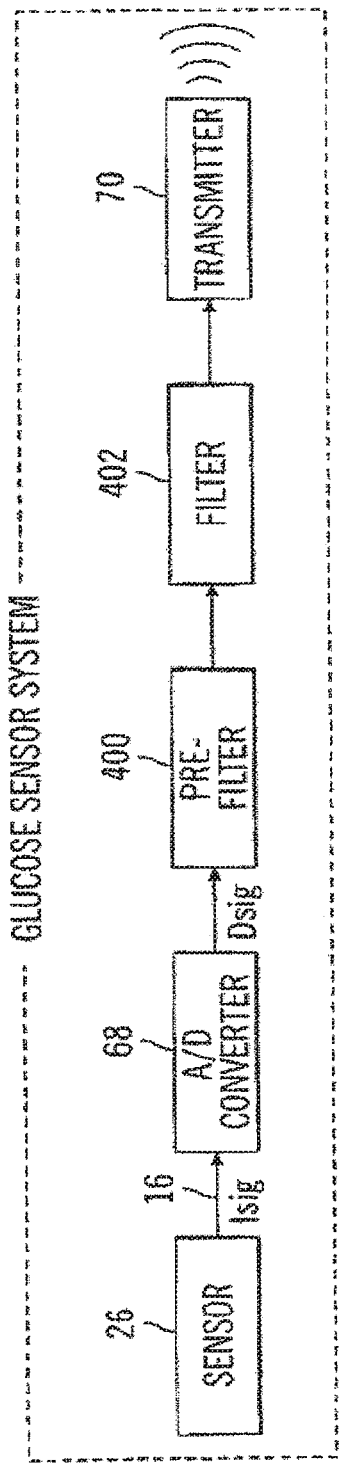
FIG. 16 is a block diagram of the glucose sensor system of FIG. 10 with a pre-filter and a filter in accordance with an embodiment.

In particular embodiments, the digital sensor values Dsig and/or the derivative of the digital sensor values are processed, filtered, modified, analyzed, smoothed, combined, averaged, clipped, scaled, calibrated, or the like, to minimize the effects of anomalous data points before they are provided as an input to the controller. In particular embodiments, the digital sensor values Dsig are passed through a pre-filter 400 and then a filter 402 before they are passed to the transmitter 70, as shown in FIG. 16. The filters are used to detect and minimize the effects of anomalous digital sensor values Dsig. Some causes of anomalous digital sensor values Dsig may include temporary signal transients caused by sensor separation from the subcutaneous tissue, sensor noise, power supply noise, temporary disconnects or shorts, and/or the like. In particular embodiments, individual digital sensor values Dsig may be compared to maximum and minimum value-thresholds. In other particular embodiments, the differences between consecutive pairs of digital sensor values Dsig are compared with rate-of-change-thresholds for increasing or decreasing values.

Pre-Filter

In particular embodiments, the pre-filter 400 uses fuzzy logic to determine whether individual digital sensor values Dsig need to be adjusted. The pre-filter 400 uses a subset of a group of digital sensor values Dsig to calculate a parameter and then uses the parameter to determine whether individual digital sensor values Dsig need to be adjusted in comparison to the group as a whole. For example, the average of a subset of a group of digital sensor values Dsig may be calculated, and then noise thresholds may be placed above and below the average. Then individual digital sensor values Dsig within the group are compared to noise thresholds and eliminated or modified if they are outside of the noise thresholds.

Figure 17:
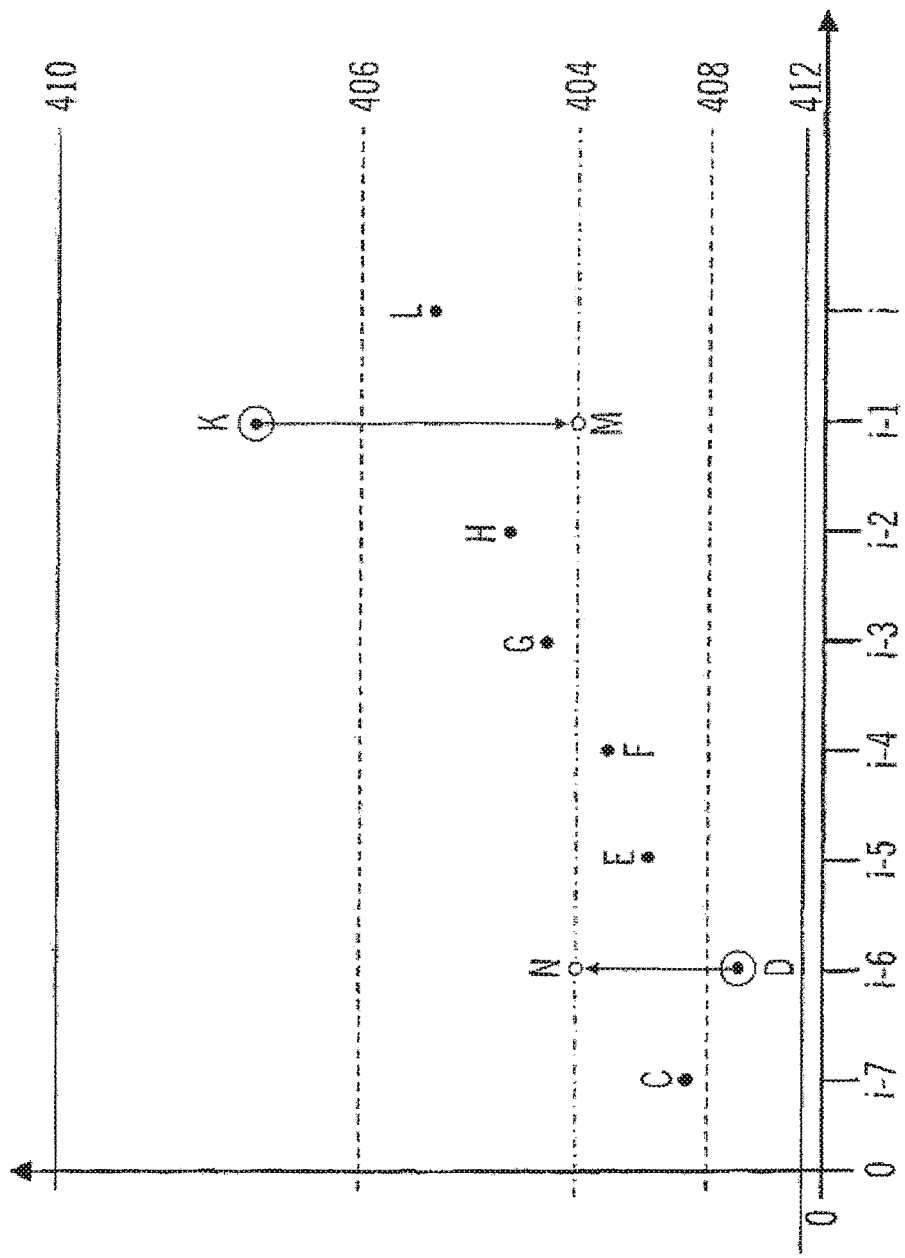
FIG. 17 is a chart of an example of a pre-filter of FIG. 16 and its effects on digital sensor values Dsig in accordance with an embodiment.
Figure 18:
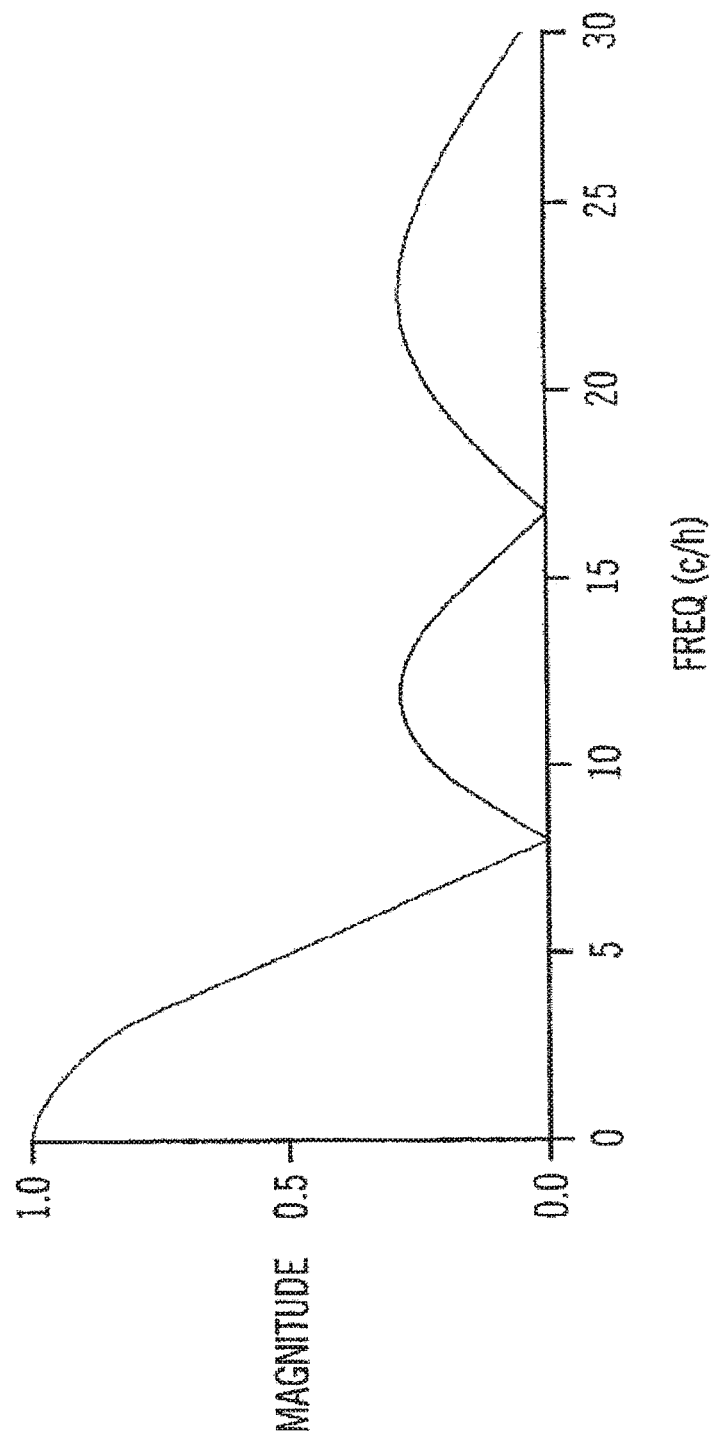
FIG. 18 illustrates a frequency response for a filter of FIG. 17 in accordance with an embodiment.

A more detailed example is provided below to more clearly illustrate, but not limit, an embodiment of a pre-filter. A group of eight digital sensor values Dsig are shown in FIG. 17 including a most recently sampled value, labeled L, sampled from the analog sensor signal Isig at time i, and the seven previous values K, H, G, F, E, D, and C sampled at times (i−1) through (i−7). An average value is calculated using the four temporally middle values in the group, H, G, F, and E sampled at times (i−2) through (i−5). The calculated average value is represented as a dashed/dotted average line 404. A high noise threshold 406 is established at 100% above the average line 404. In other words, the magnitude of the high noise threshold 406 is two times the magnitude of the average line 404. A negative noise threshold 408 is established at 50% below the average line 404. In other words, the magnitude of the negative noise threshold 408 is one-half of the magnitude of the average line 404. The individual magnitudes of each of the eight values, L, K, H, G, F, E, D, and C are compared to the high and negative noise thresholds 406 and 408. If a value is above the high noise threshold 406 or below the negative noise threshold 408 then the value is considered anomalous and the anomalous value is replaced with the magnitude of the average line 404. In the example shown in FIG. 17, the value K is above the high noise threshold 406 so it is replaced with the average value M. Also, the value D is below the negative noise threshold 408 so it is replaced with the average value N. In this way noisy signal spikes are reduced. Therefore, in the example, values L, K, H, G, F, E, D, and C are inputs to the pre-filter 400 and values L, M, H, G, F, E, N, and C are outputs from the pre-filter 400. In alternative embodiments, other noise threshold levels (or percentages) may be used. In other alternative embodiments, values outside of the thresholds may be replaced with values other than the average value, such as the previous value, the value of the closest threshold, a value calculated by extrapolating a trend line through previous data, a value that is calculated by interpolation between other values that are inside the thresholds, or the like.

In particular embodiments, if any of a group's values are outside of the noise thresholds 406 or 408 then a warning flag may be set. If one to three values are outside of the noise thresholds 406 or 408, a 'noise' flag may be set. If more than three values are outside of the noise thresholds 406 or 408, a 'discard' flag may be set which indicates that the whole group of values should be ignored and not used. In alternative embodiments, more or less values need be outside of the thresholds 406 or 408 to trigger the 'noise' flag or the 'discard' flag.

In particular embodiments, each digital sensor value Dsig may be checked for saturation and disconnection. To continue with the example of FIG. 17, each individual value is compared to a saturation threshold 410. If a value is equal to or above the saturation threshold 410 then a 'saturation' flag is set. In particular embodiments, if the 'saturation' flag is set, a warning may be provided to the user that a sensor may need calibration or replacement. In further particular embodiments, if an individual digital sensor value Dsig is at or above saturation threshold 410, individual digital sensor value Dsig may be ignored, changed to a value equal to average line 404, or the entire group of values associated with the individual digital sensor value Dsig may be ignored. In particular embodiments, saturation threshold 410 may be set at about 16% below a maximum value of the range of digital sensor values that may be generated. In particular embodiments, a maximum digital sensor value represents a glucose concentration greater than 150 mg/dl. In alternative embodiments, a maximum digital sensor value may represent larger or smaller a glucose concentrations depending on a range of expected glucose concentrations to be measured, sensor accuracy, sensor system resolution needed for a particular application (e.g., closed loop control), and/or the like. The full range of values is the difference between the maximum and the minimum digital sensor value that may be generated. Higher or lower saturation threshold levels may be used depending on an expected signal range of the sensor, sensor noise, sensor gains, or the like.

Similarly, in particular embodiments, if a digital signal value Dsig is below a disconnect threshold 412, then a 'disconnect' flag may be set indicating to a user that the sensor is not properly connected to the power supply and that the power supply or sensor may need replacement or recalibration. In further particular embodiments, if a digital sensor value Dsig is below the disconnect threshold 412, the individual value may be ignored, changed to a value equal to the average line 404, or the entire group of values associated with the individual digital sensor value Dsig may be ignored. In particular embodiments, disconnect threshold 410 may be set at about 20% of the full range of values. Higher or lower disconnect threshold levels may be used depending on an expected signal range of the sensor, sensor system noise, sensor gains, or the like.

In alternative embodiments, other methods may be used to pre-filter the digital sensor values Dsig such as rate-of-change thresholds, rate-of-change squared thresholds, noise thresholds about a least squares fit line rather than about the average of a subset of a group's values, higher or lower noise threshold lines, or the like.

Noise Filter

After the digital sensor values Dsig are evaluated, and if necessary, modified by the pre-filter 400, the digital sensor values Dsig are passed to the filter 402. The filter 402 may be used to reduce noise in particular frequency bands. A body's blood glucose level 18 may change relatively slowly compared to a rate at which digital sensor values Dsig are collected. Therefore, high frequency signal components may comprise noise, and a low pass filter may be used to improve the signal to noise ratio.

Delay Compensation Filter

Aside from noise reduction, a filter may used to compensate for time delays. Ideally, a sensor would provide a real time, noise-free measurement of a parameter that a control system is intended to control, such as a blood glucose measurement. However, realistically there are physiological, chemical, electrical, and algorithmic sources of time delays that cause the sensor measurement to lag behind the present value of blood glucose. Also, as pointed out above, such a delay may arise from a particular level of noise filtering applied to a sensor signal.

In a particular implementation, as shown in FIG. 20, a physiological delay may arise from the time required for glucose to move between blood plasma 420 and interstitial fluid (ISF). The delay is represented by the circled double-headed arrow 422 in FIG. 20. As discussed above, a sensor may be inserted into the subcutaneous tissue 44 of the body 20 and electrodes 42 near the tip of sensor 40 are in contact with interstitial fluid (ISF). But a desired parameter to be measured includes a concentration of blood glucose. Glucose is carried throughout the body in blood plasma 420. Through the process of diffusion, glucose may move from the blood plasma 420 into the ISF of subcutaneous tissue 44 and vice versa. As blood glucose level 18 changes so does the glucose level in the ISF. But the glucose level in the ISF may lag behind the blood glucose level 18 due to the time required for the body to achieve glucose concentration equilibrium between the blood plasma 420 and the ISF. Studies show the glucose lag times between blood plasma 420 and ISF may vary between 0.0 to 30.0 minutes. Some parameters that may affect such a glucose lag time between blood plasma 420 and ISF are the individual's metabolism, the current blood glucose level, whether the glucose level is rising, or falling, or the like.

A chemical reaction delay 424 may be introduced by the sensor response time, represented by the circle 424 surrounding the tip of the sensor 26 in FIG. 20. Sensor electrodes 42 may be coated with protective membranes that keep the electrodes 42 wetted with ISF, attenuate the glucose concentration, and reduce glucose concentration fluctuations on the electrode surface. As glucose levels change, the protective membranes may slow the rate of glucose exchange between the ISF and the electrode surface. In addition, there is a chemical reaction delay simply due to the reaction time for glucose to react with glucose oxidase GOX to generate hydrogen peroxide, and the reaction time for a secondary reaction, the reduction of hydrogen peroxide to water, oxygen and free electrons.

As discussed above, there may also be a processing delay as the analog sensor signal Isig is converted to digital sensor values Dsig. In particular embodiments, an analog sensor signal Isig may be integrated over one-minute intervals and then converted to a number of counts. In essence an A/D conversion time may result in an average delay of 30 seconds. In particular embodiments, the one-minute values may be averaged into 5-minute values before they are provided to controller 12. A resulting average delay may then be two and one half minutes. In alternative embodiments, longer or shorter integration times may be used resulting in longer or shorter delay times. In other embodiments the analog sensor signal current Isig is continuously converted to an analog voltage Vsig and a A/D converter samples the voltage Vsig every 10 seconds. Then six 10-second values are pre-filtered and averaged to create a one-minute value. Finally, five one-minute values may be filtered and then averaged creating a five-minute value resulting in an average delay of two and one half minutes. Other embodiments use other electrical components or other sampling rates and result in other delay periods.

Again, as pointed out above, filters may also introduce a delay due to the time required to acquire a sufficient number of digital sensor values Dsig to operate a digital filter. Higher order filters, by definition, require more digital sensor values Dsig. Aside from the most recent digital sensor value Dsig, FIR filters use a number of previous values equal to the order of the filter. For example, a 7th order filter uses 8 digital sensor values Dsig. There is a time interval between each digital sensor value Dsig. To continue with the example, if the time interval between digital sensor values Dsig is one minute, then the oldest digital sensor value Dsig used in a 7th order FIR filter would be seven minutes old. Therefore, the average time delay for all of the values used in the filter is three and a half minutes. However, if the weighting factors associated with each of the values are not equal then the time delay may be longer or shorter than three and one half minutes depending on the effects of the coefficients.

Figure 21:
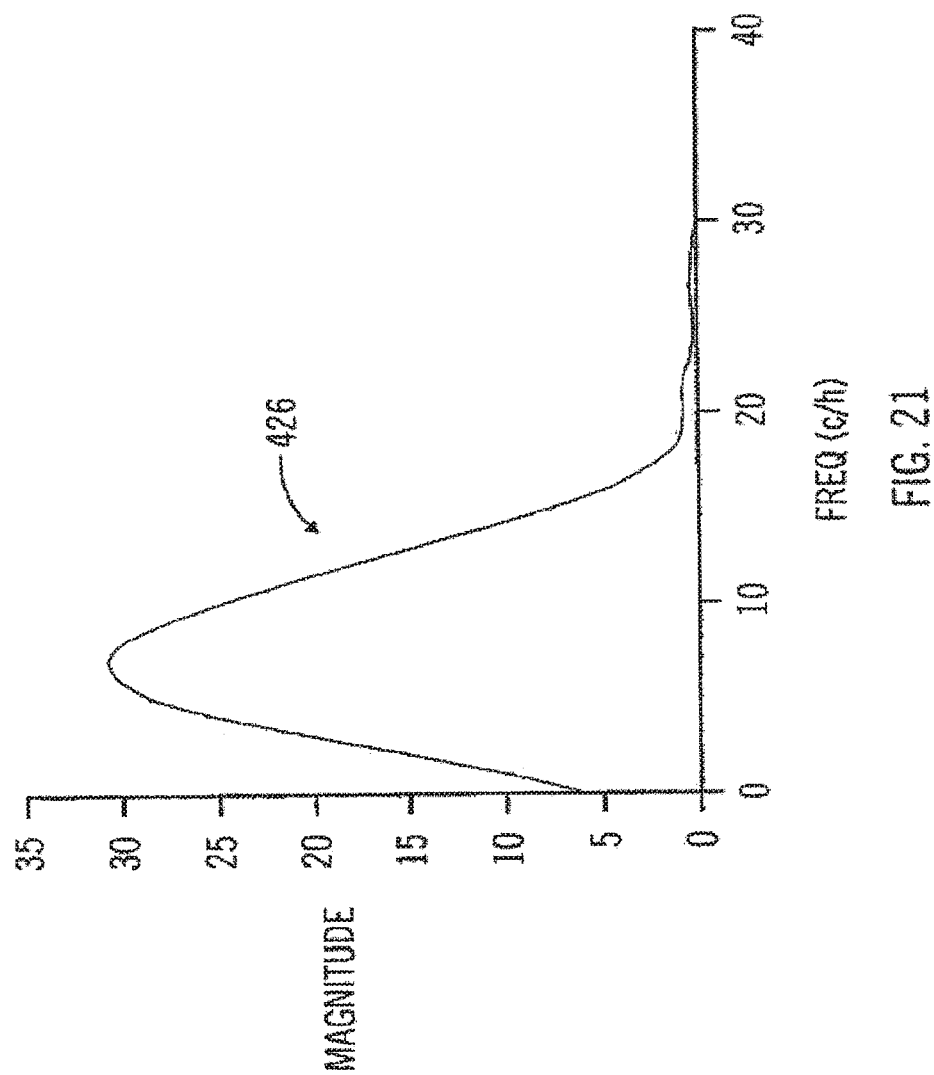
FIG. 21 is a plot showing a frequency response of a time delay correcting Weiner filter in accordance with an embodiment.
Figure 22:
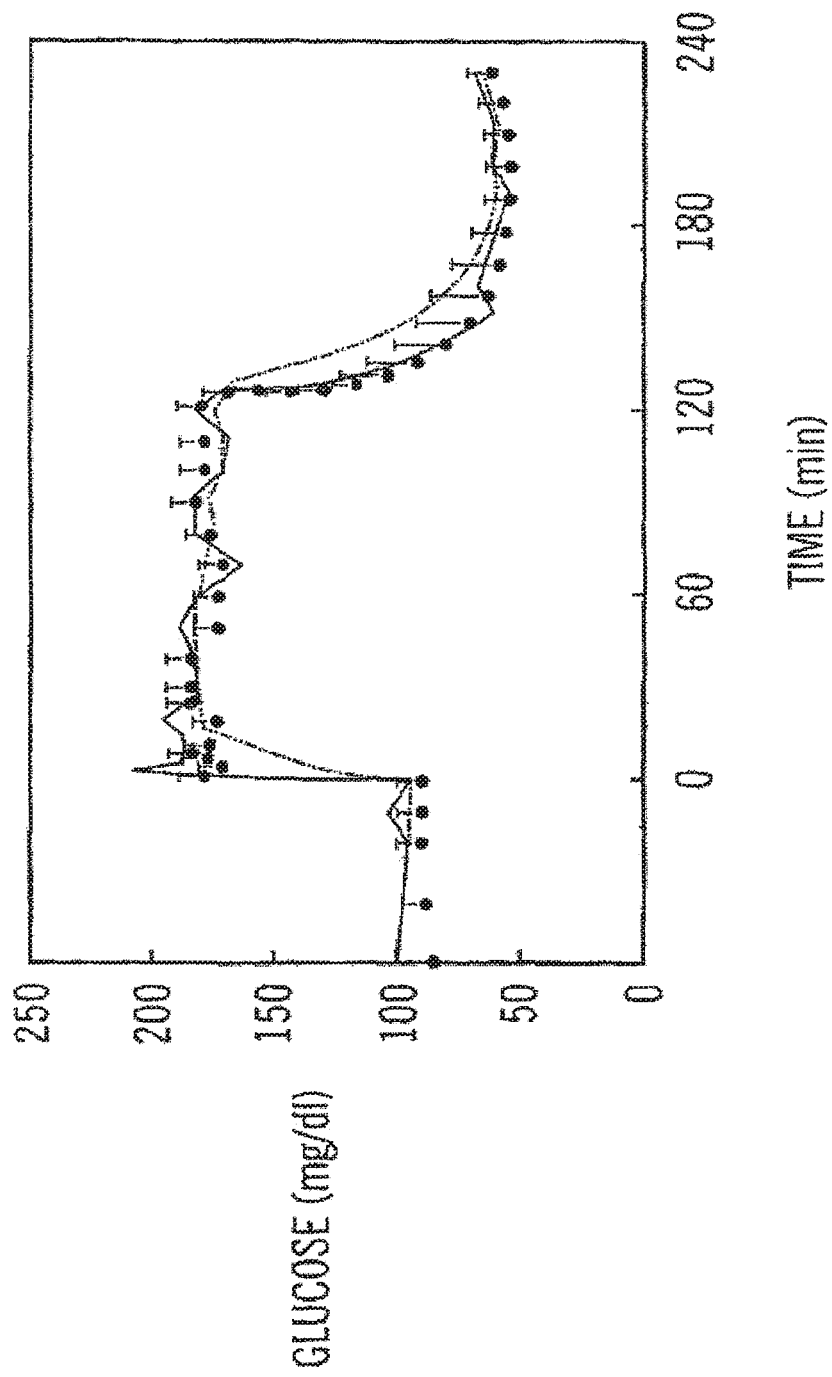
FIG. 22 is a plot of a digital sensor values Dsig before and after time delay correction compared to actual glucose measurements over time in accordance with an embodiment.

Particular embodiments may include a FIR filter that compensates for both the various time delays, of up to about 30 minutes as discussed above, and high frequency noise, greater than about 10 c/hr also discussed above. Particular embodiments employ a $7^{th}$ order Weiner type FIR filter. The coefficients for the filter may be selected to correct for time lags while simultaneously reducing high frequency noise. An example of a frequency response curve 426 is shown in FIG. 21. The example frequency response curve 426 is generated for a Weiner filter with a pass band for frequencies from zero up to about 8 c/hr and a stop band for frequencies greater than about 15 c/hr for a sensor with a sensitivity of about 20 µA/100 mg/dl.

In alternative embodiments, other types of filters may be used. In other alternative embodiments, no time compensation is used if a rate of change in the blood glucose level is slow compared to the time delay. For example, a five-minute delay between blood plasma glucose and a sensor measurement does not have to be corrected for a closed loop glucose control system to function.

Calibration

In particular embodiments, after filtering, digital sensor values Dsig may be calibrated with respect to one or more blood-glucose reference sample values. Such blood-glucose reference sample values may be entered into a calibrator for comparison with digital sensor values Dsig (e.g., by an attendant or caretaker as discussed above). Such a calibrator may apply a calibration process to convert the digital sensor values Dsig, which may be in counts into blood-glucose measurement values. In particular embodiments, the calibration method is of the type described in U.S. Pat. No. 6,424,847 or 6,895,263. In particular embodiments, a calibrator may be included as part of the infusion device 34 and glucose reference values may be entered by an operator into the infusion device 34. In other embodiments, glucose reference values may be entered into the telemetered characteristic monitor transmitter 30 while a calibrator calibrates the digital sensor values Dsig and transmits calibrated digital sensor values to infusion device 34. In further embodiments, glucose reference values may be entered into a supplemental device where calibration is executed. In alternative embodiments, a blood glucose meter is in communication with the infusion device 34, telemetered characteristic monitor transmitter 30 or supplemental device so that glucose reference values may be transmitted directly into device that the blood glucose meter may be in communication with. In additional alternative embodiments, a blood glucose meter is part of the infusion device 34, telemetered characteristic monitor transmitter 30 or supplemental device such as that shown in U.S. patent application Ser. No. 09/334,996, filed on Jun. 17, 1999, entitled "CHARACTERISTIC MONITOR WITH A CHARACTERISTIC METER AND METHOD OF USING THE SAME".

In particular embodiments, to obtain blood glucose reference values, one or more blood samples may be extracted from body 20, and a common, over-the-counter, blood glucose meter may be used to measure blood plasma glucose concentration of the samples. Then a digital sensor value Dsig may be compared to the blood glucose measurement from the meter and a mathematical correction is applied to convert the digital sensor values Dsig to blood glucose measurement values. In alternative embodiments, a solution of a known glucose concentration is introduced into the subcutaneous tissue surrounding the sensor 26 by using methods and apparatus such as described in U.S. Pat. No. 6,254,586, or by using injection, infusion, jet pressure, introduction through a lumen, or the like. A digital sensor value Dsig is collected while the sensor 26 is bathed in the solution of known glucose concentration. A mathematical formula such as a factor, an offset, an equation, and/or the like, is derived to convert the digital sensor value Dsig to the known glucose concentration. A mathematical formula is then applied to subsequent digital sensors values Dsig to obtain blood glucose measurement values. In alternative embodiments, the digital sensor values Dsig may be calibrated before filtering. In additional alternative embodiments, the digital sensor values Dsig may be calibrated after pre-filtering and before filtering. In other alternative embodiments, sensors are calibrated before they are used in the body or do not require calibration at all.

According to an embodiment, blood-glucose reference sample values are paired in time with valid values of Dsig to form a function to determine measurements of blood-glucose concentration based on Dsig. Once paired calibration data is available, the appropriate calibration process may be applied dependent on how many paired calibration data points are available since the last calibration, the total period of time that glucose sensor system 10 has been in use, and the number of times glucose sensor system 10 has been calibrated.

As pointed out above according to particular embodiments, blood glucose reference sample values may be entered into controller 12 periodically through out each day of use. Here, calibration may be conducted immediately after the initialization/stabilization of glucose sensor system 10 and once a day thereafter. However, such calibration may be conducted more or less often depending on whether glucose sensor system 10 has been replaced, whether a calibration cancellation event has occurred, the stability of glucose sensor system 10 sensitivity over time, and/or the like.

In particular embodiments, blood-glucose reference sample values are collected several times per day but a new calibration factor is calculated only once per day. Therefore, typically more than one paired calibration data point is collected between calibrations. In alternative embodiments, the glucose monitor is calibrated every time a new paired calibration data point is collected.

Figure 43:
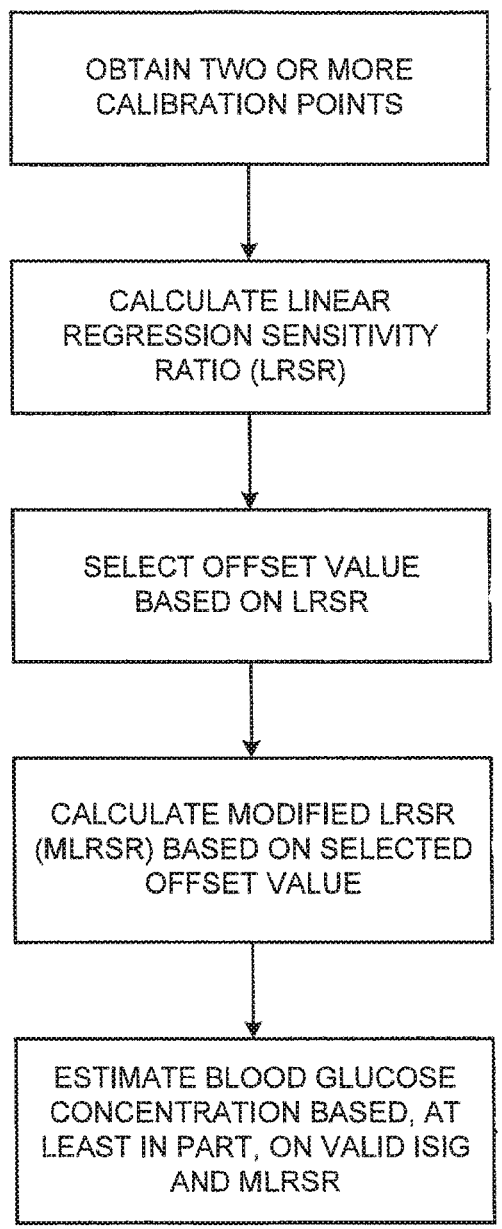

According to an embodiment, a single-point pair of a blood-glucose reference sample value and Dsig value may be used to calculate a sensitivity ratio (SR), such as immediately after initialization/stabilization. A modified linear regression technique (shown in a block diagram in FIG. 43) may be used if two or more paired calibration data points are available. Particular embodiments may use a single-point calibration technique whether or not more than one paired calibration data point is available.

Figure 42:
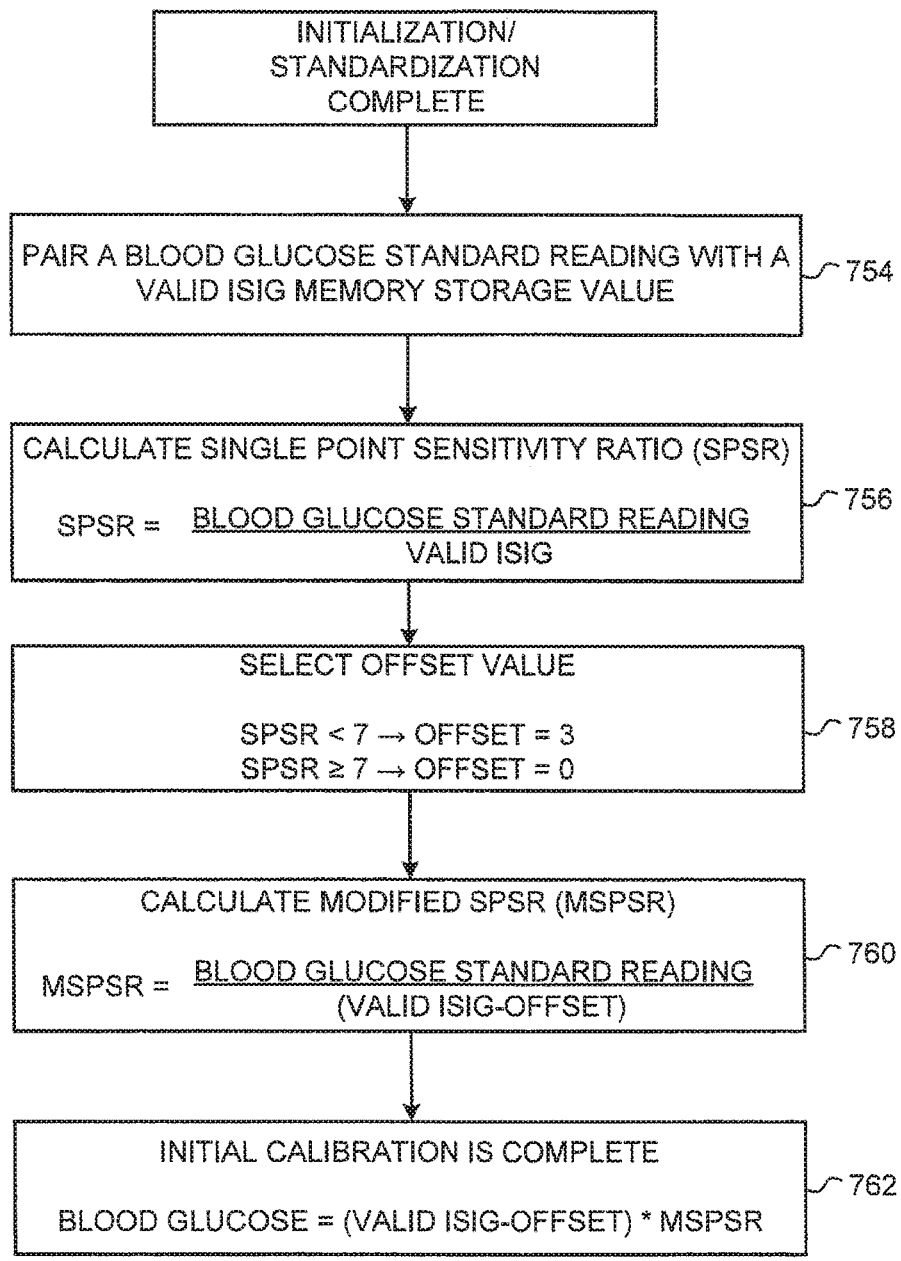
FIGS. 42 and 43 are flow diagrams illustrating processes for calibrating a glucose sense according to an embodiment.

A single-point calibration equation may be based on an assumption that a valid Dsig value will be 0 when the blood glucose is 0. Here, a single paired non-zero calibration point may be used with the point (0,0) to establish a linear function. The slope of the linear function from the origin (0,0) and passing through the single paired calibration point provides a single-point sensitivity ratio (SPSR). As shown in the process FIG. 42, a single paired calibration point obtained at block 754 is used with the point (0,0) to establish a line or linear function. The slope of the line from the origin (0,0) and passing through the single paired calibration point provides a single-point sensitivity ratio (SPSR). Here, block 756 may calculate such an SPSR as follows:

$$SPSR = \frac{\text{Blood Glucose Reference Reading}}{\text{Valid } ISIG}$$

Therefore, the calibrated blood glucose level may be expressed as follows:

Blood Glucose Level=Valid Dsig*SPSR

As an example, using values of 20.1 Nano-Amps and 102 mg/dl as a paired calibration data point, calculation of SPSR may be expressed as follows:

SPSR=102/20.1=5.07 mg/dl per Nano-Amp

To continue with the current example, once calibration is complete, given a glucose sensor reading of 15.0 Nano-Amps, calculated blood glucose level may be determined as follows:

Blood Glucose Level=15.0*5.07=76.1 mg/dl

Additionally, particular embodiments may use an offset value in a calibration equation to compensate for the observation that more sensitive glucose sensor system 10 (e.g., generating higher Dsig values compared to other glucose sensor systems at the same blood glucose level, which result in lower SR values) may have a less linear performance at very high blood glucose levels in comparison to glucose sensor systems with lower sensitivity (and therefore relatively higher SR values). If the SPSR for a particular glucose sensor system 10, as calculated above, is less than a sensitivity threshold value, then a modified SPSR (MSPSR) may be calculated at block 760 using an offset value selected at block 758. In one particular implementation, the threshold value is 7. If the initial calculation of the SPSR (shown above) is less than 7, for example, an offset value of 3 may be used to calculate the MSPSR. If the initial calculation of SPSR yields a value of 7 or greater, then the offset value may be 0. Thus, the MSPSR may be calculated at block 760 using the offset value according to a modified single-point calibration expression, as follows:

$$MSPSR = \frac{\text{Blood Glucose Reference Reading}}{\text{Valid } Dsig - \text{offset}}$$

Accordingly, an initial calibration of glucose sensor system 10 may be used to estimate a blood glucose from a sensor measurement at block 762 as follows:

Blood Glucose Level=(Valid Dsig−offset)*MSPSR

Continuing the above example since the SPSR is 5.07, which is less than 7, the sensitivity ratio is recalculated using the MSPSR equation as:

MSPSR=102/(20.1−3)=5.96 mg/dl per Nano-Amp

Given a glucose sensor reading of 15.0 Nano-Amps after calibration, the calculated blood glucose may be expressed as follows:

Blood Glucose Level=(15.0−3)=5.96=71.5 mg/dl

In another example, given a blood glucose reference reading of 95 from a typical blood glucose meter and a Dsig value of 22.1, a resulting SPSR may be determined as 95/22.1=4.3. Since SR<7, the offset=3. Therefore, the MSPSR is 95/[22.1−3]≈5.0. Note that if the SPSR is greater than or equal to 7 the offset value is 0 and therefore the MSPSR=SPSR.

In alternative embodiments, the offset value may be eliminated from the expression for calculating the blood glucose value as follows:

Blood Glucose Level=Valid Dsig*MSPSR

The threshold value of 7 and the associated offset of 3 have been empirically selected based on the characteristics observed from testing a particular type of glucose sensor systems, such as those described in U.S. Pat. No. 5,391,250 entitled "Method of Fabricating Thin Film Sensors", and U.S. Pat. No. 6,360,888. Other threshold values may be used in conjunction with other offset values to optimize the accuracy of the calculated MSPSR for various types of glucose sensor systems and sensors used to detect other body characteristics. In fact, many threshold values may be used to select between many offset values. An example using two different threshold values (4 and 7) to select between three different offset values (5, 3 and 0) follows:

if SPSR<4, offset=5;
if 4≤SPSR<7, offset=3; and
if SPSR≥7, offset=0.

In particular embodiments an MSPSR may be compared to a valid sensitivity range to determine whether a newly calculated MSPSR is reasonable. In order to identify potential system problems, a valid MSPSR range of 1.5 to 15 may be employed, for example. However this is merely an example of such a range and claimed subject matter is not limited in this respect. This range may be determined based, at least in part, upon valid glucose sensor sensitivity measurements made in-vitro. MSPSR values outside this range may result in a calibration error alarm to notify the user of a potential problem. Other valid sensitivity ranges may be applied depending on the types of sensors to be calibrated, the range of acceptable sensitivity levels for the various sensor types, the manufacturing consistency expected for the sensors, environmental conditions, how long the sensor has been in use, and/or the like.

Particular embodiments may augment the above described single-point calibration technique using a modified linear regression technique (shown in a block diagram in FIG. 43) if more than one paired calibration data point is available. Here, paired calibration data points may be linearly regressed by a least squares method to calculate a best fit straight line correlated with paired calibration data points. The slope of the line resulting from the linear regression may be the linear regression sensitivity ratio (LRSR) used as the calibration factor to calibrate glucose sensor system 10. As such, a blood-glucose concentration may be estimated as follows:

Blood Glucose Level=(Valid Dsig−offset)*LRSR.

As pointed out above, a blood-glucose concentration may be estimated as a linear function of Dsig, where either LRSR or MSPSR provide the slope of such a function. Accordingly, a value for "offset" may determine a y-intercept of such a linear function (e.g., where y-intercept is expressed as "offset" or offset*LRSR). In particular implementations, such a y-intercept may be selected as a computed value (as described above) or as a predetermined constant based upon one or more conditions and/or events.

As discussed above, according to an embodiment, a y-intercept may be selected as, as discussed above, as a value computed based, at least in part, on a relationship between at least one blood-glucose reference measurement value and at least one sensor signal value Dsig. However, such selection of a computed value may be conditioned on whether such a computed value would be reliably accurate. In one example, a computed value may be selected if a minimum number of glucose reference samples have been obtained following initialization of glucose sensor system 10. In another example, selection of a computed value as a y-intercept may be conditioned attributes of blood-glucose measurements entered and/or collected (e.g., by a caretaker or attendant). For example, selection of a computed value as a y-intercept may be conditioned on one or more of the following:

a. at least one of the blood-glucose reference sample values is in a range of about 80.0 to 150.0 mg/dl;
b. a correlation of blood-glucose reference sample values is at least 0.9; or
c. the difference between maximum and minimum blood-glucose reference sample values is at least 50 ml/dl and at least 50% of the minimum blood-glucose reference sample values.

In one particular implementation, in selecting pairs of blood-glucose sensor measurements (Dsig) and blood-glucose reference sample values certain pairs may be discarded and/or filtered out in computing a regression function as illustrated above. For example, such pairs may be discarded by computing a Cook's Distance. Here, in one particular example, if Cook's Distance for a pair is more than 50% of Snedecor's F Distribution F(p, N−p), with p=2 (the number of regression carriers) and N=the number of points, the pair may be discarded.

Sensor Signal Processing Systems

Figure 10:
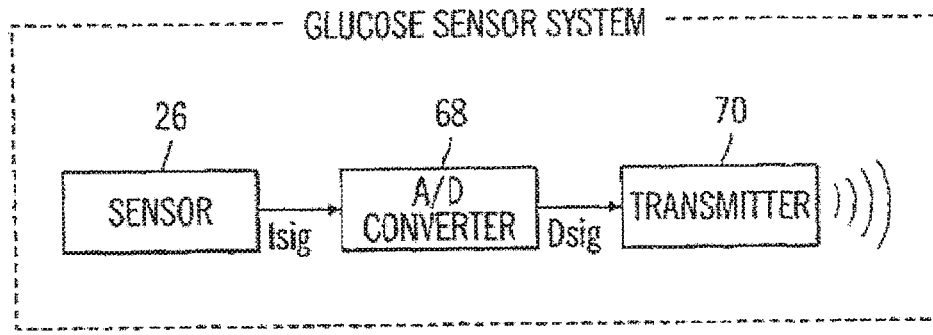
FIG. 10 is a schematic block diagram of a glucose sensor system according to an embodiment.
Figure 11:
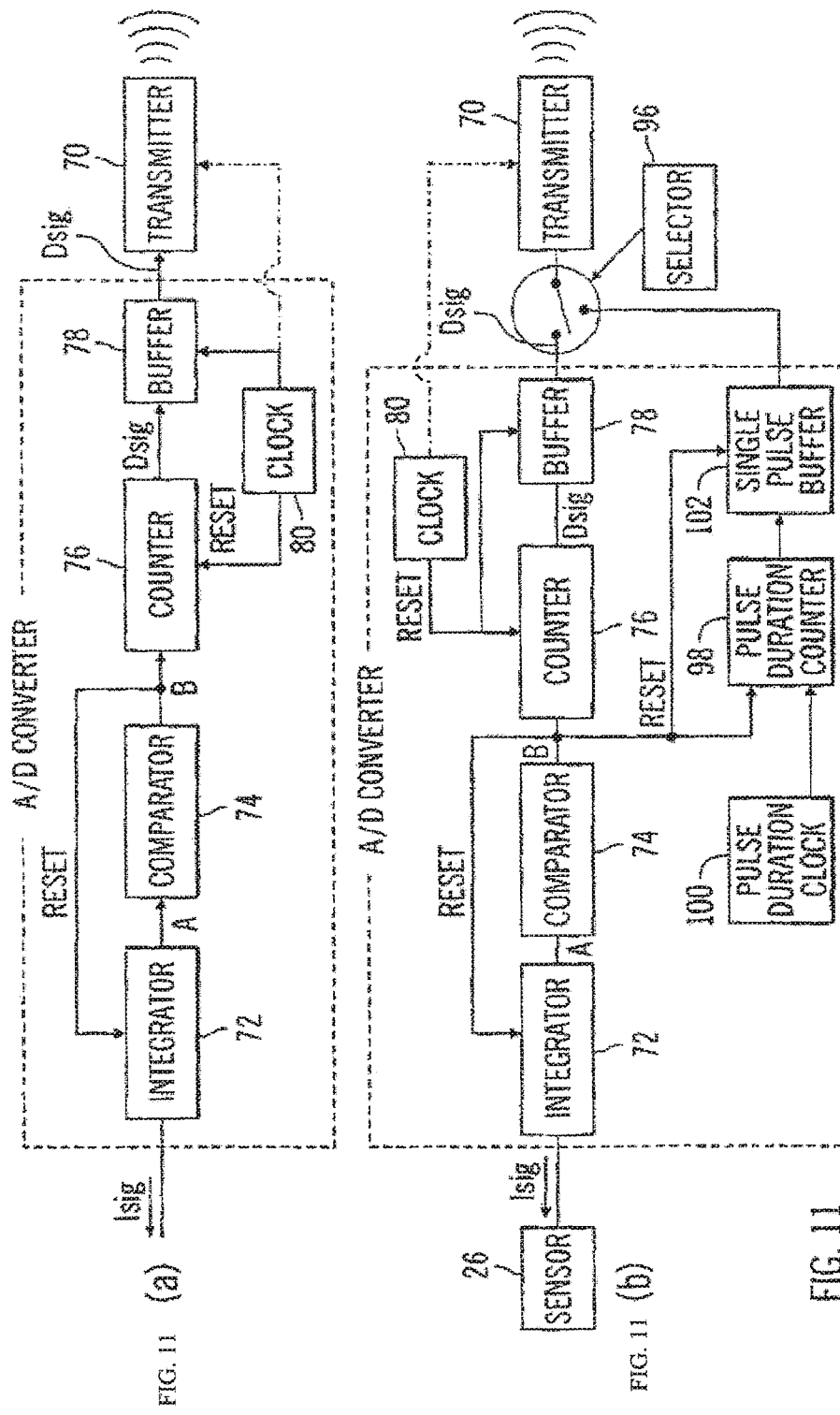
FIG. 11(a) is a schematic block diagram of an A/D converter for the glucose sensor system of FIG. 10 in accordance with an embodiment.
FIG. 11(b) is a schematic block diagram of the A/D converter for the glucose sensor system of FIG. 10 with a pulse duration output selection option in accordance with an embodiment.

Before filtering and calibrating, generally the sensor signal is processed to convert the sensor signal from a raw form into a form acceptable for use in the filters and/or calibrator. In particular embodiments, as shown in FIG. 10, an analog sensor signal Isig is digitally quantified through an A/D converter 68 resulting in digital sensor values Dsig that are transmitted by a transmitter 70 from the telemetered characteristic monitor transmitter 30 to another device. In particular embodiments, the analog sensor signal Isig is an analog current value that is converted to a digital sensor value Dsig in the form of a digital frequency measurement, as shown in FIG. 11(a). Here, such circuitry may include an integrator 72, a comparator 74, a counter 76, a buffer 78, a clock 80, and the transmitter 70. The integrator 72 generates a substantially ramped voltage signal (A), and the instantaneous slope of the ramped voltage signal is proportional to the magnitude of the instantaneous analog sensor signal Isig. Comparator 74 converts the ramped voltage signal (A) from the integrator 72 into square wave pulses (B). Pulses from the comparator 74 increment counter 76 and also reset integrator 72. Clock 80 periodically triggers buffer 78 to store a present value from counter 76, and then reset counter 76. Values stored in buffer 78 include the digital sensor values Dsig. Clock 80 may also periodically signal transmitter 70 to send a value from buffer 78. In particular embodiments, a clock period is one minute. However, in alternative embodiments, such a clock period may be adjusted based on how often measurements are needed, sensor signal noise, sensor sensitivity, desired measurement resolution, the type of signal to be transmitted, or the like. In alternative embodiments, a buffer is not used.

A/D Converters

Various A/D converter designs may be used in particular embodiments. The following examples are illustrative, and not limiting, since other A/D converters may be used.

I to F (Current to Frequency (Counts)), Single Capacitor, Quick Discharge

In particular embodiments, integrator 72 consists of a first Op-Amp 92 and a capacitor 82, shown in FIG. 10. Integrator 72 sums the analog sensor signal Isig current by charging the capacitor 82 until the capacitor voltage (A') achieves a high reference voltage (Vref$_H$). Capacitor voltage (A') is measured at the output of first Op-Amp 92. A second Op-Amp 94 is used as a comparator. If the capacitor voltage (A') reaches Vref$_H$, the comparator output (B') changes from low to high. The high comparator output (B') closes a reset switch 84 that discharges capacitor 82 through a voltage source (V+). High comparator output (B') also triggers a reference voltage switch 88 to close, while substantially simultaneously an inverter 86 inverts the comparator output (B'). And the inverter output (C') triggers a reference voltage switch 90 to open. The result is that the reference voltage of the comparator is changed from Vref$_H$ to the low reference voltage (Vref$_L$).

When the capacitor voltage (A') is discharged to Vref$_L$, the comparator output (B') returns to low, thus forming a pulse. The low comparator output (B') opens the reset switch 84 allowing the capacitor 82 to begin charging again.

Virtually simultaneously, the low comparator output (B') may also triggers the reference voltage switch 88 to open and the inverter output (C') may trigger reference voltage switch 90 to close resulting in changing the comparator reference voltage from Vref$_L$ back to Vref$_H$.

I to F, Single Reversible Capacitor

In alternative embodiments, two or more integrator switches may be used to control the polarity of one or more capacitors. A particular embodiment is shown in FIG. 13. Here, only one of the two integrator-switches 110 and 112 may be closed and the other integrator switch is open. If the first integrator switch 110 is closed, second integrator switch 112 may be open and an integrator Op-Amp 114 may sum the analog sensor signal Isig current by charging a capacitor 116 until the capacitor voltage (A") achieves a high reference voltage (Vref$_H$). Comparator 120 may compare integrator output (A") to reference voltage Vref$_H$. If the capacitor voltage (A") reaches Vref$_H$, the comparator output (B") shifts from low to high, initiating a pulse.

High comparator output (B") pulse may cause the capacitor polarity to reverse using the following method. High comparator output (B") triggers the second integrator switch 112 to close while virtually simultaneously inverter 118 inverts comparator output (B"). And the low inverter output (C") pulse triggers first integrator switch 110 to open. Once the capacitor's polarity is reversed, capacitor 116 discharges at a rate proportional to the analog sensor signal Isig. The high comparator output (B") pulse also triggers the reference voltage of the comparator to change from Vref$_H$ the low reference voltage (Vref$_L$). When the capacitor voltage (A") is discharged to Vref$_L$, the comparator output (B") returns to low. The low comparator output (B") may open the second integrator switch 112 and virtually simultaneously the high inverter output (C") closes the first integrator switch 110 allowing capacitor 116 to begin charging again. The low comparator output (B") also triggers the comparator reference voltage to change from Vref$_L$ back to Vref$_H$.

An advantage of this embodiment is that sensor signal errors, which may be created due to capacitor discharge time, are reduced since the magnitude of the analog sensor signal Isig drives both the charging and the discharging rates of the capacitor 116.

I to F, Dual Capacitor

In further alternative embodiments, more than one capacitor is used such that as one capacitor is charging, at a rate proportional to the magnitude of the analog sensor signal Isig, another capacitor is discharging. An example of this embodiment is shown in FIG. 14. A series of three switches are used for each capacitor. A first group of switches 210 is controlled by a latch voltage C'", and a second group of switches 212 are controlled by voltage D'", which is the inverse of C'". Substantially, only one group of switches is closed at a time. If the first group of switches 210 is closed, the voltage across a first capacitor 216 increases at a rate proportional to the analog sensor signal Isig until the integrator voltage (A'") at the output of Op-Amp 214 achieves a reference voltage (Vref). At the same time one of the switches shorts the circuit across a second capacitor 222 causing it to discharge. A comparator 220 compares the integrator output (A'") to the reference voltage Vref. As the integrator output (A'") reaches Vref, the comparator output (B'") generates a pulse. The comparator output pulse increments a counter 76, and triggers the latch output voltage C'" from a latch 221 to toggle from a low voltage to a high voltage. The change in the latch voltage C'" causes the second group of switches 212 to close and the first group of switches 210 to open. One of the switches from the second group of switches 212 shorts the circuit across the first capacitor 216 causing it to discharge. At the same time the voltage across the second capacitor 222 increases at a rate proportional to the analog sensor signal Isig until the integrator voltage (A''') at the output of Op-Amp 214 achieves a reference voltage (Vref). Again, the comparator 220 compares the integrator output (A''') to the reference voltage Vref. And when the integrator output (A''') reaches Vref, the comparator output (B''') generates a pulse. The comparator output pulse increments the counter 76, and triggers the latch output voltage C''' to toggle from a high voltage to a low voltage, which causes the switches to return to their initial position with the first group of switches 210 closed and the second group of switches 212 to open.

In summary, as blood glucose level 18 increases, the analog sensor signal Isig increases, which causes the voltage coming out of integrator 72 to ramp up faster to the high reference voltage $Vref_H$, which causes comparator 74 to generate pulses more often, which adds counts to counter 76 faster. Therefore, higher blood glucose levels generate more counts per minute.

The charge storage capacity for the capacitors used in integrator 72, and the reference voltages $Vref_H$, and $Vref_L$ may be selected such that the count resolution for counts collected in a one-minute period at a glucose level of 200 mg/dl represents a blood glucose measurement error of less than 1 mg/dl. In particular embodiments, $Vref_H$ is 1.1 volts and $Vref_L$ is 0.1 volts. Higher or lower reference voltages may be selected based on the magnitude of the analog sensor signal Isig, the capacity of the capacitors, and the desired measurement resolution. The source voltage V+ is set to a voltage sufficiently high to discharge one or more capacitors quickly enough that the discharge times do not significantly reduce the number of counts per minute at a blood glucose level of 200 mg/dl.

Pulse Duration Output Feature

In particular embodiments, transmitter 70 transmits digital sensor values Dsig from buffer 78 whenever triggered by clock 80. However, in particular embodiments, the user or another individual may use a selector 96 to choose other outputs to be transmitted from the transmitter 70, as shown in FIG. 11(b). In particular embodiments, selector 96 is in the form of a menu displayed on a screen that is accessed by the user or another individual by using buttons on the surface of telemetered characteristic monitor transmitter 30. In other embodiments, a dial selector, dedicated buttons, a touch screen, a signal transmitted to the telemetered characteristic monitor transmitter 30, or the like, may be used. Signals that may be selected to be transmitted, other than the digital sensor values Dsig, include, but are not limited to, a single pulse duration, digital sensor values before pre-filtering, digital sensor values after pre-filtering but before filtering, digital sensor values after filtering, or the like.

In particular embodiments, a pulse duration counter 98 counts clock pulses from a pulse duration clock 100 until pulse duration counter 98 is reset by a rising or falling edge of a pulse from comparator 74, as shown in FIG. 11(b). The accumulated count at the time that pulse duration counter 98 is reset represents the pulse duration for a portion of a single pulse from comparator 74. The accumulated count from the pulse duration counter 98 is stored in the single pulse buffer 102 if triggered by the reset signal. If an individual selects the single pulse output, transmitter 70 transmits the values from single pulse buffer 102. The pulse duration clock 100 period must be sufficiently shorter than the period between individual pulse edges from the comparator 74 given a high analog sensor signal Isig to have sufficient resolution to quantify different pulse durations from the comparator 74.

I to V (Current to Voltage), Voltage A/D

Figure 15:
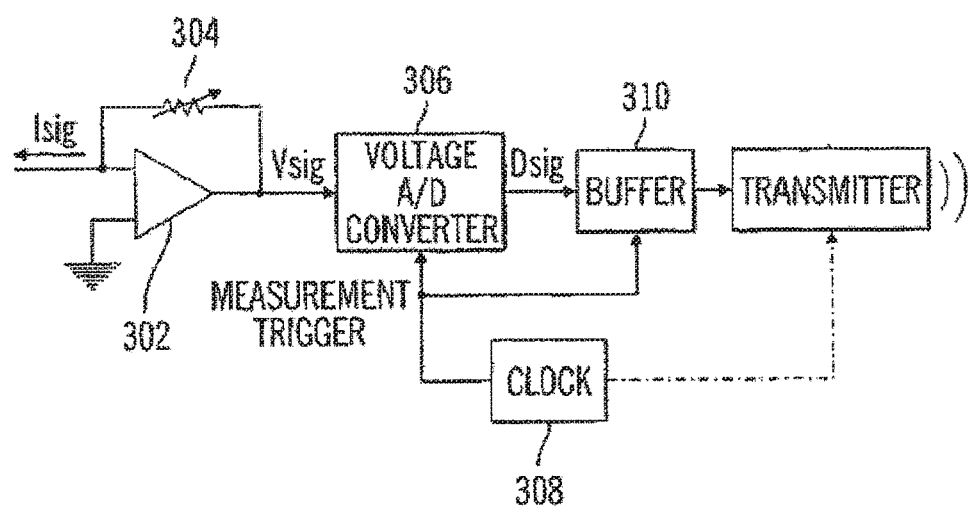
FIG. 15 is a circuit diagram of an I-V A/D converter of FIG. 10 in accordance with an embodiment.

Alternative methods may be used to convert the analog sensor signal Isig from an analog current signal to a digital voltage signal. The analog sensor signal Isig is converted to an analog voltage Vsig using an Op Amp 302 and a resistor 304, as shown in FIG. 15. And then periodically a clock 308 triggers an A/D converter 306 to take a sample value from the analog voltage Vsig and convert it to a digital signal representing the magnitude of the voltage. The output values of the A/D converter 306 are digital sensor values Dsig. The digital sensor values Dsig are sent to a buffer 310 and then to the transmitter 70. In particular embodiments, resistor 304 may be adjusted to scale the Vsig to use a significant portion of the range of voltage A/D converter 306 depending on the sensor sensitivity, the maximum glucose concentration to be measured, the desired resolution from voltage A/D converter 306, or the like.

In alternative embodiments, a buffer 310 is not needed and the digital sensor values Dsig are sent from the A/D converter directly to the transmitter 70. In other alternative embodiments, the digital sensor values Dsig are processed, filtered, modified, analyzed, smoothed, combined, averaged, clipped, scaled, calibrated, or the like, before being sent to the transmitter 70. In preferred embodiments, the clock 308 triggers a measurement every 10 seconds. In alternative embodiments, the clock 308 runs faster or slower triggering measurements more or less frequently depending on how quickly the blood glucose level can change, the sensor sensitivity, how often new measurements are needed to control the delivery system 14, or the like.

Finally, in other alternative embodiments, other sensor signals from other types of sensors, as discussed in the section "Sensor and Sensor Set" below, are converted to digital sensor values Dsig if necessary before transmitting the digital sensor values Dsig to another device.

Unless specifically stated otherwise, as apparent from the following discussion, it is appreciated that throughout this specification discussions utilizing terms such as "processing", "computing", "calculating", "determining", "estimating", "selecting", "weighting", "identifying", "obtaining", "representing", "receiving", "transmitting", "storing", "analyzing", "creating", "contracting", "associating", "updating", or the like refer to the actions or processes that may be performed by a of a specific apparatus, such as a special purpose computer, special purpose computing apparatus, or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device. In a particular example, such a special purpose computer may comprise one or more processors programmed with instructions to perform one or more specific functions. Accordingly, a special purpose computer refers to a system or a device that includes the ability to process or store data in the form of signals. Further, unless specifically stated otherwise, a process as described herein, with reference to flow diagrams or otherwise, may also be executed or controlled, in whole or in part, by a special purpose computer.

It should be noted that, although aspects of the above system, method, or process have been described in a particular order, the specific order is merely an example of a process and claimed subject matter is of course not limited to the order described. It should also be noted that the systems, methods, and processes described herein, may be capable of being performed by one or more computing platforms. In addition, the methods or processes described herein may be capable of being stored on a storage medium as one or more machine readable instructions, that if executed may enable a computing platform to perform one or more actions. "Storage medium" as referred to herein relates to media capable of storing information or instructions which may be operated on, or executed by, by one or more machines. For example, a storage medium may comprise one or more storage devices for storing machine-readable instructions or information. Such storage devices may comprise any one of several media types including, for example, magnetic, optical or semiconductor storage media. For further example, one or more computing platforms may be adapted to perform one or more of the processed or methods in accordance with claimed subject matter, such as the methods or processes described herein. However, these are merely examples relating to a storage medium and a computing platform and claimed subject matter is not limited in these respects.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

What is claimed is:

1. A method comprising:
   receiving a signal representative of a measurement value entered at an operator interface;
   receiving signals representative of blood glucose sensor measurements obtained subsequent to receipt of the signal representative of the measurement value; and
   executing instructions on a special purpose computing apparatus to:
   compute one or more commands to a delivery system based, at least in part, on the received signals representative of the blood glucose sensor measurements; and
   determine a maximum duration following entry of the measurement value until initiation of an alert to an operator based, at least in part, on at least one of the one or more computed commands.

2. The method of claim 1, wherein the maximum duration to be based, at least in part, on the measurement value.

3. The method of claim 1, and further comprising executing the instructions on the special purpose computing apparatus to determine the maximum duration based, at least in part, on a signal representative of a measured rate of change in blood glucose of a patient.

4. The method of claim 1,
   wherein the one or more computed command to the delivery system comprise one or more proportional, plus integral, plus derivative (PID) commands based, at least in part, on the signals representative of the blood glucose sensor measurements.

5. The method of claim 1, and further comprising executing the instructions on the special purpose computing apparatus to:
   determine the maximum duration based, at least in part, on whether a glucose bolus was infused to a patient contemporaneously with receipt of the signal representative of the measurement value.

6. The method of claim 1, and further comprising further executing the instructions on the special purpose computing apparatus to determine the maximum duration based, at least in part, on one or more signals representative of a measured rate of change in blood glucose of a patient.

7. The method of claim 1, wherein the entered measurement value to comprise a blood glucose sample measurement value.

8. The method of claim 1, and further comprising generating the alert as a callback alert message to an attendant.

9. The method of claim 8, and further comprising shortening the maximum duration based, at least in part, on a forecasted blood glucose level, proximity of a blood glucose level to limits of a target blood glucose range or proximity of the blood glucose level to hypoglycemic or hyperglycemic warning limits, or a combination thereof.

10. An apparatus comprising:
    an operator interface to receive entry of an input value representative of a measurement value;
    a blood glucose sensor to provide signals representative of blood glucose sensor measurements obtained from a patient;
    and
    one or more processors to:
    compute one or more commands to a delivery system based, at least in part, on signals representative of blood glucose sensor measurements obtained from the blood glucose sensor subsequent to entry of the input value; and
    determine a maximum duration following entry of the measured value until initiation of an alert to an operator based, at least in part, on at least one of the one or more computed commands.

11. The apparatus of claim 10, wherein the maximum duration to be determined based, at least in part, on the measurement value.

12. The apparatus of claim 10, wherein the one or more processors to be further adapted to determine the maximum duration based, at least in part, on a signal representative of a measured rate of change in blood glucose of the patient.

13. The apparatus of claim 10,
    wherein the computed one or more commands comprise one or more proportional, plus integral, plus derivative (PID) commands based, at least in part, on the signals representative of blood glucose sensor measurements.

14. The apparatus of claim 10, wherein the one or more processors to be further adapted to:
    determine the maximum duration further based, at least in part, on whether a glucose bolus was infused to a patient contemporaneously with entry of the input value representative of the measurement value.

15. The apparatus of claim 10, wherein the one or more processors to be further adapted to determine the maximum duration further based, at least in part, on one or more signals representative of a measured rate of change in blood glucose of a patient.

16. The apparatus of claim 10, wherein the measurement value to comprise a blood glucose sample measurement value.

17. The apparatus of claim 10, wherein the one or more processors to be further adapted to generate a callback alert message to an attendant at an instance prior to expiration of the maximum duration.

18. The apparatus of claim 10, wherein the one or more processors to be further adapted to determine an instance prior to expiration of the maximum duration based, at least in part, on a forecasted blood glucose level, proximity of a blood glucose level to limits of a target blood glucose range or proximity of the blood glucose level to hypoglycemic or hyperglycemic warning limits, or a combination thereof.

19. The apparatus of claim 10, wherein the maximum duration to be further based, at least in part, on an indication of a predetermined predisposition for hypoglycemia in a patient.

20. The apparatus of claim 19, wherein the one or more processors to be further adapted to obtain the indication of the predetermined predisposition for hypoglycemia in the patient from one or more entries to the operator interface or an indication received from a remote database to be accessible by the apparatus over an electronic data communication network, or a combination thereof.

* * * * *